United States Patent
Cuberes-Altisent et al.

(10) Patent No.: US 9,567,338 B2
(45) Date of Patent: Feb. 14, 2017

(54) **PYRAZOLO[3,4-*D*]PYRIMIDINE COMPOUNDS, THEIR PREPARATION AND USE AS SIGMA LIGANDS**

(75) Inventors: Maria Rosa Cuberes-Altisent, San Cugat del Valles (ES); Jordi Corbera-Arjona, Terrasa (ES); Jose Luis Diaz-Fernandez, Manresa (ES); Carmen Almansa-Rosales, Barcelona (ES)

(73) Assignee: LABORATORIOS DEL DR. ESTEVE S.A., Barcelona (ES)

( * ) Notice: Subject to any disclaimer, the term of this patent is extended or adjusted under 35 U.S.C. 154(b) by 0 days.

(21) Appl. No.: 14/234,035

(22) PCT Filed: Jul. 13, 2012

(86) PCT No.: PCT/EP2012/063825
§ 371 (c)(1),
(2), (4) Date: Jan. 27, 2014

(87) PCT Pub. No.: WO2013/010950
PCT Pub. Date: Jan. 24, 2013

(65) Prior Publication Data
US 2014/0163010 A1 Jun. 12, 2014
US 2015/0315190 A2 Nov. 5, 2015

(30) Foreign Application Priority Data

Jul. 21, 2011 (EP) .................................. 11382249

(51) Int. Cl.
C07D 487/04 (2006.01)

(52) U.S. Cl.
CPC ................... C07D 487/04 (2013.01)

(58) Field of Classification Search
CPC .................................................. C07D 487/04
See application file for complete search history.

(56) References Cited

U.S. PATENT DOCUMENTS 6,660,845 B1* 12/2003 Gall et al. .................... 536/23.1
2008/0275054 A1* 11/2008 Holzer et al. ............ 514/252.16

FOREIGN PATENT DOCUMENTS

| EP | 1 634 873 A1 | 3/2006 |
|---|---|---|
| EP | 1 634 973 A1 | 3/2006 |
| EP | 1 847 542 | 10/2007 |
| GB | WO 2010/084300 | * 7/2010 |
| WO | WO 0110880 A1 | 2/2001 |
| WO | WO 2007/062805 A1 | 6/2007 |
| WO | WO 2007/098961 | 9/2007 |
| WO | WO2007/126841 | 11/2007 |
| WO | WO 2008/049105 | 4/2008 |
| WO | WO 2009/068617 A1 | 6/2009 |
| WO | WO 2009/073153 A2 | 6/2009 |
| WO | WO 2010/084300 A2 | 7/2010 |

OTHER PUBLICATIONS

Wolff, Manfred E. "Burger's Medicinal Chemistry, 5ed, Part I", John Wiley & Sons, 1995, pp. 975-977.*
Banker et al, "Modern Pharmaceutics, 3ed.", Marcel Dekker, New York, 1996, pp. 451 and 596.*
Jordan, V. C. Nature Reviews: Drug Discovery, 2, 2003, pp. 205-213.*
Leonova et al. (Khimiya Geterotsiklicheskikh Soedinenii (1982), (7); pp. 982-984).*
Chemical Abstracts—Ambinter chemical supplier—for sale on Feb., Jul. and Aug. 2009.*
Bowen, Wayne D., "Sigma receptors: recent advances and new clinical potentials", Pharmaceutica Acta Helvetiae 74, pp. 211-218, 2000.
DeHaven-Hudkins et al., "Characterization of the binding of [$^3$H](+)-pentazocine to σ recognition sites in guinea pig brain", European Journal of Pharmacology—Molecular Pharmacology Section, 227, pp. 371-378, 1992.
Hanner et al., "Purification, molecular cloning, and expression of the mammalian sigma$_1$ -binding site", Proc. Natl. Acad. Sci., vol. 93, pp. 8072-8077, Jul. 1996.
Ronsisvalle et al., "Opioid and sigma receptor studies. New developments in the design of selective sigma ligands", Pure Appl. Chem . . . , vol. 73, No. 9, pp. 1499-1509, 2001.
Gupta et al., "Synthesis of N-aryl-5-amino-4-cyanopyrazole derivatives as potent xanthine oxidase inhibitors", European Journal of Medicinal Chemistry 43, pp. 771-780, 2008.
Kaiser, "Binding to the sigma receptor", pp. 1-2, 1991.
Quirion et al., "Meeting Report: A proposal for the classification of sigma binding sites", TiPs, vol. 13, pp. 85-86, Mar. 1992.
Robins, Roland K., "Potential Purine Antagonists. I. Synthesis of Some 4,6-Substituted Pyrazolo [3,4-d] pyrimidines", vol. 78, pp. 784-790, Feb. 20, 1956.

(Continued)

*Primary Examiner* — Valerie Rodriguez-Garcia
(74) *Attorney, Agent, or Firm* — Ostrolenk Faber LLP

(57) ABSTRACT

Pyrazolo[3,4-d]pyrimidine compounds having a great affinity for sigma receptors, especially sigma-1 receptors, as well as a process for preparing these compounds, compositions comprising them and their use as medicaments. The compounds have the following general formula (I):

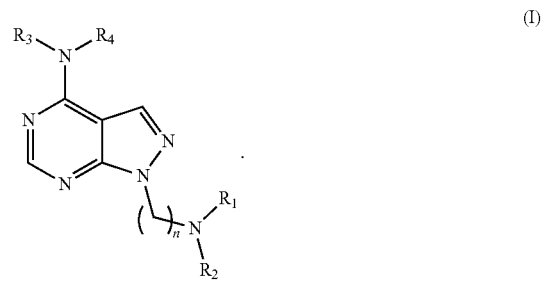

10 Claims, No Drawings

(56) References Cited

OTHER PUBLICATIONS

Snyder et al., "Receptor Mechanisms in Antipsychotic Drug Action: Focus on Sigma Receptors", Journal of Neuropsychiatry, vol. 1, No. 1, pp. 7-15, 1989.
Walker et al., "Sigma Receptors: Biology and Function", Pharmacological Reviews, vol. 42, No. 4, pp. 355-402, 1990.
Rosemeyer et al., "Symmetrically and Unsymmetrically Bridged Methylenebis (allopurinols): Synthesis of Dimeric Potential Anti-Gout Drugs", Molecules, vol. 12, pp. 563-575, 2007.
Leonova et al., "Some reactions of 4-aminopyrazolo [3,4-d] pyrimidines", Chemistry of Heterocyclic Compounds, vol. 18, Issue 7, pp. 753-754, 1982.
Asaka et al., "Preparation of Erythromycin A Derivatives as Antibacterial Agent". (Abstract Only).
Hsu et al., "Studies on 4-aminopyrazolo [3,4-d] pyrimidine; action of derivatives and analogs on HeLa cells". (Abstract Only).
Adams et al., "Stem Cell Culture Methods and Method of Inhibiting Stem Cell Differentiation". (Abstract Only).
International Search Report dated Aug. 28, 2012 issued in corresponding International patent application No. PCT/EP2012/063825.

\* cited by examiner

PYRAZOLO[3,4-D]PYRIMIDINE COMPOUNDS, THEIR PREPARATION AND USE AS SIGMA LIGANDS

CROSS REFERENCE TO RELATED APPLICATIONS

The present application is a 35 U.S.C. §371 National Phase conversion of PCT/EP2012/063825, filed Jul. 13, 2012, which claims benefit of European Application No. 11382249.8, filed Jul. 21, 2011, the disclosure of which is incorporated herein by reference. The PCT International Application was published in the English language.

FIELD OF THE INVENTION

The present invention relates to new pyrazolo[3,4-d] pyrimidine compounds having a great affinity for sigma receptors, especially sigma-1 receptors as well as to the process for the preparation thereof, to composition comprising them and to their use as medicaments.

BACKGROUND OF THE INVENTION

The search for new therapeutic agents has been greatly aided in recent years by better understanding of the structure of proteins and other biomolecules associated with target diseases. One important class of these proteins are sigma (σ) receptors cell surface receptors of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J. M. et al, Pharmacological Reviews, 1990, 42, 355). It has been reported that the known sigma receptor ligand rimcazole clinically shows effects in the treatment of psychosis (Snyder, S. H., Largent, B. L. J. Neuropsychiatry 1989, 1, 7). The sigma binding sites have preferential affinity for the dextrorotatory isomers of certain opiate benzomorphans, such as (+)-SKF-10047, (+)-cyclazocine, and (+)-pentazocine and also for some narcoleptics such as haloperidol.

"The sigma receptor/s" as used in this application is/are well known and defined using the following citation: This binding site represents a typical protein different from opioid, NMDA, dopaminergic, and other known neurotransmitter or hormone receptor families (G. Ronsisvalle et al. Pure Appl. Chem. 73, 1499-1509 (2001)).

The sigma receptor has at least two subtypes, which may be discriminated by stereoselective isomers of these pharmacoactive drugs. SKF-10047 has nanomolar affinity for the sigma 1 (σ-1) site, and has micromolar affinity for the sigma 2 (σ-2) site. Haloperidol has similar affinities for both subtypes.

The Sigma-1 receptor is a non-opiaceous type receptor expressed in numerous adult mammal tissues (central nervous system, ovary, testicle, placenta, adrenal gland, spleen, liver, kidney, gastrointestinal tract, etc.) as well as in embryo development from its earliest stages, and is apparently involved in a large number of physiological functions. Its high affinity for various pharmaceuticals has been described, such as for SKF-10047, (+)-pentazocine, haloperidol and rimcazole, among others, known ligands with analgesic, anxiolytic, antidepressive, antiamnesic, antipsychotic and neuroprotective activity. The sigma-1 receptor is of great interest in pharmacology in view of its possible physiological role in processes related to analgesia, anxiety, addiction, amnesia, depression, schizophrenia, stress, neuroprotection and psychosis [Kaiser et al (1991) Neurotransmissions 7 (1): 1-5], [Walker, J. M. et al, Pharmacological Reviews, 1990, 42, 355] and [Bowen W. D. (2000) Pharmaceutica Acta Helvetiae 74: 211-218].

The Sigma-2 receptor is also expressed in numerous adult mammal tissues (nervous system, immune system, endocrine system, liver, kidney, etc.). Sigma-2 receptors can be components in a new apoptosis route that may play an important role in regulating cell proliferation or in cell development. This route seems to consist of Sigma-2 receptors joined to intracellular membranes, located in organelles storing calcium, such as the endoplasmic reticulum and mitochondria, which also have the ability to release calcium from these organelles. The calcium signals can be used in the signalling route for normal cells and/or in induction of apoptosis.

Agonists of Sigma-2 receptors induce changes in cell morphology, apoptosis in several types of cell lines and regulate the expression of p-glycoprotein mRNA, so that they are potentially useful as antineoplasic agents for treatment of cancer. In fact, Sigma-2 receptor agonists have been observed to induce apoptosis in mammary tumour cell lines resistant to common antineoplasic agents that damage the DNA. In addition, agonists of Sigma-2 receptors enhance the cytotoxic effects of these antineoplasic agents at concentrations in which the agonist is not cytotoxic. Thus, agonists of Sigma-2 receptors can be used as antineoplasic agents at doses inducing apoptosis or at sub-toxic doses in combination with other antineoplasic agents to revert the resistance to the drug, thereby allowing using lower doses of the antineoplasic agent and considerably reducing its adverse effects.

Antagonists of Sigma-2 receptors can prevent the irreversible motor side effects caused by typical neuroleptic agents. In fact, it has been found that antagonists of Sigma-2 receptors can be useful as agents for improving the weakening effects of delayed dyskinesia appearing in patients due to chronic treatment of psychosis with typical antipsychotic drugs, such as haloperidol. Sigma-2 receptors also seem to play a role in certain degenerative disorders in which blocking these receptors could be useful.

Endogenous sigma ligands are not known, although progesterone has been suggested to be one of them. Possible sigma-site-mediated drug effects include modulation of glutamate receptor function, neurotransmitter response, neuroprotection, behavior, and cognition (Quirion, R. et al. Trends Pharmacol. Sci., 1992, 13:85-86). Most studies have implied that sigma binding sites (receptors) are plasmalemmal elements of the signal transduction cascade. Drugs reported to be selective sigma ligands have been evaluated as antipsychotics (Hanner, M. et al. Proc. Natl. Acad. Sci., 1996, 93:8072-8077). The existence of sigma receptors in the CNS, immune and endocrine systems have suggested a likelihood that it may serve as link between the three systems.

In view of the potential therapeutic applications of agonists or antagonists of the sigma receptor, a great effort has been directed to find selective ligands. Thus, the prior art discloses different sigma receptor ligands.

For instance, the international patent application WO2007/098961 describes 4,5,6,7 tetrahydrobenzo[b]thiophene derivatives having pharmacological activity towards the sigma receptor.

Spiro[benzopyran] or spiro[benzofuran] derivatives were also disclosed in EP1847542 as well as pyrazole derivatives (EP1634873) with pharmacological activity on sigma receptors.

WO 2008049105 discloses some pyrazolo[3,4-d]pyrimidine compounds but they are rather inhibitors of Heat Shock Protein 90 (HSP90) and useful to treat disorders mediated by HSP90.

There is still a need to find compounds having pharmacological activity towards the sigma receptor, being both effective and selective, and having good "drugability" properties, i.e. good pharmaceutical properties related to administration, distribution, metabolism and excretion.

SUMMARY OF THE INVENTION

The present invention discloses novel compounds with great affinity to sigma receptors which might be used for the treatment of sigma related disorders or diseases.

Specifically, it is an object of the present invention novel pyrazolo[3,4-d]pyrimidine compounds of general formula (I):

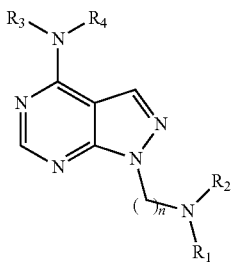

(I)

where $R_1$, $R_2$, $R_3$ and $R_4$ are as described below.

It is also an object of the invention different processes for their preparation, including a process for preparing enantiomerically pure compounds of formula (I).

Another object of the invention refers to the use of such compounds of general formula I for the manufacture of a medicament for the treatment or prophylaxis of sigma receptor mediated diseases or conditions, especially sigma-1 mediated diseases or conditions. Within the group of diseases or conditions mediated by the sigma receptor for which the compounds of the invention are effective, diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases, may be cited. Compounds of the invention are very good anxiolytic and immunosuppressant and are especially useful in the treatment and profilaxis of pain, especially neuropathic pain, inflammatory pain or other pain conditions involving allodynia and/or hyperalgesia.

It is also an object of the invention pharmaceutical compositions comprising one or more compounds of general formula (I) with at least one pharmaceutically acceptable excipient. The pharmaceutical compositions in accordance with the invention can be adapted in order to be administered by any route of administration, be it orally or parenterally, such as pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

DETAILED DESCRIPTION OF THE INVENTION

The invention first relates to compounds of general formula (I):

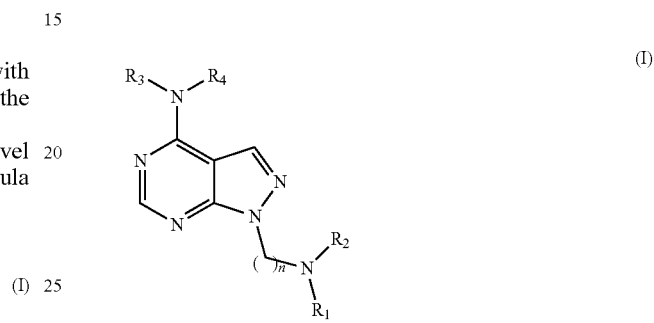

(I)

wherein
$R_1$ and $R_2$ independently represent a hydrogen atom;
a branched or unbranched, saturated or unsaturated, optionally at least monosubstituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$ or a benzhydryl group optionally monosubstituted;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;
or $R_1$ and $R_2$ together with the bridging nitrogen form a substituted or unsubstituted cycloalkyl radical $C_{3-9}$; a substituted or unsubstituted heterocyclyl group $C_{3-9}$ or a substituted or unsubstituted heteroaryl radical $C_{3-9}$;
$R_3$ and $R_4$ independently represent a hydrogen atom; a —$COR_5$; —$C(O)NR_5R_6$; —$C(S)NR_5R_6$; —$SO_2R_7$; —$C(O)OR_5$; —$OR_5$; —$NR_5R_6$; $NR_5C(O)R_6$; —$NCR_5R_6$;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$ or a benzhydryl group optionally monosubstituted;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclylalkyl radical $C_{3-9}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;
or $R_3$ and $R_4$ together with the bridging nitrogen form a substituted or unsubstituted cycloalkyl radical $C_{3-9}$; a substituted or unsubstituted heterocyclyl group $C_{3-9}$ or a substituted or unsubstituted heteroaryl radical $C_{3-9}$;
$R_5$, $R_6$ and $R_7$ independently represent a hydrogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$ or a benzhydryl group optionally monosubstituted;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;
n is selected from 1, 2, 3 or 4;
or a pharmaceutically acceptable salt, isomer, prodrug or solvate thereof.

Aliphatic radicals $C_{1-10}$, as referred to in the present invention, are optionally mono- or polysubstituted and may be branched or unbranched, saturated or unsaturated. Unsaturated aliphatic groups, as defined in the present invention, include alkyl, alkenyl and alkinyl radicals. Preferred aliphatic radicals according to the present invention include but are not restricted to methyl, ethyl, vinyl (ethenyl), ethinyl, propyl, n-propyl, isopropyl, allyl (2-propenyl), 1-propinyl, methylethyl, butyl, n-butyl, iso-butyl, sec-butyl, tert-butyl butenyl, butinyl, 1-methylpropyl, 2-methylpropyl, 1,1-dimethylethyl, pentyl, n-pentyl, 1,1-dimethylpropyl, 1,2-dimethylpropyl, 2,2-dimethylpropyl, hexyl, 1-methylpentyl, n-heptyl, n-octyl, n-nonyl and n-decyl. Preferred substituents for aliphatic radicals, according to the present invention, are a $C_{1-4}$ alkyl group, a linear or branched $C_{1-6}$ alkoxy group, F, Cl, I, Br, CF$_3$, CH$_2$F, CHF$_2$, CN, OH, SH, NH$_2$, oxo, (C=O)R', SR', SOR', SO$_2$R', NHR', NR'R'' whereby R' and optionally R'' for each substituent independently represents a linear or branched $C_{1-6}$-alkyl group.

Alkyl radicals, as referred to in the present invention, are saturated aliphatic radicals. They may be linear or branched and are optionally substituted.

Cycloalkyl radical $C_{3-9}$, as referred to in the present invention, are understood as meaning saturated and unsaturated (but not aromatic), cyclic hydrocarbons, which can optionally be unsubstituted, mono- or polysubstituted. In these radicals, for example $C_{3-4}$-cycloalkyl represents $C_3$- or $C_4$-cycloalkyl, $C_{3-6}$-cycloalkyl represents $C_3$-, $C_4$- or $C_5$-cycloalkyl, etc. With respect to cycloalkyl, the term also includes saturated cycloalkyls in which optionally at least one carbon atom may be replaced by a heteroatom, preferably S, N, P or O. However, mono- or polyunsaturated, preferably monounsaturated, cycloalkyls without a heteroatom in the ring also in particular fall under the term cycloalkyl as long as the cycloalkyl is not an aromatic system.

Examples for cycloalkyl radical preferably include but are not restricted to cyclopropyl, 2-methylcyclopropyl, cyclopropylmethyl, cyclobutyl, cyclopentyl, cyclopentylmethyl, cyclohexyl, cycloheptyl, cyclooctyl, acetyl, tert-butyl, adamantyl, noradamantyl, pyrroline, pyrrolidine, pyrrolidine-one, pyrazoline, pyrazolinone, oxopyrazolinone, aziridine, azetidine, tetrahydropyrrole, oxirane, oxetane, dioxetane, tetrahydrofurane, dioxane, dioxolane, oxathiolane, oxazolidine, thiirane, thietane, thiolane, thiane, thiazolidine, piperidine, piperazine, morpholine or azepane.

Cycloalkyl radicals $C_{3-9}$, as defined in the present invention, are optionally mono- or polysubstituted by substitutents independently selected from a $C_{1-4}$-alkyl group, a linear or branched $C_{1-6}$-alkoxy group, a phenyl group, F, Cl, I, Br, CF$_3$, CH$_2$F, CHF$_2$, CN, OH, SH, NH$_2$, oxo (=O), (C=O)R', SR', SOR', SO$_2$R', NHR', NR'R'' whereby R' and optionally R'' for each substituent independently represents a linear or branched $C_{1-6}$-alkyl group.

An aryl radical, as referred to in the present invention, is understood as meaning ring systems with at least one aromatic ring but without heteroatoms even in only one of the rings. These aryl radicals may optionally be mono- or polysubstituted by substitutents independently selected from a $C_{1-4}$ alkyl group, a linear or branched $C_{1-6}$ alkoxy group, an optionally at least mono-substituted phenyl group, F, Cl, I, Br, CF$_3$, CH$_2$F, CHF$_2$, CN, OH, SH, NH$_2$, oxo, (C=O)R', SR', SOR', SO$_2$R', N(C=O) OR', NHR', NR'R'' whereby R' and optionally R'' for each substituent independently represents a linear or branched $C_{1-6}$-alkyl group. Preferred examples of aryl radicals include but are not restricted to phenyl, naphthyl, fluoranthenyl, fluorenyl, tetralinyl or indanyl or anthracenyl radicals, which may optionally be mono- or polysubstituted, if not defined otherwise.

An arylalkyl radical $C_{1-10}$, as defined in the present invention, comprises a linear or branched, optionally at least mono-substituted alkyl chain which is bonded to an aryl group, as defined above. A preferred aryl-alkyl radical is a benzyl group, wherein the alkyl chain is optionally branched or substituted. Preferred substituents for aryl-alkyl radicals, according to the present invention, are F, Cl, Br, I, NH$_2$, SH, OH, SO$_2$, CF$_3$, carboxy, amido, cyano, carbamyl, nitro, phenyl, benzyl, —SO$_2$NH$_2$, $C_{1-6}$ alkyl and/or $C_{1-6}$-alkoxy.

A heteroaryl radical $C_{3-9}$, is understood as meaning heterocyclic ring systems which have at least one aromatic ring and may optionally contain one or more heteroatoms from the group consisting of nitrogen, oxygen and/or sulfur and may optionally be mono- or polysubstituted by substitutents independently selected from a $C_{1-4}$-alkyl group, a linear or branched $C_{1-6}$ alkoxy group, F, Cl, I, Br, CF$_3$, CH$_2$F, CHF$_2$, CN, OH, SH, NH$_2$, oxo, (C=O)R', SR', SOR', SO$_2$R', NHR', NR'R" whereby R' and optionally R" for each substituent independently represents a linear or branched $C_{1-6}$-alkyl group. Preferred examples of heteroaryls include but are not restricted to furan, benzofuran, thiophene, benzothiophene, imidazole, pyrrole, pyridine, pyrimidine, pyridazine, pyrazine, quinoline, isoquinoline, phthalazine, benzo-1,2,5-thiadiazole, benzothiazole, indole, benzotriazole, benzodioxolane, benzodioxane, benzimidazole, carbazole and quinazoline.

The term "condensed" according to the present invention means that a ring or ring-system is attached to another ring or ring-system, whereby the terms "annulated" or "annelated" are also used by those skilled in the art to designate this kind of attachment.

The term "ring system" according to the present invention refers to ring systems comprises saturated, unsaturated or aromatic carbocyclic ring systems which contain optionally at least one heteroatom as ring member and which are optionally at least mono-substituted. Said ring systems may be condensed to other carbocyclic ring systems such as aryl groups, naphtyl groups, heteroaryl groups, cycloalkyl groups, etc.

Cyclyl groups/radicals $C_{3-9}$, as defined in the present invention, comprise any saturated, unsaturated or aromatic carbocyclic ring systems which contain optionally at least one heteroatom as ring member and which are optionally at least mono-substituted. Cyclyl groups preferably comprise aryl, heteroaryl, cyclyl, heterocylcyl and/or spiro ring systems.

Heterocyclyl groups/radicals $C_{3-9}$, as defined in the present invention, comprise any saturated, unsaturated or aromatic carbocyclic ring systems which are optionally at least mono-substituted and which contain at least one heteroatom as ring member. Preferred heteroatoms for these heterocyclyl groups are N, S or O. Preferred substituents for heterocyclyl radicals, according to the present invention, are F, Cl, Br, I, $NH_2$, SH, OH, $SO_2$, $CF_3$, carboxy, amido, cyano, carbamyl, nitro, phenyl, benzyl, —$SO_2NH_2$, $C_{1-6}$ alkyl and/or $C_{1-6}$-alkoxy.

The term "salt" must be understood as any form of an active compound used in accordance with this invention in which the said compound is in ionic form or is charged and coupled to a counter-ion (a cation or anion) or is in solution. This definition also includes quaternary ammonium salts and complexes of the active molecule with other molecules and ions, particularly complexes formed via ionic interactions. The definition particularly includes physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly as a result of the counter-ion) when used in an appropriate manner for a treatment, particularly applied or used in humans and/or mammals. These physiologically acceptable salts may be formed with cations or bases and, in the context of this invention, are understood to be salts formed by at least one compound used in accordance with the invention—normally an acid (deprotonated)—such as an anion and at least one physiologically tolerated cation, preferably inorganic, particularly when used on humans and/or mammals. Salts with alkali and alkali earth metals are particularly preferred, as well as those formed with ammonium cations ($NH_4^+$). Preferred salts are those formed with (mono) or (di)sodium, (mono) or (di)potassium, magnesium or calcium. These physiologically acceptable salts may also be formed with anions or acids and, in the context of this invention, are understood as being salts formed by at least one compound used in accordance with the invention—normally protonated, for example in nitrogen—such as a cation and at least one physiologically tolerated anion, particularly when used on humans and/or mammals. This definition specifically includes in the context of this invention a salt formed by a physiologically tolerated acid, i.e. salts of a specific active compound with physiologically tolerated organic or inorganic acids—particularly when used on humans and/or mammals. Examples of this type of salts are those formed with: hydrochloric acid, hydrobromic acid, sulphuric acid, methanesulfonic acid, formic acid, acetic acid, oxalic acid, succinic acid, malic acid, tartaric acid, mandelic acid, fumaric acid, lactic acid or citric acid.

The term "solvate" in accordance with this invention should be understood as meaning any form of the active compound in accordance with the invention in which said compound is bonded by a non-covalent bond to another molecule (normally a polar solvent), especially including hydrates and alcoholates, for example methanolate.

In a particular and preferred embodiment of the invention $R_1$ and $R_2$ independently represent a hydrogen atom; a branched or unbranched, saturated or unsaturated, optionally at least mono-substituted, aliphatic radical $C_{1-10}$; or $R_1$ and $R_2$ together with the bridging nitrogen form a substituted or unsubstituted cycloalkyl radical $C_{3-9}$; a substituted or unsubstituted heterocyclyl group $C_{3-9}$ or a substituted or unsubstituted heteroaryl radical $C_{3-9}$.

In another preferred embodiment of the invention $R_3$ and $R_4$ independently represent a hydrogen atom; or an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; or $R_3$ and $R_4$ together with the bridging nitrogen form a substituted or unsubstituted cycloalkyl radical $C_{3-9}$; a substituted or unsubstituted heterocyclyl group $C_{3-9}$ or a substituted or unsubstituted heteroaryl radical $C_{3-9}$;

In another preferred embodiment of the invention $R_5$, $R_6$ and $R_7$ independently represent a hydrogen atom;
a branched or unbranched, saturated or unsaturated, optionally at least mono-substituted, aliphatic radical $C_{1-10}$;
a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;
a substituted or unsubstituted aryl radical; a substituted or unsubstituted, branched or unbranched arylalkyl radical $C_{1-10}$ or at least mono-substituted benzhydryl group;
a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;
a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system.

In a more particular and preferred embodiment of the invention $R_1$ and $R_2$ independently represent hydrogen atom; a branched or unbranched, saturated or unsaturated, optionally at least mono-substituted, aliphatic radical $C_{1-10}$;

or where $R_1$ and $R_2$ together with the bridging nitrogen form an optionally at least monosubstituted group selected from:

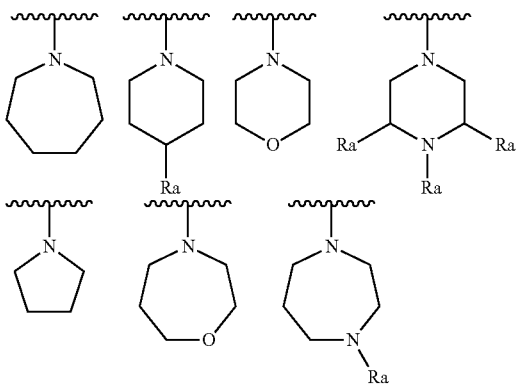

where $R_a$ independently represents a hydrogen, a branched or unbranched, saturated or unsaturated, optionally at least mono-substituted, aliphatic radical $C_{1-10}$ or a (C=O)R' group where R' represents a linear or branched $C_{1-6}$-alkyl group.

In another more particular and preferred embodiment of the invention $R_3$ and $R_4$ independently represent a hydrogen atom; or an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; or $R_3$ and $R_4$ together with the bridging nitrogen form a group selected from:

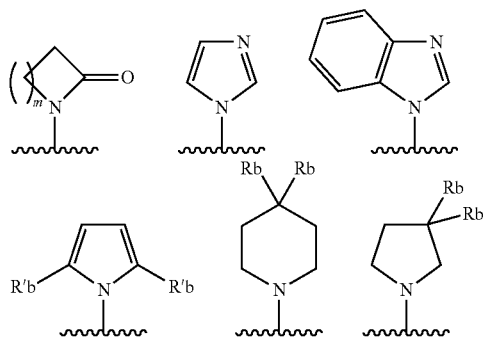

where $R_b$ independently represents a hydrogen, a halogen atom, a phenyl group, a branched or unbranched, saturated or unsaturated, optionally at least mono-substituted, aliphatic radical $C_{1-10}$ or a (C=O)R' group where R' represents a linear or branched $C_{1-6}$-alkyl group; $R'_b$ is a branched or unbranched, saturated or unsaturated, optionally at least mono-substituted, aliphatic radical $C_{1-10}$ and m represents 1, 2, 3 or 4.

Another more particular and preferred embodiment of the invention is illustrated when $R_5$, $R_6$ and $R_7$ independently represent a hydrogen atom; a branched or unbranched, saturated or unsaturated, optionally at least mono-substituted, aliphatic radical $C_{1-10}$; or an optionally at least mono-substituted group selected from:

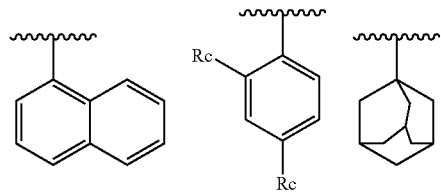

-continued

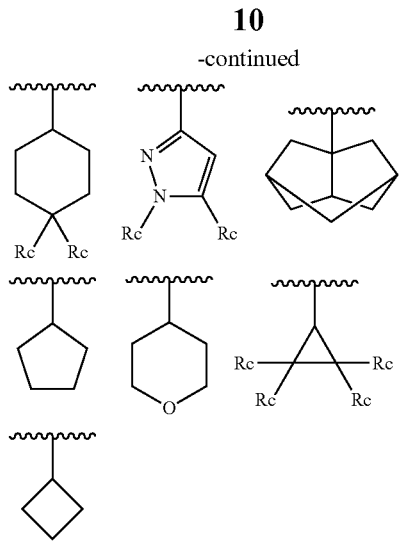

where $R_c$ independently represents a hydrogen, a halogen atom, an —OH or a branched or unbranched, saturated or unsaturated, optionally at least mono-substituted, aliphatic radical $C_{1-10}$.

The more preferred embodiment of the invention is when $R_1$ and $R_2$ independently represent hydrogen atom; a branched or unbranched, saturated or unsaturated, optionally at least mono-substituted, aliphatic radical $C_{1-10}$; or where $R_1$ and $R_2$ together with the bridging nitrogen form an optionally at least mono-substituted group selected from:

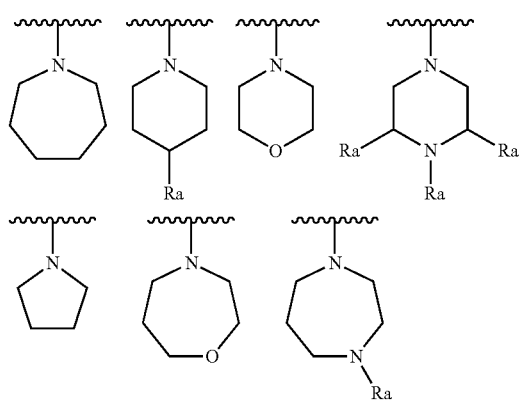

$R_a$ independently representing a hydrogen, a branched or unbranched, saturated or unsaturated, optionally at least mono-substituted, aliphatic radical $C_{1-10}$ or a (C=O)R' group where R' represents a linear or branched $C_{1-6}$-alkyl group;

$R_3$ and $R_4$ independently represent a hydrogen atom; or an —$COR_5$; —$C(O)NR_5R_6$; —$C(S)NR_5R_6$ or —$SO_2R_7$; or $R_3$ and $R_4$ together with the bridging nitrogen form a group selected from:

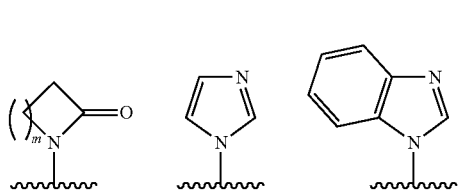

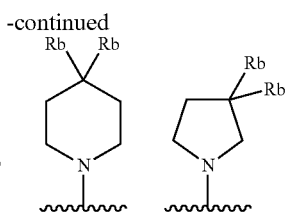

where $R_b$ independently represents a hydrogen, a halogen atom, a phenyl group, a branched or unbranched, saturated or unsaturated, optionally at least mono-substituted, aliphatic radical $C_{1-10}$ or a —NHR' group where R' represents a a linear or branched $C_{1-6}$-alkyl group; $R'_b$ is a branched or unbranched, saturated or unsaturated, optionally at least mono-substituted, aliphatic radical $C_{1-10}$ and m represents 1, 2, 3 or 4.

$R_5$, $R_6$ and $R_7$ independently represent a hydrogen atom; a branched or unbranched, saturated or unsaturated, optionally at least mono-substituted, aliphatic radical $C_{1-10}$; or an optionally at least mono-substituted group selected from:

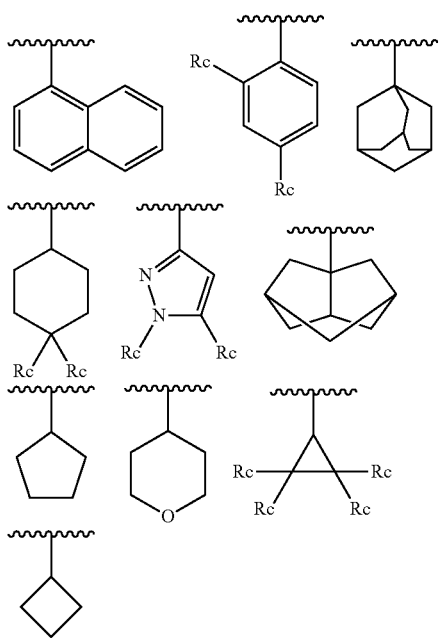

$R_c$ independently representing a hydrogen, a halogen atom, an —OH or a branched or unbranched, saturated or unsaturated, optionally at least mono-substituted, aliphatic radical $C_{1-10}$;

and n is selected from 1, 2, 3 or 4.

The compounds of the present invention represented by the above described formula (I) may include enantiomers depending on the presence of chiral centres or isomers depending on the presence of double bonds (e.g. Z, E). The single isomers, enantiomers or diastereoisomers and mixtures thereof fall within the scope of the present invention.

The compounds obtained according to the invention may, if desired, be purified by conventional methods, such as crystallisation and chromatography. Where the preparation of compounds of the invention, give rise mixtures of stereoisomers, these isomers may be separated by conventional techniques such as preparative chromatography. If there are chiral centers the compounds may be prepared in racemic form, or individual enantiomers may be prepared either by enantiospecific synthesis or by resolution.

One preferred pharmaceutically acceptable form is the crystalline form, including such form in pharmaceutical composition. In the case of salts and solvates the additional ionic and solvent moieties must also be non-toxic. The compounds of the invention may present different polymorphic forms, it is intended that the invention encompasses all such forms.

Among all the compounds encompassed by the general formula (I) the following compounds are particularly preferred:

N-(1-(2-(azepan-1-yl)ethyl)-1H-pyrazolo[3,4-d]pyrimidin-4-yl)pivalamide maleate

N-(1-(2-(piperidin-1-yl)ethyl)-1H-pyrazolo[3,4-d]pyrimidin-4-yl)-1-naphthamide 2-fluoro-N-(1-(2-(piperidin-1-yl)ethyl)-1H-pyrazolo[3,4-d]pyrimidin-4-yl)benzamide N-(1-[2-(Piperidin-1-yl)ethyl]-1H-pyrazolo[3,4-d]pyrimidin-4-yl)-1-adamantyl carboxamide maleate N-(1-(2-(Piperidin-1-yl)ethyl)-1H-pyrazolo[3,4-d]pyrimidin-4-yl)pivalamide maleate N-(1-(2-(Piperidin-1-yl)ethyl)-1H-pyrazolo[3,4-d]pyrimidin-4-yl)cyclohexane carboxamide hydrochloride 2,4-Dichloro-N-(1-(2-(piperidin-1-yl)ethyl)-1H-pyrazolo[3,4-d]pyrimidin-4-yl)benzamide hydrochloride 1,5-dimethyl-N-(1-(2-(piperidin-1-yl)ethyl)-1H-pyrazolo[3,4-d]pyrimidin-4-yl)-1H-pyrazole-3-carboxamide hydrochloride 3,5-di-tert-Butyl-N-(1-(2-(piperidin-1-yl)ethyl)-1H-pyrazolo[3,4-d]pyrimidin-4-yl)benzamide hydrochloride 2-hydroxy-N-(1-(2-(piperidin-1-yl)ethyl)-1H-pyrazolo[3,4-d]pyrimidin-4-yl)benzamide hydrochloride N-(1-(2-(piperidin-1-yl)ethyl)-1H-pyrazolo[3,4-d]pyrimidin-4-yl)(1-noradamantyl carboxamide) maleate N-(1-(2-Morpholinoethyl)-1H-pyrazolo[3,4-d]pyrimidin-4-yl)pivalamide hydrochloride N-(1-(2-(Diisopropylamino)ethyl)-1H-pyrazolo[3,4-d]pyrimidin-4-yl)pivalamide hydrochloride N-(1-(2-Morpholinoethyl)-1H-pyrazolo[3,4-d]pyrimidin-4-yl)cyclohexane carboxamide hydrochloride N-(1-(2-(Azepan-1-yl)ethyl)-1H-pyrazolo[3,4-d]pyrimidin-4-yl)cyclohexane carboxamide maleate N-(1-(2-(Diisopropylamino)ethyl)-1H-pyrazolo[3,4-d]pyrimidin-4-yl)cyclohexane carboxamide maleate N-(1-[2-(Morpholinoethyl]-1H-pyrazolo[3,4-d]pyrimidin-4-yl)-1-adamantyl carboxamide hydrochloride N-(1-(2-(Diisopropylamino)ethyl)-1H-pyrazolo[3,4-d]pyrimidin-4-yl)-1-adamantyl carboxamide maleate N-(1-(2-(Azepan-1-yl)ethyl)-1H-pyrazolo[3,4-d]pyrimidin-4-yl) 1-adamantyl carboxamide hydrochloride N-(1-[2-(Morpholinoethyl]-1H-pyrazolo[3,4-d]pyrimidin-4-yl)-1-noradamantyl carboxamide hydrochloride N-(1-(2-(Diisopropylamino)ethyl)-1H-pyrazolo[3,4-d]pyrimidin-4-yl)-1-noradamantylcarboxamide hydrochloride N-(1-(2-(Azepan-1-yl)ethyl)-1H-pyrazolo[3,4-d]pyrimidin-4-yl) 1-noradamantyl carboxamide hydrochloride 2,4-Dichloro-N-(1-(2-(diisopropylamino)ethyl)-1H-pyrazolo[3,4-d]pyrimidin-4-yl)benzamide hydrochloride N-(1-(2-(Azepan-1-yl)ethyl)-1H-pyrazolo[3,4-d]pyrimidin-4-yl)-2,4-dichloro benzamide hydrochloride 2,4-Dichloro-N-(1-(2-morpholinoethyl)-1H-pyrazolo[3,4-d]pyrimidin-4-yl)benzamide hydrochloride N-(1-(2-(Azepan-1-yl)ethyl)-1H-pyrazolo[3,4-d]pyrimidin-4-yl)tetrahydro-2H-pyran-4-carboxamide hydrochloride N-(1-(2-(Diisopropylamino)ethyl)-1H-pyrazolo[3,4-d]pyrimidin-4-yl)tetrahydro-2H-pyran-4-carboxamide hydrochloride N-(1-(2-(Diisopropylamino)ethyl)-1H-pyrazolo[3,4-d]pyrimidin-4-yl)cyclopentane carboxamide maleate N-(1-(2-(azepan-1-yl)ethyl)-1H-pyrazolo[3,4-d]pyrimidin-4-yl)cyclopentane carboxamide maleate N-(1-(2-(4-isopropylpiperazin-1-yl)ethyl)-1H-pyrazolo[3,4-d]pyrimidin-4-yl) pivalamide maleate N-(1-(2-(4-isopropylpiperazin-1-yl)ethyl)-1H-pyrazolo[3,4-d]pyrimidin-4-yl) 1-adamantylcarboxamide maleate N-(1-(2-(4-isopropylpiperazin-1-yl)ethyl)-1H-pyrazolo[3,4-d]pyrimidin-4-yl)cyclopentanecarboxamide maleate 4-fluoro-N-(1-(2-(4-isopropylpiperazin-1-yl)ethyl)-1H-pyrazolo[3,4-d]pyrimidin-4-yl)benzamide maleate N-(1-(2-(azepan-1-yl)ethyl)-1H-pyrazolo[3,4-d]pyrimidin-4-yl)-4-fluorobenzamide citrate N-(1-(2-(azepan-1-yl)ethyl)-1H-pyrazolo[3,4-d]pyrimidin-4-yl)-2,2,3,3-tetramethyl cyclopropanecarboxamide citrate N-(1-(2-(azepan-1-yl)ethyl)-1H-pyrazolo[3,4-d]pyrimidin-4-yl)-4,4-difluoro cyclohexanecarboxamide maleate N-(1-(2-(pyrrolidin-1-yl)ethyl)-1H-pyrazolo[3,4-d]pyrimidin-4-yl)cyclobutane carboxamide maleate N-(1-(2-(pyrrolidin-1-yl)ethyl)-1H-pyrazolo[3,4-d]pyrimidin-4-yl)cyclohexane carboxamide maleate N-(1-(2-(pyrrolidin-1-yl)ethyl)-1H-pyrazolo[3,4-d]pyrimidin-4-yl)cyclopentane carboxamide maleate N-(1-(2-(pyrrolidin-1-yl)ethyl)-1H-pyrazolo[3,4-d]pyrimidin-4-yl)cyclopropane carboxamide maleate N-(1-(4-(azepan-1-yl)butyl)-1H-pyrazolo[3,4-d]pyrimidin-4-yl)pivalamide maleate N-(1-(3-(azepan-1-yl)propyl)-1H-pyrazolo[3,4-d]pyrimidin-4-yl)pivalamide maleate N-(1-(2-((3S,5R)-3,5-dimethylpiperazin-1-yl)ethyl)-1H-pyrazolo[3,4-d]pyrimidin-4-yl)pivalamide 1-(1-(2-(1,4-oxazepan-4-yl)ethyl)-1H-pyrazolo[3,4-d]pyrimidin-4-yl)-3-propylurea 1-tert-Butyl-3-(1-(2-morpholinoethyl)-1H-pyrazolo[3,4-d]pyrimidin-4-yl)urea hydrochloride 1-Cyclohexyl-3-(1-(2-morpholinoethyl)-1H-pyrazolo[3,4-d]pyrimidin-4-yl)urea hydrochloride 1-Adamanthyl-3-(1-(2-morpholinoethyl)-1H-pyrazolo[3,4-d]pyrimidin-4-yl)urea hydrochloride 1-(1-(2-(Azepan-1-yl)ethyl)-1H-pyrazolo[3,4-d]pyrimidin-4-yl)-3-ethylurea hydrochloride 1-(1-(2-(Azepan-1-yl)ethyl)-1H-pyrazolo[3,4-d]pyrimidin-4-yl)-3-cyclopentylurea hydrochloride 1-(2,4-Dichlorophenyl)-3-(1-(2-morpholinoethyl)-1H-pyrazolo[3,4-d]pyrimidin-4-yl)urea hydrochloride 1-(1-(2-(Azepan-1-yl)ethyl)-1H-pyrazolo[3,4-d]pyrimidin-4-yl)-3-cyclohexylurea hydrochloride 1-(1-(2-(Diisopropylamino)ethyl)-1H-pyrazolo[3,4-d]pyrimidin-4-yl)-3-ethylurea hydrochloride 1-Cyclopentyl-3-(1-(2-(diisopropylamino)ethyl)-1H-pyrazolo[3,4-d]pyrimidin-4-yl)urea hydrochloride 1-Cyclopentyl-3-(1-(2-(piperidin-1-yl)ethyl)-1H-pyrazolo[3,4-d]pyrimidin-4-yl)urea hydrochloride 1-Ethyl-3-(1-(2-(piperidin-1-yl)ethyl)-1H-pyrazolo[3,4-d]pyrimidin-4-yl)urea hydrochloride 1-Adamanthyl-3-(1-(2-(piperidin-1-yl)ethyl)-1H-pyrazolo[3,4-d]pyrimidin-4-yl) urea hydrochloride 1-Cyclohexyl-3-(1-(2-(diisopropylamino)ethyl)-1H-pyrazolo[3,4-d]pyrimidin-4-yl) urea hydrochloride 1-(2,4-Dichlorophenyl)-3-(1-(2-(diisopropylamino)ethyl)-1H-pyrazolo[3,4-d]pyrimidin-4-yl)urea hydrochloride 1-Cyclohexyl-3-(1-(2-(piperidin-1-yl)ethyl)-1H-pyrazolo[3,4-d]pyrimidin-4-yl)urea hydrochloride 1-(2,4-Dichlorophenyl)-3-(1-(2-(piperidin-1-yl)ethyl)-1H-pyrazolo[3,4-d]pyrimidin-4-yl)urea hydrochloride 1-tert-Butyl-3-(1-(2-(diisopropylamino)ethyl)-1H-pyrazolo[3,4-d]pyrimidin-4-yl) urea hydrochloride 1-(1-(2-(azepan-1-yl)ethyl)-1H-pyrazolo[3,4-d]pyrimidin-4-yl)-3-tert-butylurea hydrochloride 1-Adamanthyl-3-(1-(2-(azepan-1-yl)ethyl)-1H-pyrazolo[3,4-d]pyrimidin-4-yl)urea maleate 1-(1-(2-(azepan-1-yl)ethyl)-1H-pyrazolo[3,4-d]pyrimidin-4-yl)-3-(2,4-dichloro phenyl)urea citrate 1-(1-(2-(azepan-1-yl)ethyl)-1H-pyrazolo[3,4-d]pyrimidin-4-yl)-3-(2,4,4-trimethylpentan-2-yl)urea maleate 1-(1-(2-(azepan-1-yl)ethyl)-1H-pyrazolo[3,4-d]pyrimidin-4-yl)-3-propylurea maleate 1-(1-(2-(azepan-1-yl)ethyl)-1H-pyrazolo[3,4-d]pyrimidin-4-yl)-3-butylurea hydrochloride 1-(1-(2-(azepan-1-yl)ethyl)-1H-pyrazolo[3,4-d]pyrimidin-4-yl)-3-cyclopropylurea hydrochloride 1-(1-(2-(azepan-1-yl)ethyl)-1H-pyrazolo[3,4-d]pyrimidin-4-yl)-3-isopropylurea hydrochloride 1-isopropyl-3-(1-(2-(pyrrolidin-1-yl)ethyl)-1H-pyrazolo[3,4-d]pyrimidin-4-yl)urea hydrochloride 1-propyl-3-(1-(2-(pyrrolidin-1-yl)ethyl)-1H-pyrazolo[3,4-d]pyrimidin-4-yl)urea hydrochloride 1-(1-(4-(azepan-1-yl)butyl)-1H-pyrazolo[3,4-d]pyrimidin-4-yl)-3-propylurea maleate 1-(1-(3-(azepan-1-yl)propyl)-1H-pyrazolo[3,4-d]pyrimidin-4-yl)-3-propylurea 1-(1-(2-(4-tert-butylpiperidin-1-yl)ethyl)-1H-pyrazolo[3,4-d]pyrimidin-4-yl)-3-propylurea 1-(1-(2-(azepan-1-yl)ethyl)-1H-pyrazolo[3,4-d]pyrimidin-4-yl)-3-butylthiourea maleate 1-(1-(2-(azepan-1-yl)ethyl)-1H-pyrazolo[3,4-d]pyrimidin-4-yl)-3-methylthiourea maleate 1-(1-(2-(azepan-1-yl)ethyl)-1H-pyrazolo[3,4-d]pyrimidin-4-yl)-3-propylthiourea 1-(1-(2-(azepan-1-yl)ethyl)-1H-pyrazolo[3,4-d]pyrimidin-4-yl)-3-ethylthiourea 1-(1-(2-(azepan-1-yl)ethyl)-1H-pyrazolo[3,4-d]pyrimidin-4-yl)-3-cyclopropyl thiourea hydrochloride 2,4-Dichloro-N-(1-(2-(diisopropylamino)ethyl)-1H-pyrazolo[3,4-d]pyrimidin-4-yl)benzenesulfonamide hydrochloride N-(1-(2-(Diisopropylamino)ethyl)-1H-pyrazolo[3,4-d]pyrimidin-4-yl)cyclohexane sulfonamide hydrochloride N-(1-(2-(4-tert-butylpiperidin-1-yl)ethyl)-1H-pyrazolo[3,4-d]pyrimidin-4-yl)pivalamide N-(1-(2-(1,4-oxazepan-4-yl)ethyl)-1H-pyrazolo[3,4-d]pyrimidin-4-yl)pivalamide N-(1-(2-(4-methyl-1,4-diazepan-1-yl)ethyl)-1H-pyrazolo[3,4-d]pyrimidin-4-yl)pivalamide N-(1-(3-(piperidin-1-yl)propyl)-1H-pyrazolo[3,4-d]pyrimidin-4-yl)pivalamide N-(1-(3-(4-methylpiperazin-1-yl)propyl)-1H-pyrazolo[3,4-d]pyrimidin-4-yl)pivalamide N-(1-(2-(4-methylpiperazin-1-yl)ethyl)-1H-pyrazolo[3,4-d]pyrimidin-4-yl)pivalamide maleate N-(1-(4-(4-tert-butylpiperidin-1-yl)butyl)-1H-pyrazolo[3,4-d]pyrimidin-4-yl)pivalamide maleate 1-(1-(2-(4-methyl-1,4-diazepan-1-yl)ethyl)-1H-pyrazolo[3,4-d]pyrimidin-4-yl)-3-propylurea 1-(1-(3-(4-methylpiperazin-1-yl)propyl)-1H-pyrazolo[3,4-d]pyrimidin-4-yl)-3-propylurea 1-(1-(3-(piperidin-1-yl)propyl)-1H-pyrazolo[3,4-d]pyrimidin-4-yl)-3-propylurea 1-(1-(2-(4-methylpiperazin-1-yl)ethyl)-1H-pyrazolo[3,4-d]pyrimidin-4-yl)-3-propylurea 1-(1-(4-(4-tert-butylpiperidin-1-yl)butyl)-1H-pyrazolo[3,4-d]pyrimidin-4-yl)-3-propylurea 1-(1-(2-(4-acetylpiperazin-1-yl)ethyl)-1H-pyrazolo[3,4-d]pyrimidin-4-yl)-3-propylurea 1-(1-(2-(piperidin-1-yl)ethyl)-1H-pyrazolo[3,4-d]pyrimidin-4-yl)-3-propylurea 2,4-dichloro-N-(1-(2-(piperidin-1-yl)ethyl)-1H-pyrazolo[3,4-d]pyrimidin-4-yl)benzenesulfonamide N-(1-(2-(piperidin-1-yl)ethyl)-1H-pyrazolo[3,4-d]pyrimidin-4-yl)methanesulfonamide N-(1-(2-(piperidin-1-yl)ethyl)-1H-pyrazolo[3,4-d]pyrimidin-4-yl)propane-2-sulfonamide N-(1-(2-(piperidin-1-yl)ethyl)-1H-pyrazolo[3,4-d]pyrimidin-4-yl)cyclohexanesulfonamide N-(1-(2-(piperidin-1-yl)ethyl)-1H-pyrazolo[3,4-d]pyrimidin-4-yl)ethanesulfonamide N-(1-(2-(azepan-1-yl)ethyl)-1H-pyrazolo[3,4-d]pyrimidin-4-yl)-N-methylacetamide 1-(1-(2-(piperidin-1-yl)ethyl)-1H-pyrazolo[3,4-d]pyrimidin-4-yl)pyrrolidin-2-one 4-(1H-imidazol-1-yl)-1-(2-(piperidin-1-yl)ethyl)-1H-pyrazolo[3,4-d]pyrimidine 4-(1H-benzo[d]imidazol-1-yl)-1-(2-(piperidin-1-yl)ethyl)-1H-pyrazolo[3,4-d]pyrimidine 4-(2,5-dimethyl-1H-pyrrol-1-yl)-1-(2-(piperidin-1-yl)ethyl)-1H-pyrazolo[3,4-d]pyrimidine 4-(4,4-difluoropiperidin-1-yl)-1-(2-(piperidin-1-yl)ethyl)-1H-pyrazolo[3,4-d]pyrimidine 4-(3,3-dimethylpyrrolidin-1-yl)-1-(2-(piperidin-1-yl)ethyl)-1H-pyrazolo[3,4-d]pyrimidine 4-(3-phenylpyrrolidin-1-yl)-1-(2-(piperidin-1-yl)ethyl)-1H-pyrazolo[3,4-d]pyrimidine N-methyl-1-(1-(2-(piperidin-1-yl)ethyl)-1H-pyrazolo[3,4-d]pyrimidin-4-yl)pyrrolidin-3-amine 4-(piperidin-1-yl)-1-(2-(piperidin-1-yl)ethyl)-1H-pyrazolo[3,4-d]pyrimidine A specific embodiment of the invention is that in which the pyrazolo[3,4-d]pyrimidine compounds of the invention are defined by the following general formula (Ia):

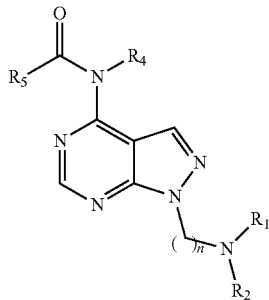

(Ia)

where $R_1$, $R_2$, $R_4$, $R_5$ and n have the same meanings as in formula (I).

Another specific embodiment is that in which pyrazolo[3,4-d]pyrimidine compounds of the invention are defined by general formula (Ib)

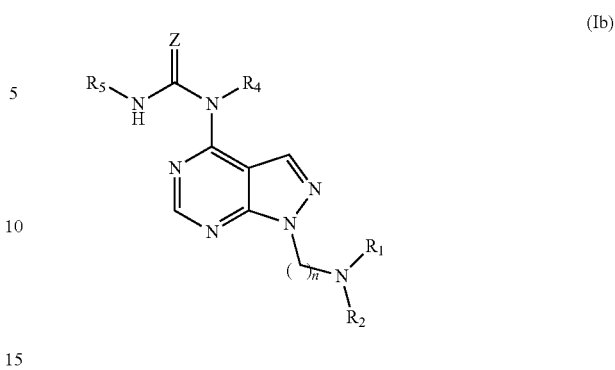

(Ib)

where $R_1$, $R_2$, $R_4$, $R_6$ and n have the same meaning as in formula (I) and Z represents either S or O.

An additional, specific embodiment of the invention is provided where pyrazolo[3,4-d]pyrimidine compounds of the invention are represented by general formula (Ic):

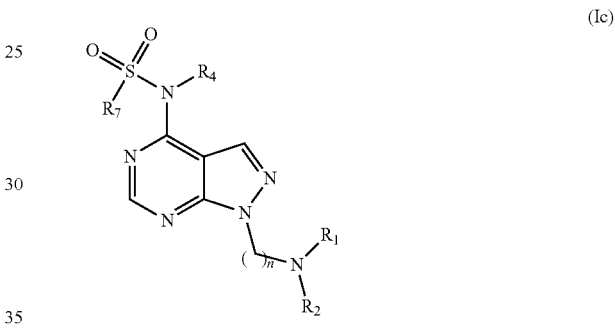

(Ic)

where $R_1$, $R_2$, $R_4$, $R_7$ and n have the same meaning as in formula (I).

A further specific embodiment is that in which pyrazolo[3,4-d]pyrimidine compounds of the invention are defined by general formula (Id):

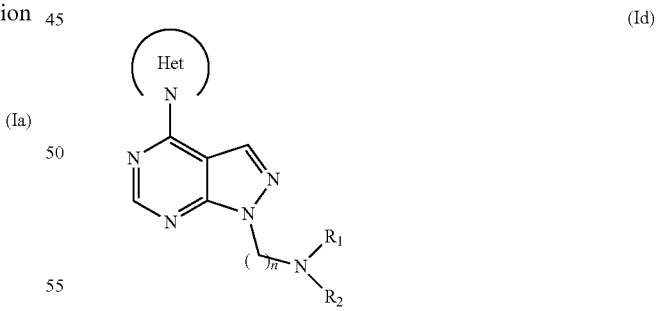

(Id)

where $R_1$, $R_2$ and n have the same meaning as for formula (I) and Het represents with the N a substituted or unsubstituted cycloalkyl radical $C_{3-9}$; a substituted or unsubstituted heterocyclyl group $C_{3-9}$ or a substituted or unsubstituted heteroaryl radical $C_{3-9}$.

In a still more particular embodiment, compounds of general formula (Id') are those compounds of general formula (Id) where Het particularly represents a group selected from:

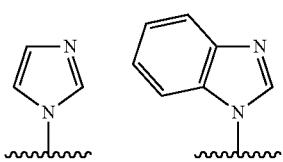

Similarly, in a more particular embodiment compounds of general formula (Id) are designated as compounds of formula (Id") when Het are particularly represented by the following group:

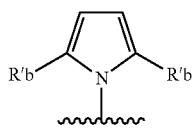

where $R'_b$ is a branched or unbranched, saturated or unsaturated, optionally at least mono-substituted, aliphatic radical $C_{1-10}$.

A further specific embodiment is that in which pyrazolo[3,4-d]pyrimidine compounds of the invention are defined by general formula (Ie):

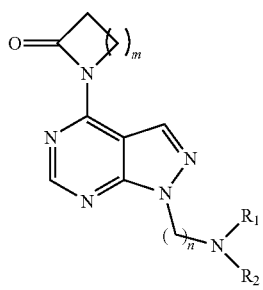

(Ie)

where $R_1$, $R_2$ and n have the same meaning as for formula (I) and m represents 1, 2, 3 or 4.

In another aspect the invention refers to the processes for obtaining the compounds of general formula (I). Several processes have been developed for obtaining all the compounds of the invention. The different processes are explained as methods A to F.

Method A

A process is described for the preparation of a compound of general formula (Ia):

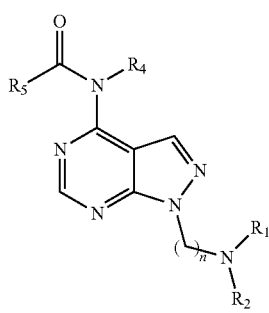

(Ia)

comprising the reaction between a compound of general formula (IX):

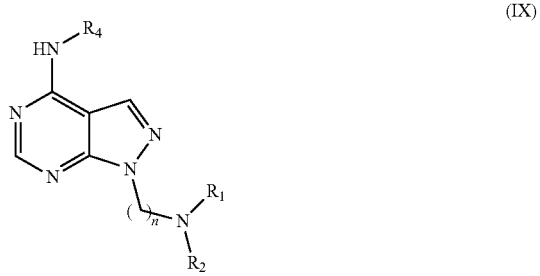

(IX)

with a compound of general formula (X):

(X)

wherein $R_1$, $R_2$, $R_4$, $R_5$ and n have the meanings as in general formula (I) and X is a halogen.

The reaction of compounds of formula (IX) and (X) is preferably carried out at a temperature range of 90-125° C. in an aprotic solvent such as toluene or tetrahydrofuran in the presence of an organic base such as pyridine or DMAP. Alternatively the reaction can be carried out in a microwave reactor.

Method B

The process for the synthesis of compounds of formula (Ib):

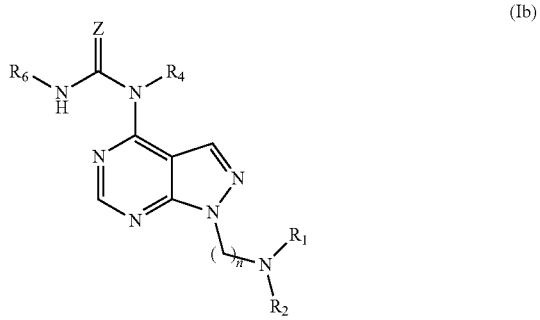

(Ib)

comprises the reaction between a compound of general formula (IX):

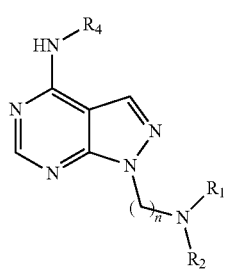

(IX)

with a compound of general formula (XI):

   (XI)

where $R_1$, $R_2$, $R_6$ and n have the meanings as in general formula (I) and Z represents O or S.

The reaction of compounds of formula (IX) and (XI) is preferably carried out in an aprotic solvent such as toluene or acetonitrile at a temperature range of 50-120° C. Alternatively, the reaction can be carried out in a microwave reactor.

Method C

The method for the synthesis of compounds of general formula (Ic):

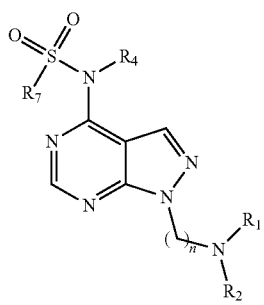   (Ic)

comprises the reaction between a compound of general formula (IX):

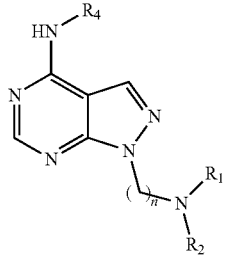   (IX)

with a compound of general formula (XII):

   (XII)

where $R_1$, $R_2$, $R_7$ and n have the meanings as in general formula (I) and X represents a halogen.

The reaction of compounds of formula (IX) and (XII) is preferably carried out at a temperature range of 50-125° C. in an aprotic solvent such as toluene or tetrahydrofuran in the presence of an organic base such as pyridine or DMAP. Alternatively, the reaction can be carried out in a microwave reactor.

Method D

The process for the synthesis of compounds of formula (Id):

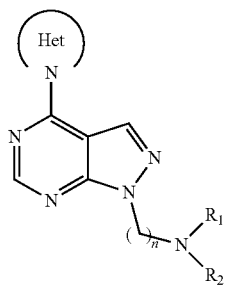   (Id)

comprises de reaction between a compound of general formula (XIV):

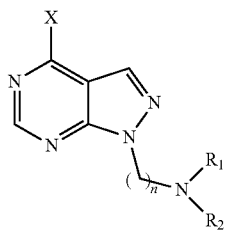   (XIV)

with an heterocyclic compound of formula (XVI):

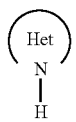   (XVI)

where $R_1$, $R_2$, and n have the meanings as in general formula (I) and X is a halogen.

The reaction of compounds of formula (XIV) and heterocycles (XVI) is preferably carried out at a temperature range of 0° C. and the boiling point of an aprotic solvent such as THF, DMF or pyridine in the presence of a base such as sodium hydride or potassium tert-butoxide. These conditions are specially suited for preparing compounds of general formula (Id') as defined above, that is for compounds where Het represents an imidazole-like compound.

Compounds of formula (Id"):

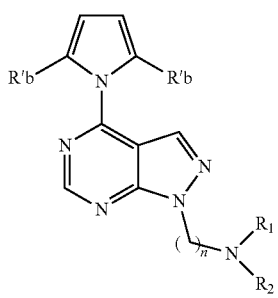   (Id")

can be prepared by reaction of a compound of formula (VII):

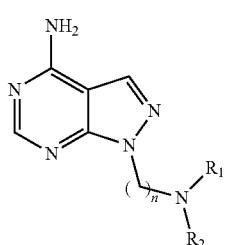   (VII)

with a 1,4-dione of formula (XIX):

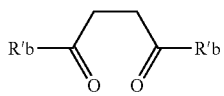   (XIX)

where $R_1$, $R_2$ and n has the same meanings as for formula (I) and $R'_b$ is a branched or unbranched, saturated or unsaturated, optionally at least mono-substituted, aliphatic radical $C_{1-10}$.

The reaction of compounds of formula (VII) and 1,4-diones (XIX) are preferably carried out without a solvent or in presence of an acid such as acetic acid at a temperature of 140-160° C. Alternatively, the reaction can be carried out in a microwave reactor.

Method E

The process for the synthesis of compounds of formula (I):

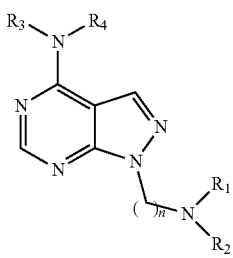
(I)

comprising the reaction between a compound of general formula (XIV):

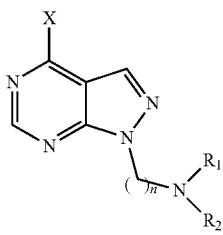
(XIV)

with amines of formula $R_3R_4NH$ (XVIII)

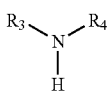
(XVIII)

where $R_1$, $R_2$ $R_3$, $R_4$, and n have the meanings as in general formula (I) and X is a halogen.

The reaction of compounds of formula (XIV) and amines (XVIII) is preferably carried out at a temperature range of 0° C. and the boiling point of a solvent such as methanol, ethanol, THF, DMF.

Method F

The process for the synthesis of compounds of formula (Ie):

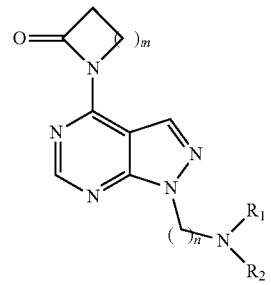
(Ie)

comprises de reaction between a compound of general formula (XIV):

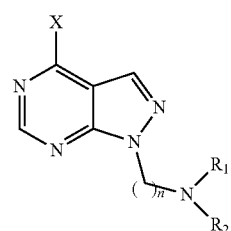
(XIV)

with a compound of formula general (XVII)

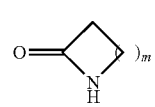
(XVII)

where $R_1$, $R_2$, and n have the meanings as in general formula (I) and m is selected from 1, 2, 3 or 4 and X is a halogen.

The reaction of compounds of formula (XIV) and (XVII) is preferably carried out under catalytic conditions, with catalysis such as palladium diacetate, tris(dibenzylideneacetone)dipalladium(0) or tris(dibenzylideneacetone)dipalladium(0) chloroform complex in the presence of ligands such as xantphos, in the presence of base such as caesium carbonate or potassium phosphate and in solvents such as toluene o 1,4-dioxane at a temperature range of 50° C. and the boiling point of the solvent or in a microwave reactor.

A general synthetic route describing methods A to C is shown in the following scheme 1:

Scheme 1

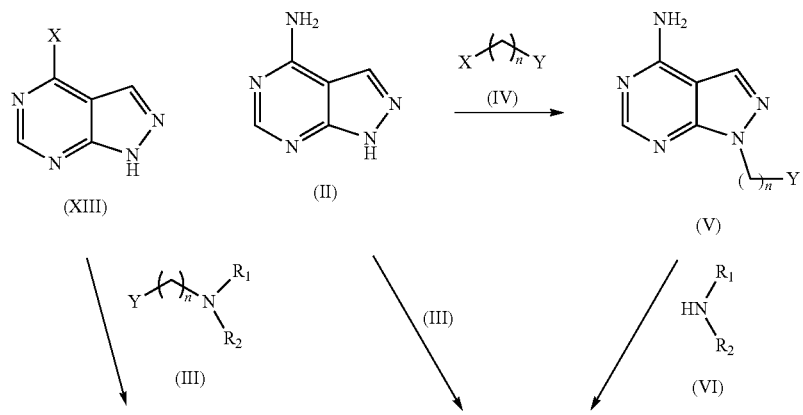

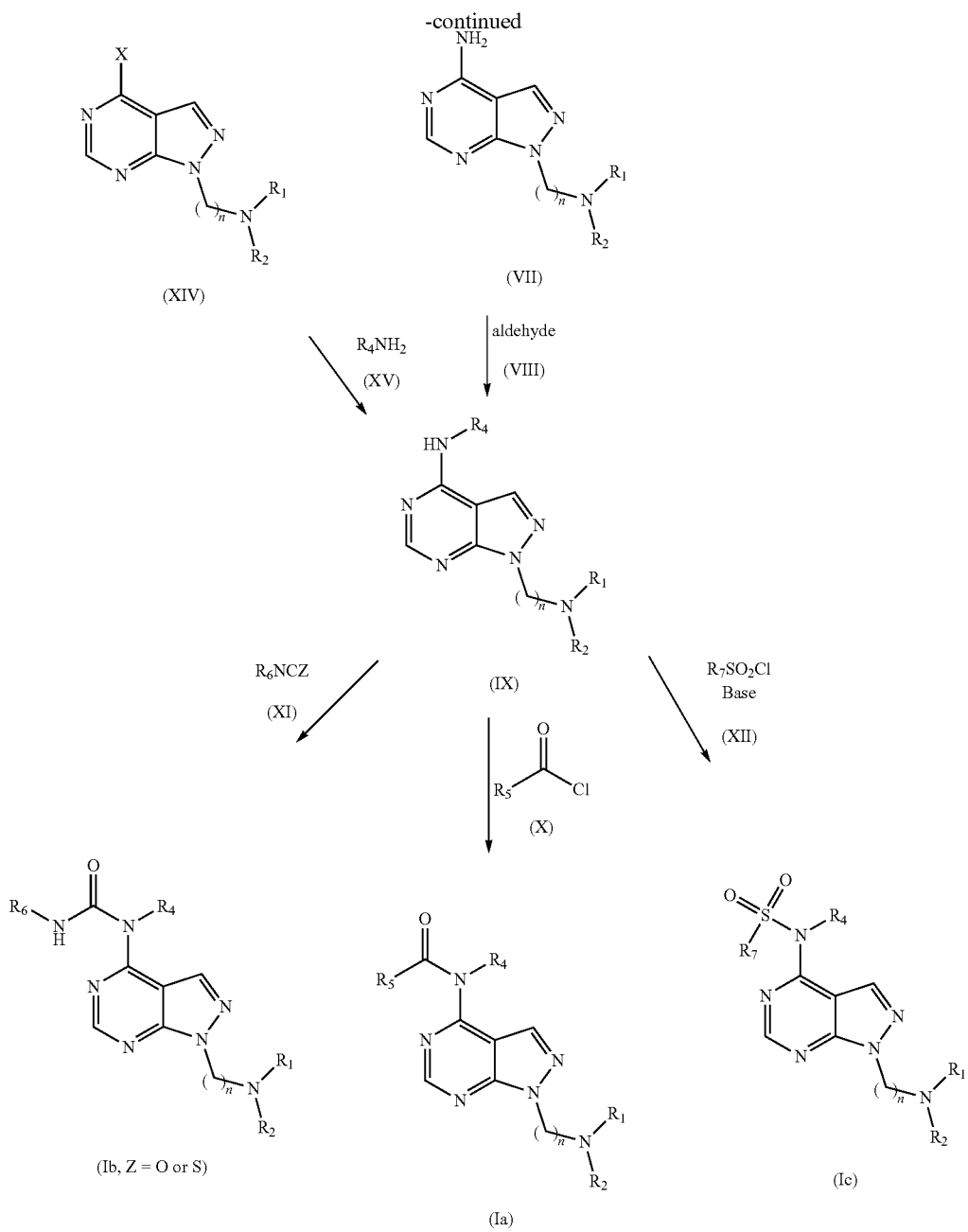

compound (VII) corresponds to specific embodiment of general formula (I) wherein $R_3$ and $R_4$ are H.

As observed in scheme 1 all three methods A to C are carried out by reaction of the same starting material, namely compound (IX). Compound (IX) can be obtained by reductive amination of a compound of formula (VII) with an aldehyde (VIII). The type of aldehyde to be used will depend on the meaning of the final substituent $R_4$. For instance, if $R_4$ is intended to represent a methyl group formaldehyde should be used, if an ethyl group is desired in position $R_4$ acetaldehyde should be used etc.

Compounds of formula (VII) can be prepared by two different processes. In a first process they are prepared by reaction between compounds of formula (II) with a compound of formula (III) where Y is a suitable leaving group such as a halogen or a hydroxyl group. When Y is a halogen the reaction is preferably carried out in an aprotic solvent such as dimethylformamide (DMF) in the presence of an inorganic base such as NaH. When Y is a hydroxyl group the reaction is performed under Mitsunobu conditions.

A second process for the preparation of compounds of formula (VII) comprises the reaction between a compound of formula (V) where Y is a suitable leaving group such as a halogen, with an amine of formula (VI). The reaction between compounds of formula (V) and (VI) is preferably carried out in an aprotic solvent such as dimethylformamide (DMF) in the presence of an inorganic base, preferably $K_2CO_3$. An activating agent as NaI can be used.

All compounds (II), (III) and (VI) are commercially available. Alternatively compound of formula (II) can be obtained by methods described in bibliography [WO2007126841; R. K. Robins, *J. Am. Chem. Soc.* 784-790 (1956); S. Grupta et al., *Eur. J. Med. Chem.*, 771-780 (2008)] and compounds of formula (III) and (VI) can be obtained by conventional methods. In turn, compounds of general formula (V) can be prepared by the reaction of compounds II with compounds of formula (IV) where X and Y are suitable different leaving groups. The reaction of compounds of formula (II) and (IV) is preferably carried out in an aprotic solvent, but no limited to, such as dimethylformamide (DMF) in the presence of an inorganic base, such as NaH.

Alternatively, the starting material of methods A, B and C, namely compound (IX) can be obtained through the reaction of a compound of general formula (XIV) with a compound of formula (XV). This reaction is preferably carried out in an aprotic solvent such as DMF or in a protic solvent such as ethanol at a temperature range from 0° C. to solvent boiling point. Compounds of formula (XIV) can be prepared by reaction between compounds of formula (XIII) with a compound of formula (III) where Y is a suitable leaving group such as a halogen. This reaction is preferably carried out in an aprotic solvent such as dimethylformamide (DMF) in the presence of an inorganic base such as NaH. Compounds of formula (XIII) are commercially available.

Compounds of general formula (Ia), (Ib) and (Ic) where $R_4$ is Hydrogen [referred under the scheme below as (Ia'), (Ib') and (Ic')] can be prepared by the direct reaction of intermediate (VII) with compounds (X), (XI) and (XII) respectively. The synthetic routes for the preparation of compounds (Ia'), (Ib') and (Ic') where $R_4$ is Hydrogen is represented in the following scheme 2:

Scheme 2

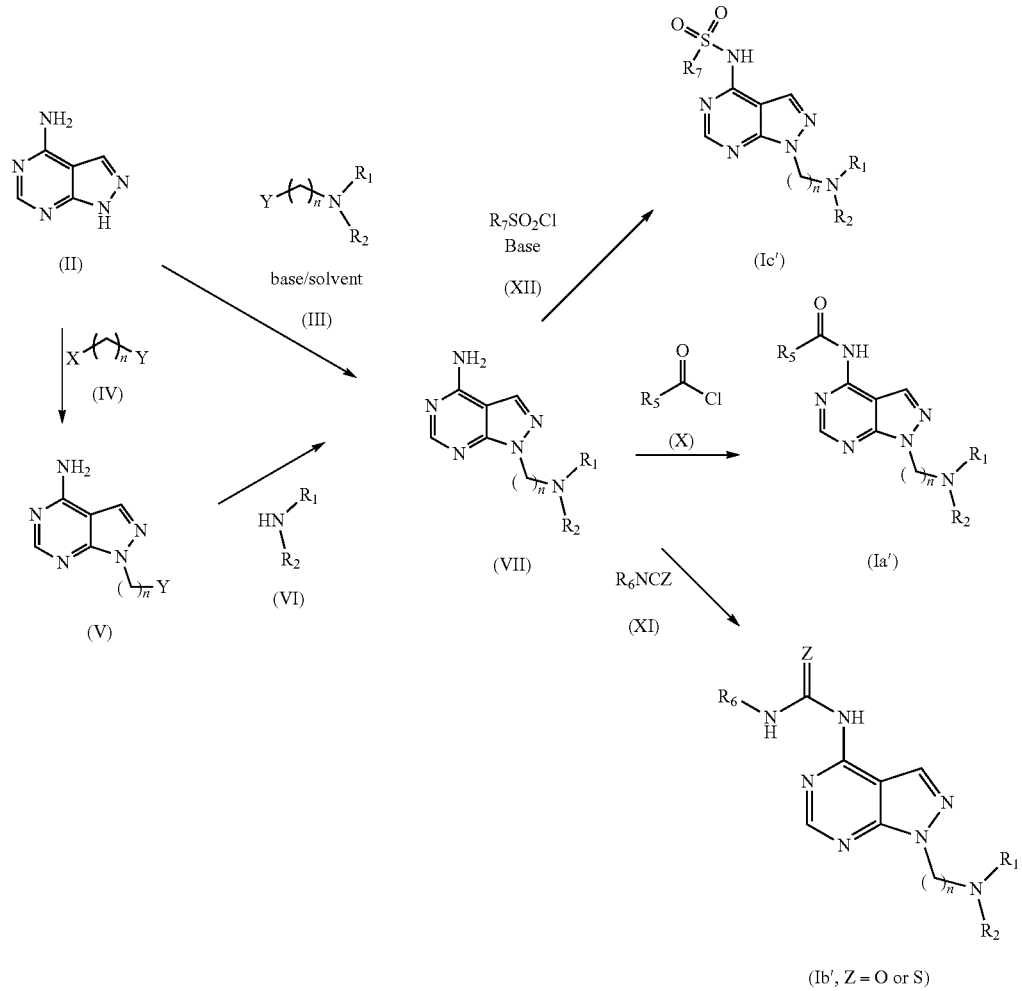

The reaction of compounds of formula (VII) and (X) is preferably carried out at a temperature range of 90-125° C. in an aprotic solvent such as toluene of tetrahydrofuran in the presence of an organic base such as pyridine or DMAP. Alternatively the reaction can be carried out in a microwave reactor.

Compounds of formula (Ib') can be prepared by reaction of a compound of formula (VII) with a compound of formula (XI) in which $R_6$ is as defined above. Compounds of formula (XI) are commercially available.

The reaction of compounds of formula (VII) and (XI) is preferably carried out in an aprotic solvent such as toluene or acetonitrile at a temperature range of 50-120° C. Alternatively, the reaction can be carried out in a microwave reactor.

Compounds of formula (Ic') can be prepared by reaction of a compound of formula (VII) with a compound of formula (XII) in which $R_7$ is as defined above. Compounds of formula (XII) are commercially available.

The reaction of compounds of formula (VII) and (XII) is preferably carried out at a temperature range of 50-125° C. in an aprotic solvent such as toluene of tetrahydrofuran in the presence of an organic base such as pyridine or DMAP. Alternatively, the reaction can be carried out in a microwave reactor.

The synthetic routes for the preparation of compounds (Id'), (I) and (Ie) according to methods D, E and F are depicted in the following scheme 3:

As observed in scheme 3 all three methods D to F are carried out by reaction of the same starting material, namely compound (XIV). Compound (XIV) can be prepared by reaction between compounds of formula (XIII) with a compound of formula (III) where Y is a suitable leaving group such as a halogen. This reaction is preferably carried out in an aprotic solvent such as dimethylformamide (DMF) in the presence of an inorganic base such as NaH. Compounds of formula (XIII) are commercially available.

Finally, the synthetic route for the preparation of compounds (Id"), that is, compounds of formula (I) where $R_3$ together with $R_4$ form pyrrolic type moieties according to method F is depicted in the following scheme 4:

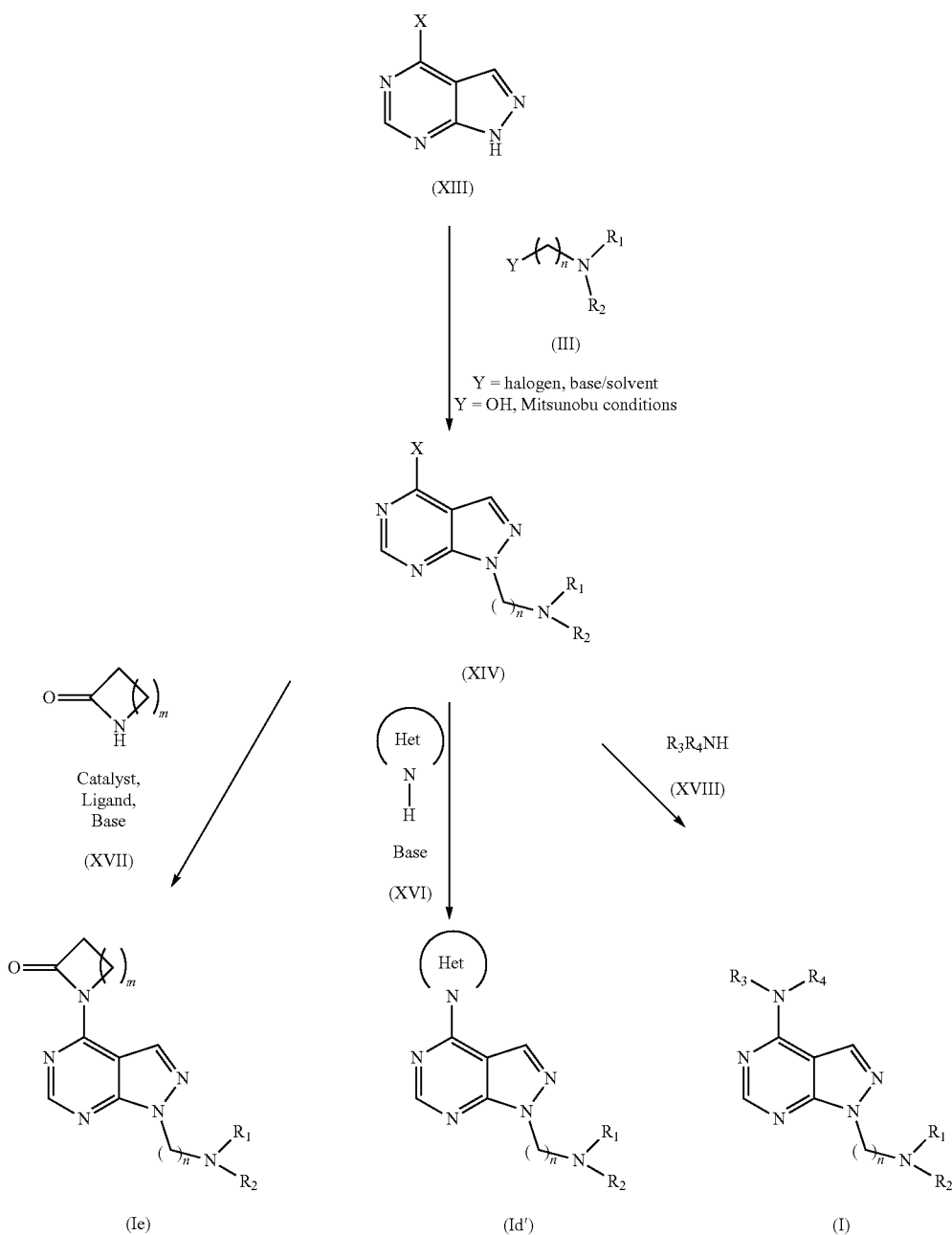

Scheme 4

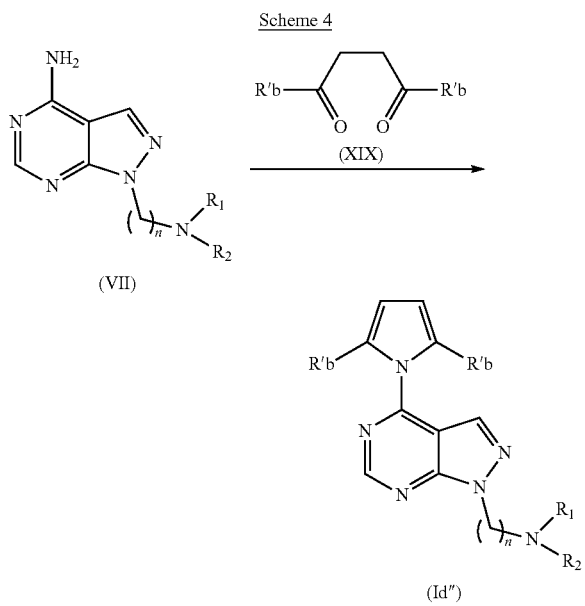

R'b as expressed before independently represents a branched or unbranched, saturated or unsaturated, optionally at least mono-substituted, aliphatic radical $C_{1-10}$.

An additional aspect of the invention relates to the therapeutic use of the compounds of general formula (I). As mentioned above, compounds of general formula (I) show a strong affinity to sigma receptors and can behave as agonists, antagonists, inverse agonists, partial antagonists or partial agonists thereof. For this reason, they are suitable for the treatment and the prophylaxis of disorders and diseases mediated by the sigma receptors, especially, sigma-1 receptor. In this sense, compounds of formula (I) are very good anxiolitic and immunosuppressant and are very useful in the treatment and prophylaxis of diarrhoea, lipoprotein disorders, hyperlipidemia, hypertriglyceridemia, hypercholesterolemia, obesity, migraine, arthritis, hypertension, arrhythmia, ulcer, glaucoma, learning, memory and attention deficits, cognition disorders, neurodegenerative diseases, demyelinating diseases, addiction to drugs and chemical substances including cocaine, amphetamine, ethanol and nicotine; tardive diskinesia, ischemic stroke, epilepsy, stroke, stress, cancer, psychotic conditions, in particular depression, anxiety or schizophrenia; inflammation or autoimmune diseases. The compounds of formula (I) are especially suited for the treatment of pain, especially neuropathic pain, inflammatory pain or other pain conditions involving allodynia and/or hyperalgesia. PAIN is defined by the International Association for the Study of Pain (IASP) as "an unpleasant sensory and emotional experience associated with actual or potential tissue damage, or described in terms of such damage (IASP, Classification of chronic pain, 2nd Edition, IASP Press (2002), 210). Even though pain is always subjective its causes or syndromes can be classified.

Another aspect of the invention is a pharmaceutical composition which comprises a compound of general formula I or a pharmaceutically acceptable salt, prodrug, isomer or solvate thereof, and at least a pharmaceutically acceptable carrier, additive, adjuvant or vehicle.

The auxiliary materials or additives can be selected among carriers, excipients, support materials, lubricants, fillers, solvents, diluents, colorants, flavour conditioners such as sugars, antioxidants and/or agglutinants. In the case of suppositories, this may imply waxes or fatty acid esters or preservatives, emulsifiers and/or carriers for parenteral application. The selection of these auxiliary materials and/or additives and the amounts to be used will depend on the form of application of the pharmaceutical composition.

The pharmaceutical composition in accordance with the invention can be adapted to any form of administration, be it orally or parenterally, for example pulmonarily, nasally, rectally and/or intravenously. Therefore, the formulation in accordance with the invention may be adapted for topical or systemic application, particularly for dermal, subcutaneous, intramuscular, intra-articular, intraperitoneal, pulmonary, buccal, sublingual, nasal, percutaneous, vaginal, oral or parenteral application.

Suitable preparations for oral applications are pills, chewing gums, capsules, granules, drops or syrups.

Suitable preparations for parenteral applications are solutions, suspensions, reconstitutable dry preparations or sprays.

The compounds of the invention as deposits in dissolved form or in patches, for percutaneous application.

Skin applications include ointments, gels, creams, lotions, suspensions or emulsions.

The preferred form of rectal application is by means of suppositories.

The amount of active ingredient that must be administered to the patient depends on the patient's weight, the type of application, the condition and severity of the disease. Normally, in human beings 1 to 500 mg of the active compound is administered daily in one or several doses.

Described below are a number of examples by way of illustration of the invention and do not limit it in anyway.

Examples of Preparation of an Intermediate of Formula (VII)

a) Synthesis of 1-(2-(azepan-1-yl)ethyl)-1H-pyrazolo[3,4-d]pyrimidin-4-amine

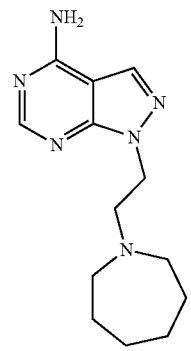 [SMILES: Nc1ncnc2c1cnn2CCN1CCCCCC1]

NaH (60% in mineral oil, 0.547 g, 16.3 mmol) was added over a solution of 4-amino-1H-pyrazolo[3,4-d]pyrimidine (II) (2.0 g, 15.0 mmol) in anhydrous DMF (40 ml). The mixture was stirred at rt for 1 h, and then a solution in anhydrous DMF (2 ml) of 1-(2-chloroethyl)azepane was added (2.39 g, 15.0 mmol) dropwise. The mixture was stirred at rt for 18 h, allowed to cool to rt and poured into an NaHCO$_3$ aq. solution. Diethyl ether was added and the organic phase was separated. The aqueous phase was extracted with diethyl ether, and the combined organic phases were dried over anh. Na$_2$SO$_4$, filtered and concentrated to dryness. The residue was poured into hexane and filtered to yield 1.13 g of 1-(2-(azepan-1-yl)ethyl)-1H-pyrazolo[3,4-d]pyrimidin-4-amine. $^1$H-NMR (DMSO-d$_6$) δ ppm: 8.15 (s, 1H), 8.05 (s, 1H), 7.6 (bs, 2H), 4.3 (t, J=6.7 Hz, 2H), 2.9 (t, J=6.7 Hz, 2H), 2.55 (m, 4H), 1.4 (m, 8H).

b) Synthesis of 1-(2-(4-tert-butylpiperidin-1-yl)ethyl)-1H-pyrazolo[3,4-d]pyrimidin-4-amine

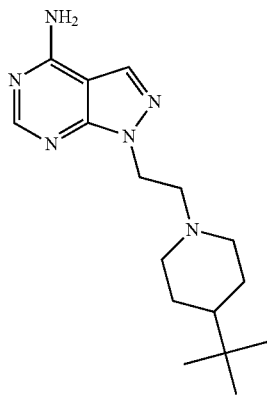 [SMILES: CC(C)(C)C1CCN(CCn2ncc3c(N)ncnc32)CC1]

4-amino-1H-pyrazolo[3,4-d]pyrimidine (II) (1.5 g, 0.011 mol) was added in portions to a suspension of NaH (60% in mineral oil, 0.41 g, 0.012 mol) in 20 ml of anhydrous DMF. After stirring for 2 h at rt, a solution of 1-bromo-2-chlorobutane (1.06 ml, 0.013 mol) in 4 ml of anhydrous DMF was added dropwise. The reaction was stirred at rt for 18 h., cooled at 0° C. and quenched with water. The mixture was concentrated in vacuum, treated with EtOAc and filtered; the solution was concentrated and the crude purified by flash chromatography (gradient from 100% EtOAc to EtOAc/MeOH 9:1) to yield 1.02 g of 1-(2-chloroethyl)-1H-pyrazolo[3,4-d]pyrimidin-4-amine as a white solid.

1-(2-chloroethyl)-1H-pyrazolo[3,4-d]pyrimidin-4-amine (0.250 g, 0.001 mol), 4-tert-butylpiperidine hydrochloride (0.405 g, 0.002 mol), $K_2CO_3$ (0.524 g, 0.004 mol) and a catalytic amount of NaI were stirred in a solution of 10 ml of anhydrous DMF for 16 h at 95° C. Mixture was concentrated under reduced pressure, treated with EtOAc and filtered. The solution was evaporated to dryness and the residue treated with petroleum ether and decanted to yield 0.225 g of a white solid.

Examples of Preparation of Compounds of General Formula (I)

Example 1

Synthesis of N-(1-(2-(azepan-1-yl)ethyl)-1H-pyrazolo[3,4-d]pyrimidin-4-yl)pivalamide maleate

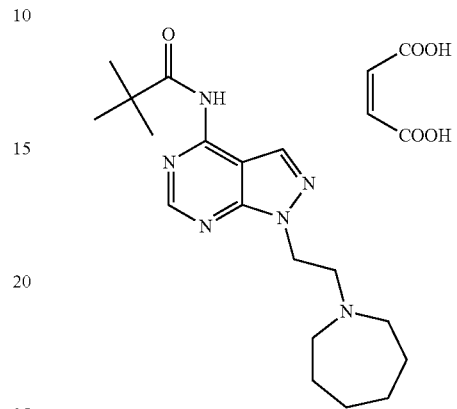

1-(2-(Azepan-1-yl)ethyl)-1H-pyrazolo[3,4-d]pyrimidin-4-amine (0.300 g, 1.152 mmol), pivaloyl chloride (0.278 g, 2.30 mmol) in 3 mL of anhydrous pyridine with catalytic DMAP were heated in CEM microwave reactor for 15 minutes at 130° C. The mixture was concentrated under reduced pressure and partitioned in EtOAc and 10% aq. NaOH sol. The organic layers were washed with water, dried and evaporated to dryness. To an ice-cooled stirred solution in 2.5 mL of MeOH, 0.145 g (1.25 mmol) of maleic acid in 1 ml of MeOH was added dropwise. After stirring for 15 minutes at rt, the solvent was removed under vacuum and the residue washed with diethyl ether to obtain 450 mg of N-(1-(2-(Azepan-1-yl)ethyl)-1H-pyrazolo[3,4-d]pyrimidin-4-yl)pivalamide maleate. $^1$H NMR (CD$_3$OD) δ ppm: 8.67 (s, 1H), 8.63 (s, 1H), 6.25 (s, 2H), 4.89 (t, J=5.8 Hz, 2H), 3.80 (t, J=5.9 Hz, 2H), 3.65-3.38 (m, 4H), 2.04-1.86 (m, 4H), 1.81-1.65 (m, 4H), 1.38 (s, 9H).

Examples (2-43) were prepared following the same method as in example 1:

| Ex. | Structure | Name | NMR |
|---|---|---|---|
| 2 | ![structure] | N-(1-(2-(piperidin-1-yl)ethyl)-1H-pyrazolo[3,4-d]pyrimidin-4-yl)-1-naphthamide | $^1$H NMR (CDCl$_3$) δ ppm: 8.87 (s, 1H), 8.58 (s, 1H), 8.48 (d, J = 8.2 Hz, 1H), 8.07 (d, J = 8.3 Hz, 1H), 7.95 (d, J = 7.5 Hz, 1H), 7.91 (d, J = 7.8 Hz, 1H), 7.68-7.52 (m, 3H), 4.65 (t, J = 7.1 Hz, 2H), 2.91 (t, J = 7.1 Hz, 2H), 2.56-2.46 (m, 4H), 1.57-1.48 (m, 4H), 1.47-1.33 (m, 2H). |

| Ex. | Structure | Name | NMR |
|---|---|---|---|
| 3 | 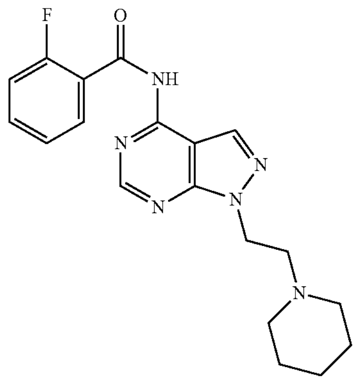 [SMILES: O=C(Nc1ncnc2c1cnn2CCN1CCCCC1)c1ccccc1F] | 2-fluoro-N-(1-(2-(piperidin-1-yl)ethyl)-1H-pyrazolo[3,4-d]pyrimidin-4-yl)benzamide | ¹H NMR (CD₃OD) δ ppm: 8.77 (s, 2H), 7.93 (td, J = 7.5, 1.8 Hz, 1H), 7.79-7.64 (m, 1H), 7.51-7.28 (m, 2H), 4.97 (t, J = 5.9 Hz, 2H), 3.77 (t, J = 5.9 Hz, 2H), 3.78-3.70 (m, 2H), 2.10-1.92 (m, 2H), 1.92-1.67 (m, 3H), 1.67-1.46 (m, 1H). |
| 4 | 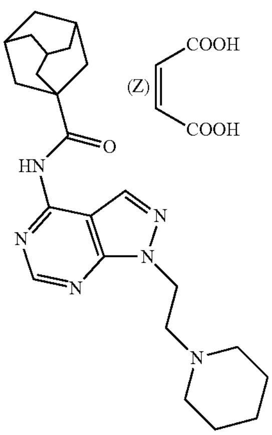 [SMILES: O=C(Nc1ncnc2c1cnn2CCN1CCCCC1)C12CC3CC(CC(C3)C1)C2 ; O=C(O)/C=C\C(=O)O] | N-(1-[2-(Piperidin-1-yl)ethyl]-1H-pyrazolo[3,4-d]pyrimidin-4-yl)-1-adamantylcarboxamide maleate | ¹H NMR (DMSO-d₆) δ ppm: 10.65 (s, 1H), 8.7 (s, 1H), 8.45 (s, 1H), 6.0 (s, 2H), 4.75 (m, 2H), 3,6 (m, 4H), 2.95 (m, 2H), 2.0 (m, 10H), 1.7-1.4 (m, 11H). |
| 5 | 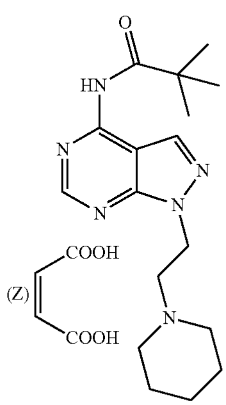 | N-(1-(2-(Piperidin-1-yl)ethyl)-1H-pyrazolo[3,4-d]pyrimidin-4-yl)pivalamide maleate | ¹H NMR (DMSO-d₆) δ ppm: 10.75 (s, 1H), 8.7 (s, 1H), 8.45 (s, 1H), 6.0 (s, 2H), 4.8 (m, 2H), 3.55 (m, 4H), 3.0 (m, 2H), 1.8-1.5 (m, 6H), 1.3 (s, 9H). |
| 6 | 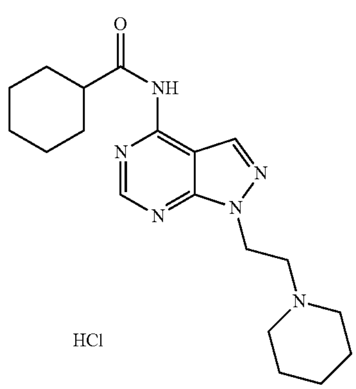 [SMILES: O=C(Nc1ncnc2c1cnn2CCN1CCCCC1)C1CCCCC1 ; Cl] | N-(1-(2-(Piperidin-1-yl)ethyl)-1H-pyrazolo[3,4-d]pyrimidin-4-yl)cyclohexanecarboxamide hydrochloride | ¹H NMR (CD₃OD) δ ppm: 8.75 (2 s, 2H), 4.95 (t, J = 6.0 Hz, 2H), 3.75 (m, 4H), 3.05 (t, 2H), 2.65 (m, 1H), 2.0-1.75 (m, 10H), 1.6-1.3 (m, 6H). |

-continued

| Ex. | Structure | Name | NMR |
|---|---|---|---|
| 7 | (structure: 2,4-dichlorobenzamide linked to pyrazolo[3,4-d]pyrimidine with piperidinylethyl substituent) HCl | 2,4-Dichloro-N-(1-(2-(piperidin-1-yl)ethyl)-1H-pyrazolo[3,4-d]pyrimidin-4-yl)benzamide hydrochloride | $^1$H NMR (CD$_3$OD) δ ppm: 8.75 (s, 1H), 8.7 (s, 1H), 7.7 (m, 2H), 7.55 (dd, J = 1.9 Hz; 8.4 Hz, 1H), 4.95 (t, J = 6.0 Hz, 2H), 3.75 (m, 4H), 3.05 (t, J = 10.2 Hz, 2H), 2.0-1.45 (m, 6H). |
| 8 | (structure: 1,5-dimethylpyrazole-3-carboxamide linked to pyrazolo[3,4-d]pyrimidine with piperidinylethyl substituent) HCl | 1,5-dimethyl-N-(1-(2-(piperidin-1-yl)ethyl)-1H-pyrazolo[3,4-d]pyrimidin-4-yl)-1H-pyrazole-3-carboxamide hydrochloride | $^1$H NMR (CD$_3$OD) δ ppm: 8.88 (s, 1H), 8.77 (s, 1H), 6.78 (s, 1H), 4.97 (t, J = 5.9 Hz, 2H), 3.95 (s, 3H), 3.77 (t, J = 5.9 Hz, 2H), 3.77-3.67 (m, 2H), 3.15-2.95 (m, 2H), 2.39 (s, 3H), 2.05-1.90 (m, 2H), 1.90-1.68 (m, 3H), 1.66-1.47 (m, 1H). |
| 9 | (structure: 3,5-di-tert-butylbenzamide linked to pyrazolo[3,4-d]pyrimidine with piperidinylethyl substituent) HCl | 3,5-di-tert-Butyl-N-(1-(2-(piperidin-1-yl)ethyl)-1H-pyrazolo[3,4-d]pyrimidin-4-yl)benzamide hydrochloride | $^1$H NMR (DMSO-d$_6$) δ ppm: 8.75 (bs, 1H), 8.55 (s, 1H), 8.5 (s, 1H), 7.95 (s, 2H), 7.7 (s, 1H), 4.9 (t, J = 6.6 Hz, 2H), 3.6 (m, 4H), 2.95 (m, 2H), 1.8 (m, 6H), 1.35 (s, 18H). |
| 10 | (structure: 2-hydroxybenzamide linked to pyrazolo[3,4-d]pyrimidine with piperidinylethyl substituent) HCl | 2-hydroxy-N-(1-(2-(piperidin-1-yl)ethyl)-1H-pyrazolo[3,4-d]pyrimidin-4-yl)benzamide hydrochloride | $^1$H NMR (DMSO-d$_6$) δ ppm: 8.75 (s, 1H), 8.74 (s, 1H), 8.08 (dd, J = 7.9, 1.7 Hz, 1H), 7.59-7.46 (m, 1H), 7.16 (d, J = 8.2 Hz, 1H), 7.05 (t, J = 7.5 Hz, 1H), 4.89 (t, J = 6.4 Hz, 2H), 3.74-3.54 (m, 4H), 3.06-2.87 (m, 2H), 1.94-1.56 (m, 5H), 1.47-1.27 (m, 1H). |

| Ex. | Structure | Name | NMR |
|---|---|---|---|
| 11 | (structure with noradamantyl carboxamide, pyrazolo[3,4-d]pyrimidine, piperidinylethyl, and (Z)-maleate COOH/COOH) | N-(1-(2-(piperidin-1-yl)ethyl)-1H-pyrazolo[3,4-d]pyrimidin-4-yl)(1-noradamantylcarboxamide) maleate | $^1$H NMR (DMSO-$d_6$) δ ppm: 10.53 (s, 1H), 8.73 (s, 1H), 8.50 (s, 1H), 6.05 (s, 2H), 4.82 (t, J = 6.2 Hz, 2H), 3.60 (t, J = 6.1 Hz, 2H), 3.28-3.10 (m, 4H), 2.85 (t, J = 6.7 Hz, 1H), 2.41-2.25 (m, 2H), 2.25-2.07 (m, 2H), 2.07-1.95 (m, 2H), 1.95-1.80 (m, 2H), 1.80-1.41 (m, 10H). |
| 12 | (pivalamide-pyrazolopyrimidine-morpholinoethyl, HCl) | N-(1-(2-Morpholinoethyl)-1H-pyrazolo[3,4-d]pyrimidin-4-yl)pivalamide hydrochloride | $^1$H NMR (CD$_3$OD) δ ppm: 8.78 (s, 1H), 8.76 (s, 1H), 4.98 (t, J = 5.8 Hz, 2H), 4.17-4.00 (m, 2H), 3.84 (t, J = 5.8 Hz, 2H), 3.84-3.64 (m, 4H), 3.30-3.23 (m, 2H), 1.41 (s, 9H). |
| 13 | (pivalamide-pyrazolopyrimidine-diisopropylaminoethyl, HCl) | N-(1-(2-(Diisopropylamino)ethyl)-1H-pyrazolo[3,4-d]pyrimidin-4-yl)pivalamide hydrochloride | $^1$H NMR (CD$_3$OD) δ ppm: 8.75 (s, 2H), 4.9 (t, J = 7.0 Hz, 2H), 3.9 (m, 2H), 3.75 (t, J = 7.0 Hz, 2H), 1.45 (d, J = 6.4 Hz, 12H), 1.4 (s, 9H). |
| 14 | (cyclohexanecarboxamide-pyrazolopyrimidine-morpholinoethyl, HCl) | N-(1-(2-Morpholinoethyl)-1H-pyrazolo[3,4-d]pyrimidin-4-yl)cyclohexanecarboxamide hydrochloride | $^1$H NMR (CD$_3$OD) δ ppm: 8.75 (s, 1H), 8.7 (s, 1H), 5.0 (t, J = 6.0 Hz, 4H), 4.05 (m, 2H), 3.85 (t, J = 6.0 Hz, 4H), 3.7 (m, 2H), 2.7 (m, 1H), 2.0 (m, 2H), 1.9 (m, 2H), 1.8 (m, 1H), 1.6-1.35 (m, 5H). |

-continued

| Ex. | Structure | Name | NMR |
|---|---|---|---|
| 15 | 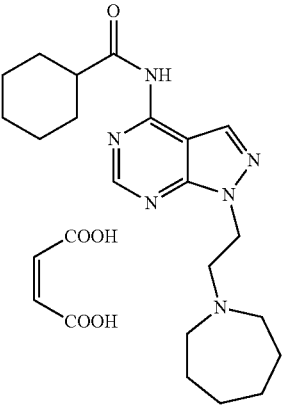 [SMILES: O=C(Nc1ncnc2c1cnn2CCN1CCCCCC1)C1CCCCC1 ; O=C(O)/C=C\C(=O)O] | N-(1-(2-(Azepan-1-yl)ethyl)-1H-pyrazolo[3,4-d]pyrimidin-4-yl)cyclohexanecarboxamide maleate | $^1$H NMR (DMSO-d$_6$) δ ppm: 11.23 (s, 1H), 8.69 (s, 1H), 8.55 (s, 1H), 6.22-5.96 (m, 2H), 4.94-4.61 (m, 2H), 3.79-3.51 (m, 4H), 2.68 (t, J = 11.2 Hz, 1H), 2.03-1.16 (m, 18H). |
| 16 | 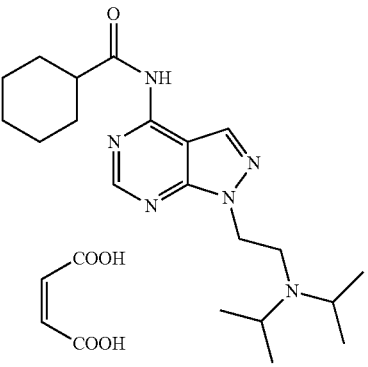 [SMILES: CC(C)N(CCn1ncc2c(NC(=O)C3CCCCC3)ncnc21)C(C)C ; O=C(O)/C=C\C(=O)O] | N-(1-(2-(Diisopropylamino)ethyl)-1H-pyrazolo[3,4-d]pyrimidin-4-yl)cyclohexanecarboxamide maleate | $^1$H NMR (CDCl$_3$) δ ppm: 8.7 (s, 1H), 8.6 (s, 1H), 8.3 (bs, 1H), 6.3 (s, 2H), 5.0 (m, 2H), 3.8 (m, 2H), 3.4 (m, 2H), 2.4 (m, 1H), 2.05 (m, 2H), 1.85 (m, 2H), 1.75 (m, 2H), 1.6 (d, J = 6.5 Hz, 12H), 1.45-1.2 (m, 4H). |
| 17 | 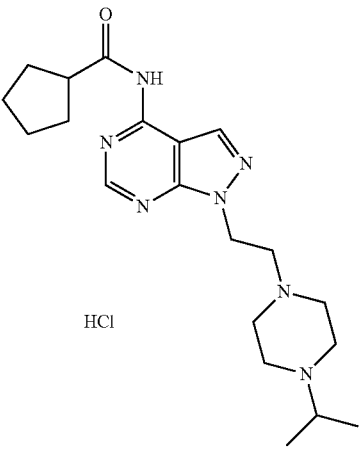 [SMILES: CC(C)N1CCN(CCn2ncc3c(NC(=O)C4CCCC4)ncnc32)CC1 ; Cl] | N-(1-[2-(Morpholinoethyl]-1H-pyrazolo[3,4-d]pyrimidin-4-yl)-1-adamantylcarboxamide hydrochloride | $^1$H NMR (CD$_3$OD) δ ppm: 8.8 (s, 1H), 8.75 (s, 1H), 5.0 (t, J = 5.8 Hz, 2H), 4.1 (m, 2H), 3.85-3.65 (m, 8H), 2.1 (m, 9H), 1.85 (m, 6H). |
| 18 | 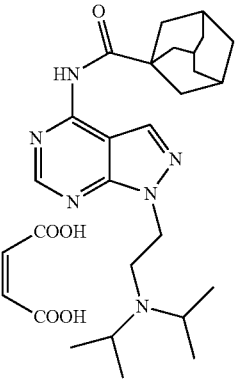 | N-(1-(2-(Diisopropylamino)ethyl)-1H-pyrazolo[3,4-d]pyrimidin-4-yl)-1-adamantylcarboxamide maleate | $^1$H NMR (CDCl$_3$) δ ppm: 8.75 (s, 1H), 8.6 (s, 1H), 8.4 (bs, 1H), 6.3 (s, 2H), 4.95 (m, 2H), 3.8 (m, 2H), 2.15 (m, 3H), 2.05 (m, 6H), 1.8 (m, 8H), 1.5 (d, J = 6.6 Hz, 12H). |

| Ex. | Structure | Name | NMR |
|---|---|---|---|
| 19 | 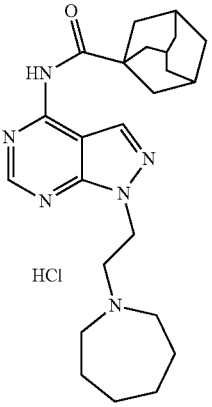 [SMILES: O=C(Nc1ncnc2c1cnn2CCN1CCCCCC1)C12CC3CC(CC(C3)C1)C2 ; Cl] | N-(1-(2-(Azepan-1-yl)ethyl)-1H-pyrazolo[3,4-d]pyrimidin-4-yl) 1-adamantylcarboxamide hydrochloride | $^1$H NMR (CD$_3$OD) δ ppm: 8.79 (s, 1H), 8.75 (s, 1H), 4.95 (t, J = 6.0 Hz, 2H), 3.83 (t, J = 6.0 Hz, 2H), 3.69-3.57 (m, 2H), 3.40-3.31 (m, 2H), 2.19-2.07 (m, 8H), 2.04-1.81 (m, 11H), 1.81-1.64 (m, 4H). |
| 20 | 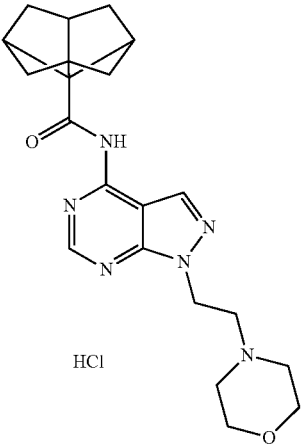 [SMILES: O=C(Nc1ncnc2c1cnn2CCN1CCOCC1)C12C3CC4CC1CC42C3 ; Cl] | N-(1-[2-(Morpholinoethyl]-1H-pyrazolo[3,4-d]pyrimidin-4-yl)-1-noradamantylcarboxamide hydrochloride | $^1$H NMR (CD$_3$OD) δ ppm: 8.8 (s, 1H), 8.75 (s, 1H), 4.95 (t, J = 5.8 Hz, 2H), 4.1 (m, 2H), 3.85-3.65 (m, 6H), 2.95 (m, 1H), 2.4 (m, 2H), 2.15 (m, 4H), 1.95 (m, 2H), 1.75 (m, 4H). |
| 21 | 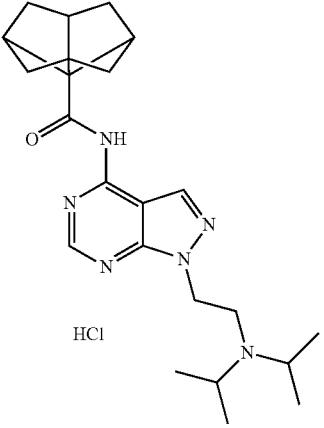 [SMILES: CC(C)N(CCn1ncc2c(NC(=O)C34C5CC6CC3CC64C5)ncnc21)C(C)C ; Cl] | N-(1-(2-(Diisopropylamino)ethyl)-1H-pyrazolo[3,4-d]pyrimidin-4-yl)-1-noradamantylcarboxamide hydrochloride | $^1$H NMR (CD$_3$OD) δ ppm: 8.75 (s, 2H), 4.9 (t, J = 7.2 Hz, 2H), 3.9 (m, 2H), 3.75 (t, J = 7.2 Hz, 2H), 2.95 (m, 1H), 2.4 (m, 2H), 2.15 (m, 3H), 1.95 (m, 2H), 1.75 (m, 3H), 1.45 (d, J = 6.5 Hz, 12H). |

| Ex. | Structure | Name | NMR |
|---|---|---|---|
| 22 | 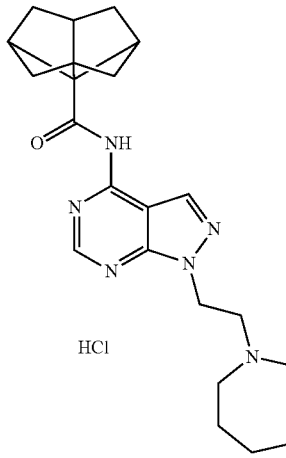 | N-(1-(2-(Azepan-1-yl)ethyl)-1H-pyrazolo[3,4-d]pyrimidin-4-yl) 1-noradamantylcarboxamide hydrochloride | $^1$H NMR (CD$_3$OD) δ ppm: 8.75 (s, 1H), 8.6 (s, 1H), 6.2 (s, 2H), 4.9 (m, 2H), 3.8 (t, J = 5.9 Hz, 2H), 2.9 (t, J = 6.7 Hz, 1H), 2.45 (m, 2H), 2.15 (m, 4H), 1.75-1.65 (m, 18H). |
| 23 | 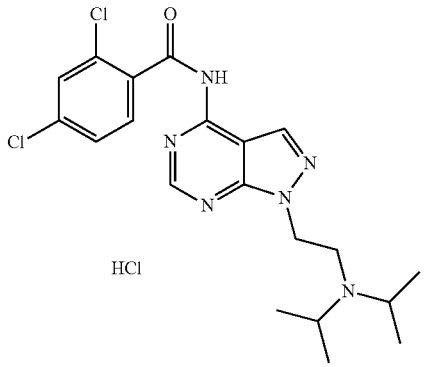 [SMILES: CC(C)N(CCn1ncc2c(NC(=O)c3ccc(Cl)cc3Cl)ncnc21)C(C)C ; Cl] | 2,4-Dichloro-N-(1-(2-(diisopropylamino)ethyl)-1H-pyrazolo[3,4-d]pyrimidin-4-yl)benzamide hydrochloride | $^1$H NMR (CD$_3$OD) δ ppm: 8.75 (s, 2H), 7.7 (s + d, J = 9.8 Hz, 2H), 7.5 (d, J = 8.4 Hz, 1H), 4.9 (t, J = 7.1 Hz, 2H), 3.95 (m, 2H), 3.75 (t, J = 7.2 Hz, 2H), 1.45 (d, J = 6.5 Hz, 12H). |
| 24 | 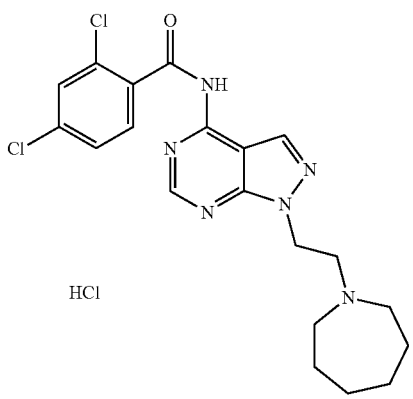 [SMILES: O=C(Nc1ncnc2c1cnn2CCN1CCCCCC1)c1ccc(Cl)cc1Cl ; Cl] | N-(1-(2-(Azepan-1-yl)ethyl)-1H-pyrazolo[3,4-d]pyrimidin-4-yl)-2,4-dichlorobenzamide hydrochloride | $^1$H NMR (CD$_3$OD) δ ppm: 8.75 (s, 2H), 7.70 (d, J = 8.4 Hz, 1H), 7.68 (d, J = 2.0 Hz, 1H), 7.54 (dd, J = 8.3, 2.0 Hz, 1H), 4.95 (t, J = 5.9 Hz, 2H), 3.84 (t, J = 5.9 Hz, 2H), 3.71-3.57 (m, 2H), 3.41-3.31 (m, 2H), 2.09-1.82 (m, 4H), 1.82-1.70 (m, 4H). |
| 25 | 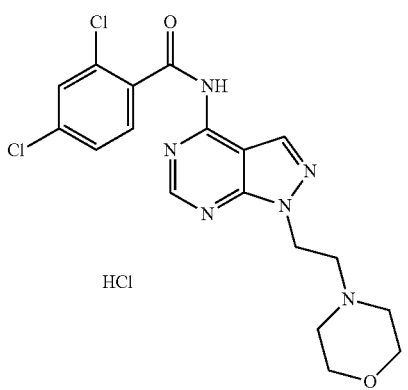 [SMILES: O=C(Nc1ncnc2c1cnn2CCN1CCOCC1)c1ccc(Cl)cc1Cl ; Cl] | 2,4-Dichloro-N-(1-(2-morpholinoethyl)-1H-pyrazolo[3,4-d]pyrimidin-4-yl)benzamide hydrochloride | $^1$H NMR (CD$_3$OD) δ ppm: 8.75 (s, 2H), 7.7 (s + d, J = 11.2 Hz, 2H), 7.55 (dd, J = 8.3 Hz, 2.0 Hz, 1H), 4.95 (t, J = 5.8 Hz, 2H), 4.1 (m, 2H), 3.85 (t, J = 5.8 Hz, 2H), 3.75-3.6 (m, 6H). |

| Ex. | Structure | Name | NMR |
|---|---|---|---|
| 26 | 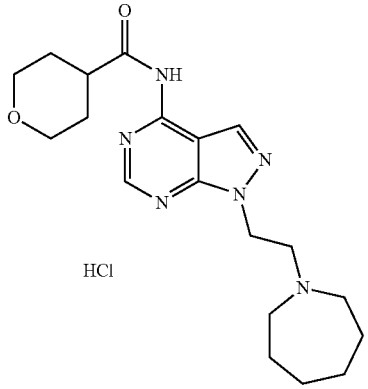 [SMILES: O=C(Nc1ncnc2c1cnn2CCN1CCCCCC1)C1CCOCC1 ; Cl] | N-(1-(2-(Azepan-1-yl)ethyl)-1H-pyrazolo[3,4-d]pyrimidin-4-yl)tetrahydro-2H-pyran-4-carboxamide hydrochloride | $^1$H NMR (CD$_3$OD) δ ppm: 8.76 (s, 1H), 8.73 (s, 1H), 4.94 (t, J = 5.9 Hz, 2H), 4.03 (dt, J = 6.7, 3.6 Hz, 2H), 3.83 (t, J = 5.9 Hz, 2H), 3.76-3.43 (m, 4H), 3.36-3.33 (m, 2H), 3.09-2.86 (m, 1H), 2.04-1.81 (m, 8H), 1.81-1.66 (m, 4H). |
| 27 | 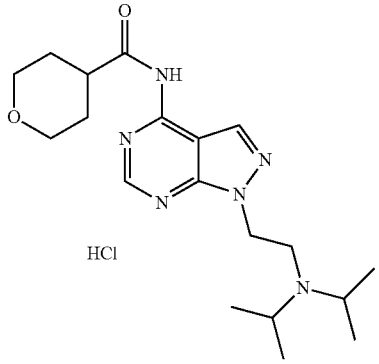 [SMILES: CC(C)N(CCn1ncc2c(NC(=O)C3CCOCC3)ncnc21)C(C)C ; Cl] | N-(1-(2-(Diisopropylamino)ethyl)-1H-pyrazolo[3,4-d]pyrimidin-4-yl)tetrahydro-2H-pyran-4-carboxamide hydrochloride | $^1$H NMR (CD$_3$OD) δ ppm: 8.69, 8.68 (s, 1H), 8.44, 8.44 (s, 1H), 4.94-4.80 (m, 2H), 4.02 (dt, J = 11.3, 3.3 Hz, 1H), 3.97-3.81 (m, 3H), 3.73 (t, J = 7.1 Hz, 2H), 3.59-3.38 (m, 2H), 2.98-2.77, 2.61-2.42 (m, 1H), 1.97-1.78 (m, 3H), 1.78-1.57 (m, 1H), 1.54-1.34 (m, 12H). |
| 28 | 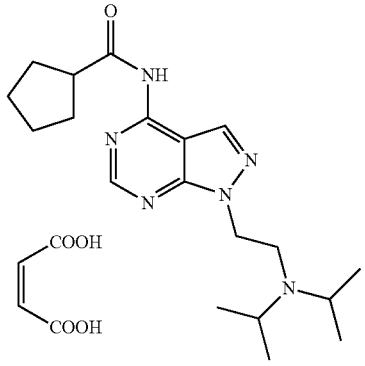 [SMILES: CC(C)N(CCn1ncc2c(NC(=O)C3CCCC3)ncnc21)C(C)C ; O=C(O)/C=C\C(=O)O] | N-(1-(2-(Diisopropylamino)ethyl)-1H-pyrazolo[3,4-d]pyrimidin-4-yl)cyclopentanecarboxamide maleate | $^1$H NMR (CDCl$_3$) δ ppm: 8.75 (s, 1H), 8.6 (s, 1H), 6.3 (s, 2H), 4.95 (m, 2H), 3.8 (m, 2H), 3.45 (m, 2H), 2.9 (m, 1H), 2.0 (m, 4H), 1.8 (m, 2H), 1.7 (m, 2H), 1.5 (bs, 12H). |
| 29 | 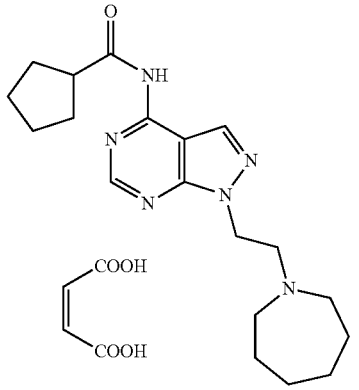 [SMILES: O=C(Nc1ncnc2c1cnn2CCN1CCCCCC1)C1CCCC1 ; O=C(O)/C=C\C(=O)O] | N-(1-(2-(azepan-1-yl)ethyl)-1H-pyrazolo[3,4-d]pyrimidin-4-yl)cyclopentanecarboxamide maleate | $^1$H NMR (DMSO-d$_6$) δ ppm: 11.31 (s, 1H), 8.70 (s, 1H), 8.57 (s, 1H), 6.05 (s, 2H), 4.80 (t, J = 5.9 Hz, 2H), 3.67 (t, J = 5.9 Hz, 2H), 3.26-2.99 (m, 4H), 2.06-1.41 (m, 17H). |

-continued

| Ex. | Structure | Name | NMR |
|---|---|---|---|
| 30 | 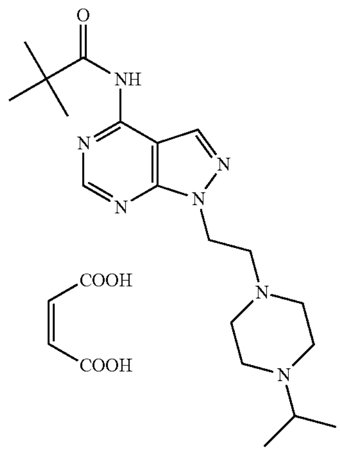 [SMILES: CC(C)N1CCN(CCn2ncc3c(NC(=O)C(C)(C)C)ncnc32)CC1 ; O=C(O)/C=C\C(=O)O] | N-(1-(2-(4-isopropylpiperazin-1-yl)ethyl)-1H-pyrazolo[3,4-d]pyrimidin-4-yl)pivalamide maleate | $^1$H NMR (CD$_3$OD) δ ppm: 8.61 (s, 1H), 8.54 (s, 1H), 6.25 (s, 2H), 4.62 (t, J = 6.0 Hz, 2H), 3.49-3.34 (m, 1H), 3.48-2.31 (m, 8H), 3.01 (t, J = 6.0 Hz, 2H), 1.38 (s, 9H), 1.29 (d, J = 6.6 Hz, 6H). |
| 31 | 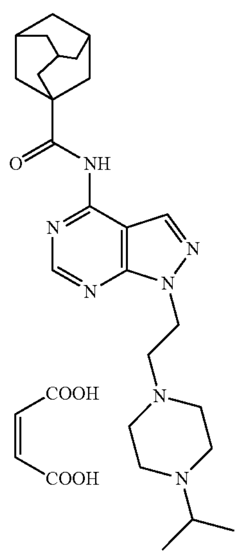 [SMILES: O=C(O)/C=C\C(=O)O ; CC(C)N1CCN(CCn2ncc3c(NC(=O)C45CC6CC(CC(C6)C4)C5)ncnc32)CC1] | N-(1-(2-(4-isopropylpiperazin-1-yl)ethyl)-1H-pyrazolo[3,4-d]pyrimidin-4-yl) 1-adamantylcarboxamide maleate | $^1$H NMR (CD$_3$OD) δ ppm: 8.61 (s, 1H), 8.54 (s, 1H), 6.29 (s, 4H), 4.62 (t, J = 6.0 Hz, 2H), 3.49-3.35 (m, 1H), 3.46-2.35 (m, 8H), 3.01 (t, J = 6.0 Hz, 3H), 2.18-2.04 (m, 9H), 1.93-1.77 (m, 6H), 1.30 (d, J = 6.7 Hz, 6H). |
| 32 | 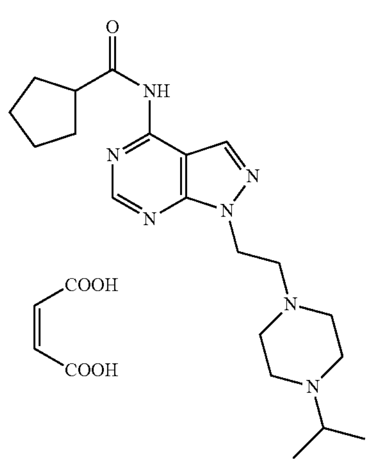 [SMILES: CC(C)N1CCN(CCn2ncc3c(NC(=O)C4CCCC4)ncnc32)CC1 ; O=C(O)/C=C\C(=O)O] | N-(1-(2-(4-isopropylpiperazin-1-yl)ethyl)-1H-pyrazolo[3,4-d]pyrimidin-4-yl)cyclopentanecarboxamide maleate | $^1$H NMR (CD$_3$OD) δ ppm: 8.59 (s, 1H), 8.57 (s, 1H), 6.28 (s, 4H), 4.61 (t, J = 6.0 Hz, 2H), 3.48-3.35 (m, 1H), 3.55-2.28 (m, 8H), 3.12-2.97 (m, 1H), 3.01 (t, J = 6.0 Hz, 2H), 2.11-1.55 (m, 8H), 1.30 (d, J = 6.6 Hz, 6H). |

-continued

| Ex. | Structure | Name | NMR |
|---|---|---|---|
| 33 | 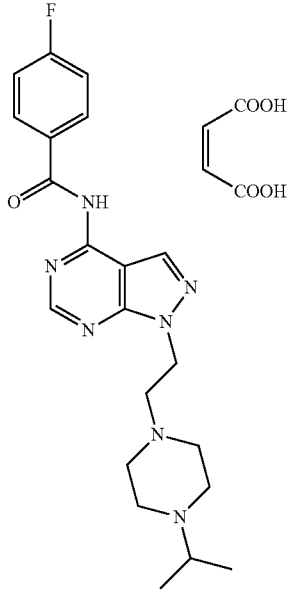 [SMILES: CC(C)N1CCN(CCn2ncc3c(NC(=O)c4ccc(F)cc4)ncnc32)CC1 ; O=C(O)/C=C\C(=O)O] | 4-fluoro-N-(1-(2-(4-isopropylpiperazin-1-yl)ethyl)-1H-pyrazolo[3,4-d]pyrimidin-4-yl)benzamide maleate | $^1$H NMR (CD$_3$OD) δ ppm: 8.67 (s, 1H), 8.59 (s, 1H), 8.14 (dd, J = 8.8, 5.3 Hz, 2H), 7.31 (t, J = 8.8 Hz, 2H), 6.29 (s, 4H), 4.65 (t, J = 6.0 Hz, 2H), 3.51-3.38 (m, 1H), 3.57-2.26 (m, 8H), 3.03 (t, J = 6.0 Hz, 2H), 1.31 (d, J = 6.6 Hz, 6H). |
| 34 | 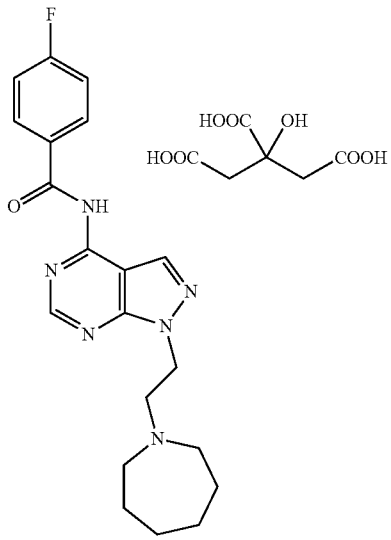 [SMILES: O=C(Nc1ncnc2c1cnn2CCN1CCCCCC1)c1ccc(F)cc1 ; O=C(O)CC(O)(CC(=O)O)C(=O)O] | N-(1-(2-(azepan-1-yl)ethyl)-1H-pyrazolo[3,4-d]pyrimidin-4-yl)-4-fluorobenzamide citrate | $^1$H NMR (CD$_3$OD) δ ppm: 8.72 (s, 1H), 8.67 (s, 1H), 8.14 (dd, J = 9.0, 5.3 Hz, 2H), 7.31 (dd, J = 9.0, 8.6 Hz, 2H), 4.88 (t, J = 6.0 Hz, 2H), 3.72 (t, J = 6.0 Hz, 2H), 3.43-3.34 (m, 4H), 2.78 (dd, J = 33.0, 14.6 Hz, 4H), 1.96-1.85 (m, 4H), 1.77-1.68 (m, 4H). |
| 35 | 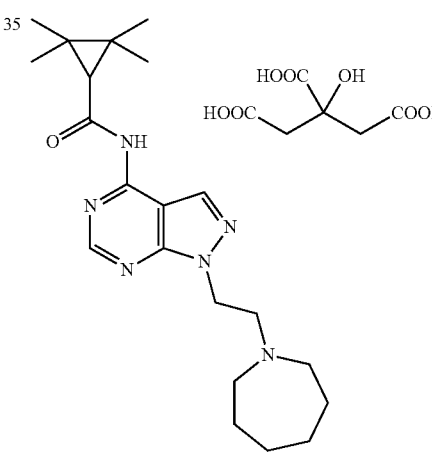 | N-(1-(2-(azepan-1-yl)ethyl)-1H-pyrazolo[3,4-d]pyrimidin-4-yl)-2,2,3,3-tetramethylcyclopropane-carboxamide citrate | $^1$H NMR (CD$_3$OD) δ ppm: 8.63 (s, 1H), 8.61 (s, 1H), 4.85 (t, J = 5.6 Hz, 2H), 3.74 (t, J = 5.6 Hz, 2H), 3.46-3.37 (m, 4H), 2.79 (dd, J = 28.6, 15.5 Hz, 4H), 1.97-1.85 (m, 4H), 1.80-1.67 (m, 4H), 1.55 (s, 1H), 1.36 (s, 6H), 1.29 (s, 6H). |

| Ex. | Structure | Name | NMR |
|---|---|---|---|
| 36 | 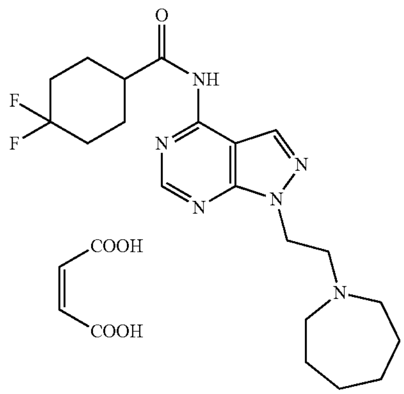 [SMILES: O=C(Nc1ncnc2c1cnn2CCN1CCCCCC1)C1CCC(F)(F)CC1 ; O=C(O)/C=C\C(=O)O] | N-(1-(2-(azepan-1-yl)ethyl)-1H-pyrazolo[3,4-d]pyrimidin-4-yl)-4,4-difluorocyclohexanecarboxamide maleate | $^1$H NMR (CD$_3$OD) δ ppm: 8.67 (s, 1H), 8.66 (s, 1H), 6.26 (s, 2H), 4.88 (t, J = 5.9 Hz, 2H), 3.80 (t, J = 5.9 Hz, 2H), 3.70-3.15 (m, 4H), 2.80-2.66 (m, 1H), 2.27-2.11 (m, 2H), 2.11-1.82 (m, 10H), 1.81-1.69 (m, 4H). |
| 37 | 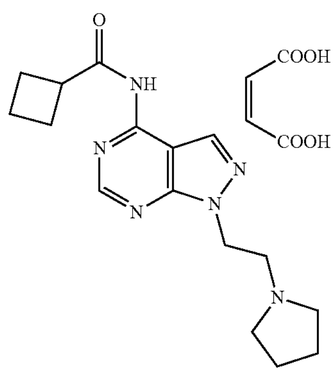 | N-(1-(2-(pyrrolidin-1-yl)ethyl)-1H-pyrazolo[3,4-d]pyrimidin-4-yl)cyclobutanecarboxamide maleate | $^1$H NMR (CD$_3$OD) δ ppm: 8.72 (s, 1H), 8.64 (s, 1H), 6.25 (s, 2H), 4.85 (t, J = 5.7 Hz, 2H), 3.84 (t, J = 5.7 Hz, 2H), 3.61-3.40 (m, 1H), 3.94-3.04 (m, 4H), 2.52-2.20 (m, 4H), 2.20-1.86 (m, 6H). |
| 38 | 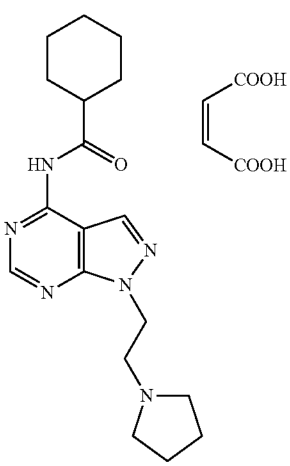 [SMILES: O=C(Nc1ncnc2c1cnn2CCN1CCCC1)C1CCCCC1 ; O=C(O)/C=C\C(=O)O] | N-(1-(2-(pyrrolidin-1-yl)ethyl)-1H-pyrazolo[3,4-d]pyrimidin-4-yl)cyclohexanecarboxamide maleate | $^1$H NMR (CD$_3$OD) δ ppm: 8.66 (s, 1H), 8.64 (s, 1H), 6.24 (s, 2H), 4.85 (t, J = 5.6 Hz, 2H), 3.83 (t, J = 5.6 Hz, 2H), 3.48-3.19 (m, 4H), 2.60 (tt, J = 11.7, 3.6 Hz, 1H), 2.21-1.68 (m, 9H), 1.65-1.24 (m, 5H). |
| 39 | 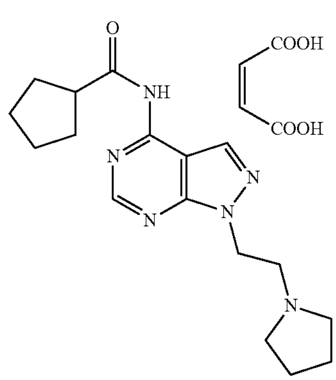 | N-(1-(2-(pyrrolidin-1-yl)ethyl)-1H-pyrazolo[3,4-d]pyrimidin-4-yl)cyclopentanecarboxamide maleate | $^1$H NMR (CD$_3$OD) δ ppm: 8.68 (s, 1H), 8.65 (s, 1H), 6.24 (s, 2H), 4.85 (t, J = 5.6 Hz, 2H), 3.83 (t, J = 5.6 Hz, 2H), 3.61-3.20 (m, 4H), 3.09-3.02 (m, 1H), 2.18-1.59 (m, 12H). |

| Ex. | Structure | Name | NMR |
|---|---|---|---|
| 40 | 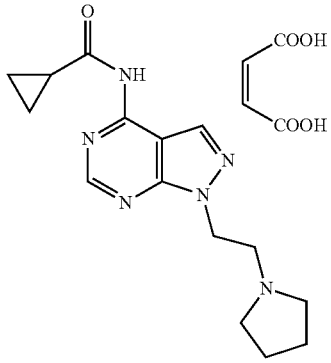 | N-(1-(2-(pyrrolidin-1-yl)ethyl)-1H-pyrazolo[3,4-d]pyrimidin-4-yl)cyclopropanecarboxamide maleate | $^1$H NMR (CD$_3$OD) δ ppm: 8.63 (s, 1H), 8.61 (s, 1H), 6.22 (s, 2H), 4.79 (t, J = 5.9 Hz, 2H), 3.65 (t, J = 5.9 Hz, 2H), 3.44-3.20 (m, 4H), 2.22-1.75 (m, 5H), 1.18-1.05 (m, 2H), 1.05-0.93 (m, 2H). |
| 41 | 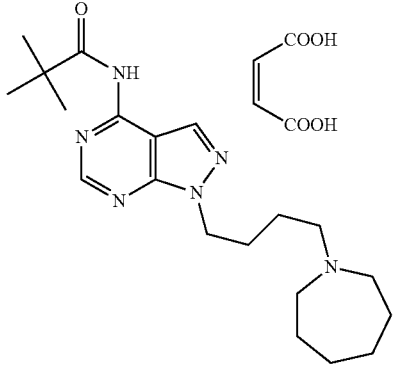 [SMILES: CC(C)(C)C(=O)Nc1ncnc2c1cnn2CCCCN1CCCCCC1 ; O=C(O)/C=C\C(=O)O] | N-(1-(4-(azepan-1-yl)butyl)-1H-pyrazolo[3,4-d]pyrimidin-4-yl)pivalamide maleate | $^1$H NMR (CD$_3$OD) δ ppm: 8.62 (s, 1H), 8.55 (s, 1H), 6.24 (s, 2H), 4.53 (t, J = 6.6 Hz, 2H), 3.29-3.22 (m, 4H), 3.22-3.13 (m, 2H), 2.02 (q, J = 7.0 Hz, 2H), 1.95-1.81 (m, 4H), 1.79-1.60 (m, 6H), 1.38 (s, 9H). |
| 42 | 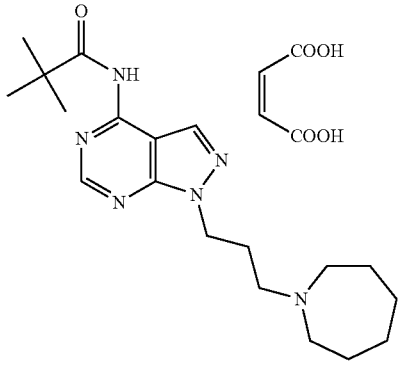 | N-(1-(3-(azepan-1-yl)propyl)-1H-pyrazolo[3,4-d]pyrimidin-4-yl)pivalamide maleate | $^1$H NMR (CD$_3$OD) δ ppm: 8.64 (s, 1H), 8.58 (s, 1H), 6.25 (s, 2H), 4.59 (t, J = 6.4 Hz, 1H), 3.52-3.33 (m, 2H), 3.27-3.16 (m, 4H), 2.48-2.30 (m, 2H), 1.98-1.80 (m, 4H), 1.78-1.66 (m, 4H), 1.38 (s, 9H). |
| 43 | 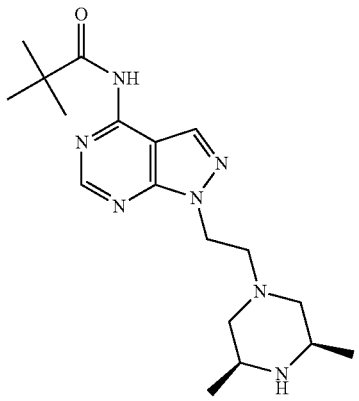 [SMILES: C[C@@H]1CN(CCn2ncc3c(NC(=O)C(C)(C)C)ncnc32)C[C@H](C)N1] | N-(1-(2-((3S,5R)-3,5-dimethylpiperazin-1-yl)ethyl)-1H-pyrazolo[3,4-d]pyrimidin-4-yl)pivalamide | $^1$H NMR (CD$_3$OD) δ ppm: 8.60 (s, 1H), 8.53 (s, 1H), 4.61 (t, J = 6.6 Hz, 2H), 2.96-2.89 (m, 2H), 2.89 (t, J = 6.5 Hz, 2H), 2.81-2.62 (m, 2H), 1.72 (t, J = 10.9 Hz, 2H), 1.38 (s, 9H), 1.04 (d, J = 6.5 Hz, 6H). |

Example 44

Synthesis of 1-(1-(2-(1,4-oxazepan-4-yl)ethyl)-1H-pyrazolo[3,4-d]pyrimidin-4-yl)-3-propylurea

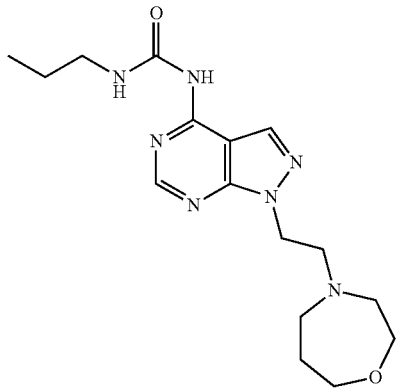 [SMILES: CCCNC(=O)Nc1ncnc2c1cnn2CCN1CCCOCC1]

1-(2-(1,4-oxazepan-4-yl)ethyl)-1H-pyrazolo[3,4-d]pyrimidin-4-amine (0.039 g, 0.149 mmol), propyl isocyanate (0.032 g, 0.376 mmol) in 3 mL of toluene were heated in CEM microwave reactor for 20 minutes at 140° C. The mixture was concentrated under reduced pressure, treated with acetonitrile and filtered to afford 6 mg of 1-(1-(2-(1,4-oxazepan-4-yl)ethyl)-1H-pyrazolo[3,4-d]pyrimidin-4-yl)-3-propylurea. $^1$H NMR (CD$_3$OD) δ ppm: 8.54 (s, 1H), 8.34 (s, 1H), 4.55 (t, J=6.3 Hz, 2H), 3.66 (t, J=5.6 Hz, 2H), 3.62-3.52 (m, 2H), 3.42-3.26 (m, 2H), 3.08 (t, J=6.3 Hz, 2H), 2.79-2.63 (m, 4H), 1.84-1.71 (m, 2H), 1.72-1.57 (m, 2H), 1.01 (t, J=7.3 Hz, 3H).

Examples (45-74) were prepared following the same method as example 44:

| Ex. | Structure | Name | NMR |
|---|---|---|---|
| 45 | 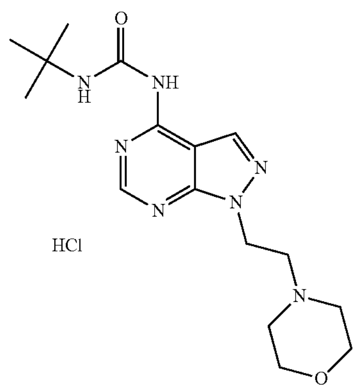 [SMILES: CC(C)(C)NC(=O)Nc1ncnc2c1cnn2CCN1CCOCC1 ; Cl] | 1-tert-Butyl-3-(1-(2-morpholinoethyl)-1H-pyrazolo[3,4-d]pyrimidin-4-yl)urea hydrochloride | $^1$H NMR (CD$_3$OD) δ ppm: 8.65 (s, 1H), 8.59 (s, 1H), 4.98 (t, J = 5.9 Hz, 2H), 4.20-3.97 (m, 2H), 3.84 (t, J = 5.9 Hz, 2H), 3.91-3.57 (m, 4H), 3.34-3.19 (m, 2H), 1.46 (s, 9H). |
| 46 | 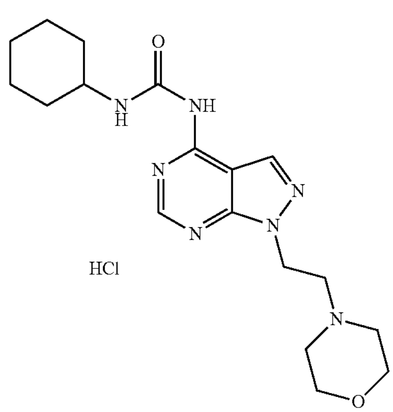 [SMILES: O=C(Nc1ncnc2c1cnn2CCN1CCOCC1)NC1CCCCC1 ; Cl] | 1-Cyclohexyl-3-(1-(2-morpholinoethyl)-1H-pyrazolo[3,4-d]pyrimidin-4-yl)urea hydrochloride | $^1$H NMR (CD$_3$OD) δ ppm: 8.66 (s, 1H), 8.58 (s, 1H), 4.97 (t, J = 5.9 Hz, 2H), 4.20-3.98 (m, 2H), 3.84 (t, J = 5.9 Hz, 2H), 3.88-3.60 (m, 4H), 3.38-3.17 (m, 2H), 2.05-1.91 (m, 1H), 1.90-1.57 (m, 4H), 1.55-1.08 (m, 6H). |

-continued

| Ex. | Structure | Name | NMR |
|---|---|---|---|
| 47 | 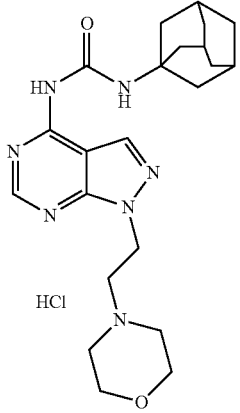 [SMILES: O=C(Nc1ncnc2c1cnn2CCN1CCOCC1)NC12CC3CC(CC(C3)C1)C2 ; Cl] | 1-Adamanthyl-3-(1-(2-morpholinoethyl)-1H-pyrazolo[3,4-d]pyrimidin-4-yl)urea hydrochloride | $^1$H NMR (CD$_3$OD) δ ppm: 8.64 (s, 1H), 8.58 (s, 1H), 4.97 (t, J = 5.9 Hz, 2H), 4.17-3.98 (m, 2H), 3.84 (t, J = 5.9 Hz, 2H), 3.93-3.59 (m, 4H), 3.41-3.15 (m, 2H), 2.23-2.03 (m, 9H), 1.86-1.69 (m, 6H). |
| 48 | 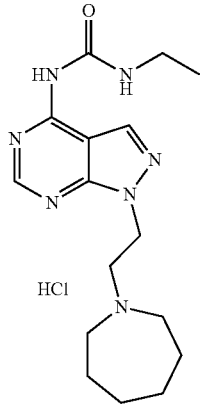 [SMILES: CCNC(=O)Nc1ncnc2c1cnn2CCN1CCCCCC1 ; Cl] | 1-(1-(2-(Azepan-1-yl)ethyl)-1H-pyrazolo[3,4-d]pyrimidin-4-yl)-3-ethylurea hydrochloride | $^1$H NMR (CD$_3$OD) δ ppm: 8.67 (s, 1H), 8.59 (s, 1H), 4.95 (t, J = 6.0 Hz, 2H), 3.83 (t, J = 6.0 Hz, 2H), 3.69-3.56 (m, 2H), 3.47-3.35 (m, 4H), 2.15-1.84 (m, 4H), 1.84-1.69 (m, 4H), 1.25 (t, J = 7.2 Hz, 3H). |
| 49 | 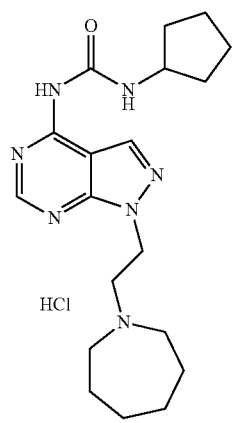 [SMILES: O=C(Nc1ncnc2c1cnn2CCN1CCCCCC1)NC1CCCC1 ; Cl] | 1-(1-(2-(Azepan-1-yl)ethyl)-1H-pyrazolo[3,4-d]pyrimidin-4-yl)-3-cyclopentylurea hydrochloride | $^1$H NMR (CD$_3$OD) δ ppm: 8.67 (s, 1H), 8.61 (s, 1H), 4.95 (t, J = 5.9 Hz, 2H), 4.31-4.13 (m, 1H), 3.83 (t, J = 6.0 Hz, 2H), 3.69-3.55 (m, 2H), 3.40-3.29 (m, 2H), 2.18-1.86 (m, 6H), 1.86-1.49 (m, 10H). |

-continued

| Ex. | Structure | Name | NMR |
|---|---|---|---|
| 50 | 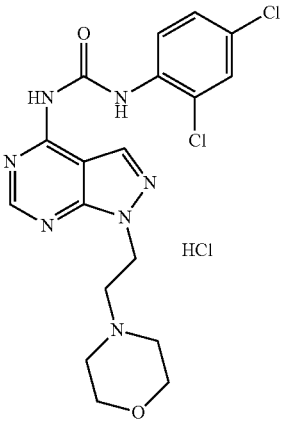 [SMILES: O=C(Nc1ccc(Cl)cc1Cl)Nc1ncnc2c1cnn2CCN1CCOCC1 ; Cl] | 1-(2,4-Dichlorophenyl)-3-(1-(2-morpholinoethyl)-1H-pyrazolo[3,4-d]pyrimidin-4-yl)urea hydrochloride | $^1$H NMR (DMSO-d$_6$) δ ppm: 11.3 (s, 1H), 10.1 (s, 1H), 8.75 (s, 1H), 8.6 (s, 1H), 8.4 (d, J = 8.9 Hz, 1H), 7.7 (d, J = 2.4 Hz, 1H), 7.45 (dd, J = 9.0 Hz, 2.5 Hz, 1H), 4.8 (m, 2H), 3.95 (m, 2H), 3.65 (m, 4H), 3.5 (m, 2H), 3.15 (m, 2H). |
| 51 | 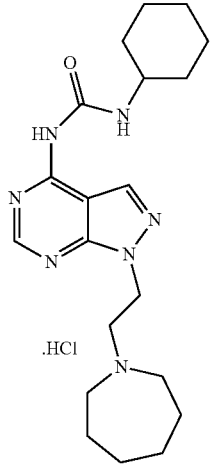 [SMILES: O=C(Nc1ncnc2c1cnn2CCN1CCCCCC1)NC1CCCCC1 ; ".HCl"] | 1-(1-(2-(Azepan-1-yl)ethyl)-1H-pyrazolo[3,4-d]pyrimidin-4-yl)-3-cyclohexylurea hydrochloride | $^1$H NMR (CD$_3$OD) δ ppm: 8.67 (s, 1H), 8.61 (s, 1H), 4.95 (t, J = 5.8 Hz, 2H), 3.83 (t, J = 5.9 Hz, 2H), 3.79-3.71 (m, 1H), 3.68-3.53 (m, 2H), 3.41-3.30 (m, 2H), 2.08-1.84 (m, 6H), 1.84-1.70 (m, 6H), 1.70-1.58 (m, 1H), 1.54-1.24 (m, 5H). |
| 52 | 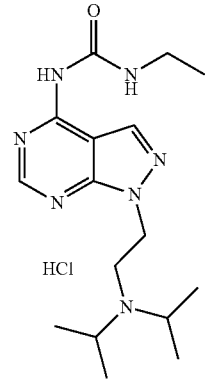 [SMILES: CCNC(=O)Nc1ncnc2c1cnn2CCN(C(C)C)C(C)C ; Cl] | 1-(1-(2-(Diisopropylamino)ethyl)-1H-pyrazolo[3,4-d]pyrimidin-4-yl)-3-ethylurea hydrochloride | $^1$H NMR (CD$_3$OD) δ ppm: 8.68 (s, 1H), 8.61 (s, 1H), 4.92 (t, J = 7.3 Hz, 2H), 3.90 (hept, J = 6.5 Hz, 2H), 3.75 (t, J = 7.3 Hz, 2H), 3.40 (q, J = 7.2 Hz, 2H), 1.46 (d, J = 6.5 Hz, 12H), 1.25 (t, J = 7.2 Hz, 3H). |

-continued

| Ex. | Structure | Name | NMR |
|---|---|---|---|
| 53 | 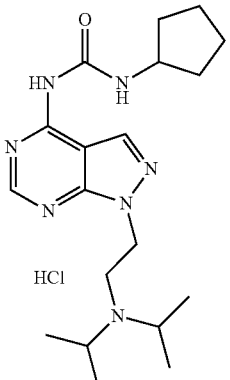 | 1-Cyclopentyl-3-(1-(2-(diisopropylamino)ethyl)-1H-pyrazolo[3,4-d]pyrimidin-4-yl)urea hydrochloride | $^1$H NMR (CD$_3$OD) δ ppm: 8.65 (s, 1H), 8.6 (s, 1H), 4.95 (t, J = 7.3 Hz, 2H), 4.2 (m, 1H), 3.9 (m, 2H), 3.75 (t, J = 7.4 Hz, 2H), 2.05 (m, 2H), 1.65-1.45 (m, 6H), 1.45 (d, J = 6.6 Hz, 12H). |
| 54 | 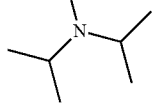 | 1-Cyclopentyl-3-(1-(2-(piperidin-1-yl)ethyl)-1H-pyrazolo[3,4-d]pyrimidin-4-yl)urea hydrochloride | $^1$H NMR (CD$_3$OD) δ ppm: 8.65 (s, 1H), 8.6 (s, 1H), 4.95 (t, J = 6.0 Hz, 2H), 4.2 (m, 1H), 3.75 (m, 4H), 3.05 (t, J = 12.4 Hz, 2H), 2.05 (m, 4H), 1.95-1.5 (m, 10H). |
| 55 | 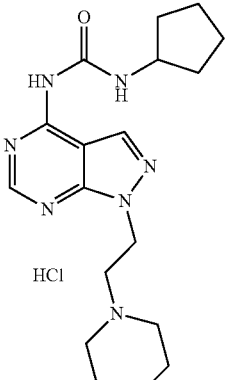 | 1-Ethyl-3-(1-(2-(piperidin-1-yl)ethyl)-1H-pyrazolo[3,4-d]pyrimidin-4-yl)urea hydrochloride | $^1$H NMR (CD$_3$OD) δ ppm: 8.65 (s, 1H), 8.6 (s, 1H), 4.95 (t, J = 5.9 Hz, 2H), 3.75 (m, 4H), 3.4 (q, J = 7.2 Hz, 2H), 3.05 (t, J = 11.0 Hz, 2H), 2.0 (m, 2H), 1.8 (m, 3H), 1.55 (m, 1H), 1.25 (t, J = 7.2 Hz, 3H). |
| 56 | 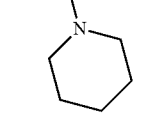 | 1-Adamanthyl-3-(1-(2-(piperidin-1-yl)ethyl)-1H-pyrazolo[3,4-d]pyrimidin-4-yl)urea hydrochloride | $^1$H NMR (CD$_3$OD) δ ppm: 8.65 (s, 1H), 8.6 (s, 1H), 4.95 (t, J = 5.9 Hz, 2H), 3.75 (m, 4H), 3.05 (t, J = 12.3 Hz, 2H), 2.15 (m, 9H), 2.0 (m, 2H), 1.55 (m, 10H). |

| Ex. | Structure | Name | NMR |
|---|---|---|---|
| 57 | 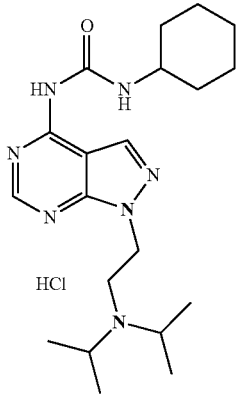 [SMILES: CC(C)N(CCn1ncc2c(NC(=O)NC3CCCCC3)ncnc21)C(C)C ; Cl] | 1-Cyclohexyl-3-(1-(2-(diisopropylamino)ethyl)-1H-pyrazolo[3,4-d]pyrimidin-4-yl)urea hydrochloride | $^1$H NMR (CD$_3$OD) δ ppm: 8.65 (s, 1H), 8.52 (s, 1H), 4.89 (t, J = 7.2 Hz, 2H), 3.91 (hept, J = 6.6 Hz, 2H), 3.75 (t, J = 7.2 Hz, 2H), 3.72-3.56 (m, 1H), 2.09-1.89 (m, 2H), 1.89-1.75 (m, 2H), 1.73-1.56 (m, 1H), 1.45 (dd, J = 6.5, 1.6 Hz, 12H), 1.62-1.20 (m, 5H). |
| 58 | 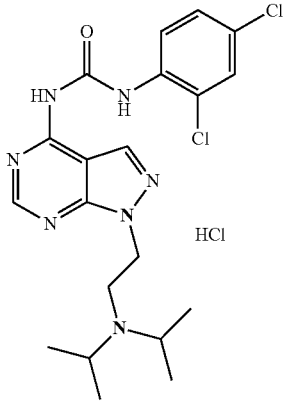 [SMILES: CC(C)N(CCn1ncc2c(NC(=O)Nc3ccc(Cl)cc3Cl)ncnc21)C(C)C ; Cl] | 1-(2,4-Dichlorophenyl)-3-(1-(2-(diisopropylamino)ethyl)-1H-pyrazolo[3,4-d]pyrimidin-4-yl)urea hydrochloride | $^1$H NMR (CD$_3$OD) δ ppm: 8.74 (s, 1H), 8.53 (s, 1H), 8.35 (d, J = 8.9 Hz, 1H), 7.56 (d, J = 1.8 Hz, 1H), 7.36 (dd, J = 8.7, 2.1 Hz, 1H), 4.90 (t, J = 7.2 Hz, 2H), 3.91 (hept, J = 6.7 Hz, 2H), 3.76 (t, J = 7.2 Hz, 2H), 1.46 (d, J = 6.4 Hz, 12H). |
| 59 | 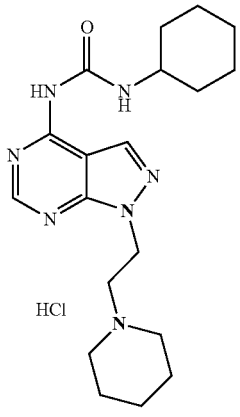 [SMILES: O=C(Nc1ncnc2c1cnn2CCN1CCCCC1)NC1CCCCC1 ; Cl] | 1-Cyclohexyl-3-(1-(2-(piperidin-1-yl)ethyl)-1H-pyrazolo[3,4-d]pyrimidin-4-yl)urea hydrochloride | $^1$H NMR (CD$_3$OD) δ ppm: 8.65 (s, 1H), 8.55 (s, 1H), 4.95 (t, J = 6.0 Hz, 2H), 3.75 (m, 4H), 3.1 (t, J = 12.3 Hz, 2H), 2.0 (m, 4H), 1.85-1.15 (m, 13H). |

-continued

| Ex. | Structure | Name | NMR |
|---|---|---|---|
| 60 | 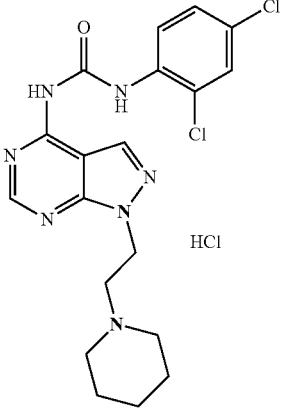 [SMILES: O=C(Nc1ccc(Cl)cc1Cl)Nc1ncnc2c1cnn2CCN1CCCCC1 ; Cl] | 1-(2,4-Dichlorophenyl)-3-(1-(2-(piperidin-1-yl)ethyl)-1H-pyrazolo[3,4-d]pyrimidin-4-yl)urea hydrochloride | $^1$H NMR (CD$_3$OD) δ ppm: 8.75 (s, 1H), 8.55 (s, 1H), 8.35 (d, J = 8.9 Hz, 1H), 7.55 (d, J = 2.3 Hz, 1H), 7.4 (dd, J = 8.9 Hz, 2.4 Hz, 1H), 4.95 (t, J = 6.0 Hz, 2H), 3.75 (m, 4H), 3.1 (t, J = 12.3 Hz, 2H), 2.0 (m, 2H), 1.9-1.75 (m, 3H), 1.55 (m, 1H). |
| 61 | 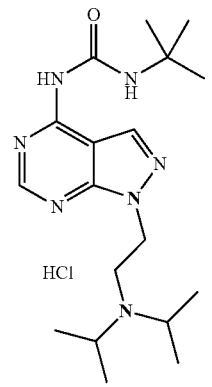 [SMILES: CC(C)N(CCn1ncc2c(NC(=O)NC(C)(C)C)ncnc21)C(C)C ; Cl] | 1-tert-Butyl-3-(1-(2-(diisopropylamino)ethyl)-1H-pyrazolo[3,4-d]pyrimidin-4-yl)urea hydrochloride | $^1$H NMR (CD$_3$OD) δ ppm: 8.63 (s, 1H), 8.55 (s, 1H), 4.97-4.84 (m, 2H), 3.90 (hept, J = 6.6 Hz, 2H), 3.78-3.71 (m, 2H), 1.46 (s, 9H), 1.45 (d, J = 6.5 Hz, 12H). |
| 62 | 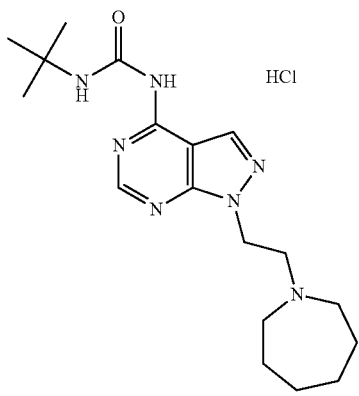 [SMILES: CC(C)(C)NC(=O)Nc1ncnc2c1cnn2CCN1CCCCCC1 ; Cl] | 1-(1-(2-(azepan-1-yl)ethyl)-1H-pyrazolo[3,4-d]pyrimidin-4-yl)-3-tert-butylurea hydrochloride | $^1$H NMR (DMSO-d$_6$) δ ppm: 10.25 (s, 1H), 8.98 (s, 1H), 8.61 (s, 1H), 8.58 (s, 1H), 4.82 (t, J = 6.3 Hz, 2H), 3.50-3.34 (m, 4H), 3.26-3.07 (m, 2H), 1.87-1.73 (m, 4H), 1.71-1.50 (m, 4H), 1.38 (s, 9H). |
| 63 | 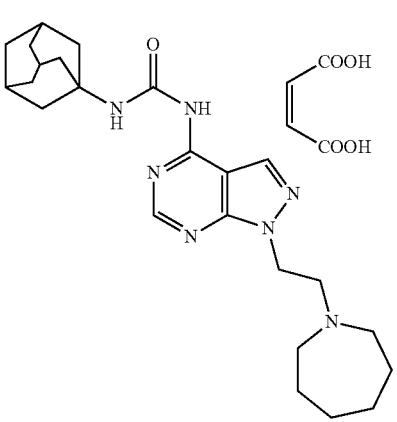 | 1-Adamanthyl-3-(1-(2-(azepan-1-yl)ethyl)-1H-pyrazolo[3,4-d]pyrimidin-4-yl)urea maleate | $^1$H NMR (CD$_3$OD) δ ppm: 8.57 (s, 1H), 8.45 (s, 1H), 6.26 (s, 2H), 4.85 (t, J = 5.9 Hz, 2H), 3.79 (t, J = 5.9 Hz, 2H), 3.70-3.07 (m, 4H), 2.22-2.04 (m, 9H), 2.04-1.86 (m, 4H), 1.86-1.61 (m, 10H). |

-continued

| Ex. | Structure | Name | NMR |
|---|---|---|---|
| 64 | 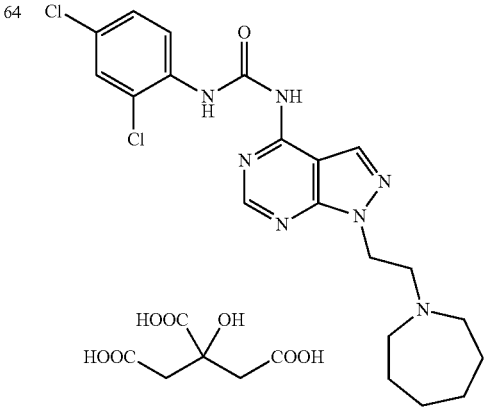 | 1-(1-(2-(azepan-1-yl)ethyl)-1H-pyrazolo[3,4-d]pyrimidin-4-yl)-3-(2,4-dichlorophenyl)urea citrate | $^1$H NMR (CD$_3$OD) δ ppm: 7.89 (s, 1H), 7.65 (s, 1H), 7.56 (d, J = 9.0 Hz, 1H), 6.74 (d, J = 2.3 Hz, 1H), 6.54 (dd, J = 9.0, 2.4 Hz, 1H), 3.99 (t, J = 6.1 Hz, 2H), 2.84 (t, J = 6.0 Hz, 2H), 2.68-2.35 (m, 4H), 1.97 (q, J = 15.4 Hz, 4H), 1.20-0.97 (m, 4H), 0.97-0.76 (m, 4H). |
| 65 | 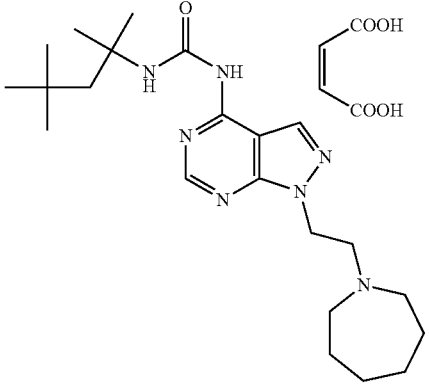 | 1-(1-(2-(azepan-1-yl)ethyl)-1H-pyrazolo[3,4-d]pyrimidin-4-yl)-3-(2,4,4-trimethylpentan-2-yl)urea maleate | $^1$H NMR (CD$_3$OD) δ ppm: 8.58 (s, 1H), 8.44 (s, 1H), 6.24 (s, 2H), 4.84 (t, J = 5.8 Hz, 2H), 3.70 (t, J = 5.8 Hz, 2H), 3.43-3.34 (m, 4H), 1.99-1.82 (m, 4H), 1.87 (s, 2H), 1.81-1.60 (m, 4H), 1.51 (s, 6H), 1.05 (s, 9H). |
| 66 | 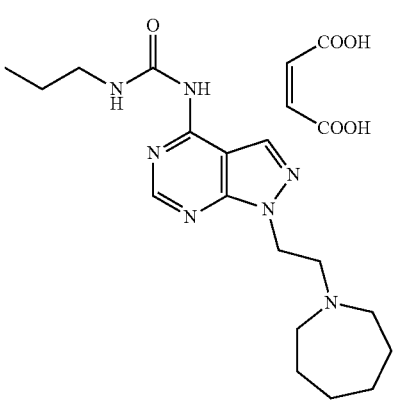 | 1-(1-(2-(azepan-1-yl)ethyl)-1H-pyrazolo[3,4-d]pyrimidin-4-yl)-3-propylurea maleate | $^1$H NMR (CD$_3$OD) δ ppm: 8.60 (s, 1H), 8.44 (s, 1H), 6.27 (s, 2H), 4.87 (t, J = 5.9 Hz, 2H), 3.79 (t, J = 5.9 Hz, 2H), 3.69-3.12 (m, 4H), 3.38-3.32 (m, 2H), 2.03-1.85 (m, 4H), 1.85-1.71 (m, 4H), 1.71-1.57 (m, 2H), 1.01 (t, J = 7.4 Hz, 3H). |

| Ex. | Structure | Name | NMR |
|---|---|---|---|
| 67 | 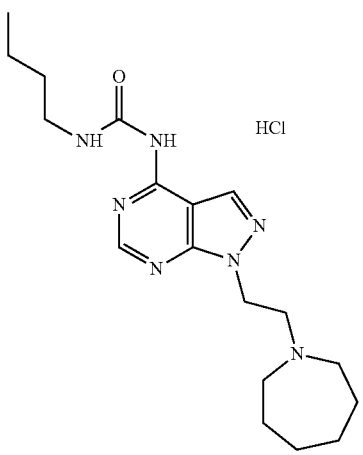 [SMILES: CCCCNC(=O)Nc1ncnc2c1cnn2CCN1CCCCCC1 ; Cl] | 1-(1-(2-(azepan-1-yl)ethyl)-1H-pyrazolo[3,4-d]pyrimidin-4-yl)-3-butylurea hydrochloride | $^1$H NMR (CD$_3$OD) δ ppm: 8.67 (s, 1H), 8.60 (s, 1H), 4.95 (t, J = 6.0 Hz, 2H), 3.83 (t, J = 6.0 Hz, 2H), 3.69-3.54 (m, 2H), 3.45-3.33 (m, 2H), 3.37 (t, J = 7.0 Hz, 2H), 2.05-1.86 (m, 4H), 1.82-1.71 (m, 4H), 1.69-1.54 (m, 2H), 1.44 (dq, J = 14.2, 7.1 Hz, 2H), 0.99 (t, J = 7.3 Hz, 3H). |
| 68 | 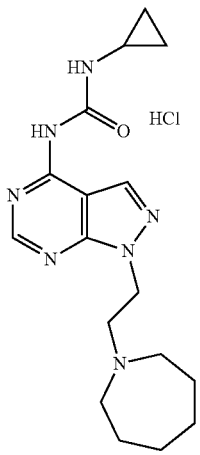 [SMILES: O=C(Nc1ncnc2c1cnn2CCN1CCCCCC1)NC1CC1 ; Cl] | 1-(1-(2-(azepan-1-yl)ethyl)-1H-pyrazolo[3,4-d]pyrimidin-4-yl)-3-cyclopropylurea hydrochloride | $^1$H NMR (CD$_3$OD) δ ppm: 8.65 (s, 1H), 8.57 (s, 1H), 4.93 (t, J = 5.9 Hz, 2H), 3.82 (t, J = 5.9 Hz, 2H), 3.74-3.49 (m, 2H), 3.43-3.28 (m, 2H), 2.91-2.67 (m, 1H), 2.09-1.82 (m, 4H), 1.85-1.68 (m, 4H), 0.94-0.75 (m, 2H), 0.73-0.57 (m, 2H). |
| 69 | 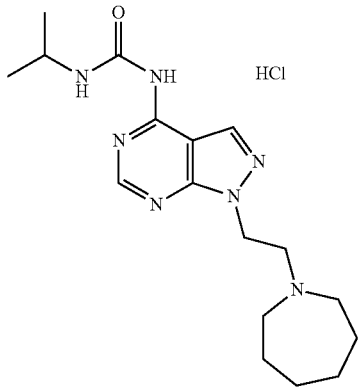 [SMILES: CC(C)NC(=O)Nc1ncnc2c1cnn2CCN1CCCCCC1 ; Cl] | 1-(1-(2-(azepan-1-yl)ethyl)-1H-pyrazolo[3,4-d]pyrimidin-4-yl)-3-isopropylurea hydrochloride | $^1$H NMR (CD$_3$OD) δ ppm: 8.67 (s, 1H), 8.61 (s, 1H), 4.95 (t, J = 6.0 Hz, 2H), 4.04 (hept, J = 6.6 Hz, 1H), 3.83 (t, J = 6.0 Hz, 2H), 3.74-3.52 (m, 2H), 3.43-3.26 (m, 2H), 2.11-1.84 (m, 4H), 1.84-1.63 (m, 4H), 1.29 (d, J = 6.6 Hz, 6H). |

| Ex. | Structure | Name | NMR |
|---|---|---|---|
| 70 | 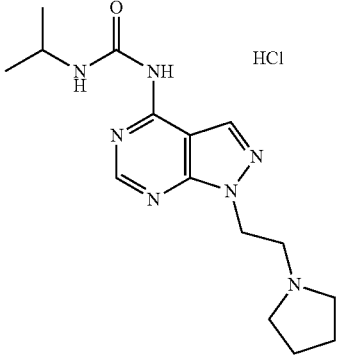 [SMILES: CC(C)NC(=O)Nc1ncnc2c1cnn2CCN1CCCC1 ; Cl] HCl | 1-isopropyl-3-(1-(2-(pyrrolidin-1-yl)ethyl)-1H-pyrazolo[3,4-d]pyrimidin-4-yl)urea hydrochloride | $^1$H NMR (CD$_3$OD) δ ppm: 8.67 (s, 1H), 8.61 (s, 1H), 4.92 (t, J = 5.7 Hz, 2H), 4.04 (hept, J = 6.6 Hz, 1H), 3.87 (d, J = 5.7 Hz, 2H), 3.82-3.69 (m, 2H), 3.26-3.09 (m, 2H), 2.30-2.10 (m, 2H), 2.10-1.89 (m, 2H), 1.29 (d, J = 6.6 Hz, 6H). |
| 71 | 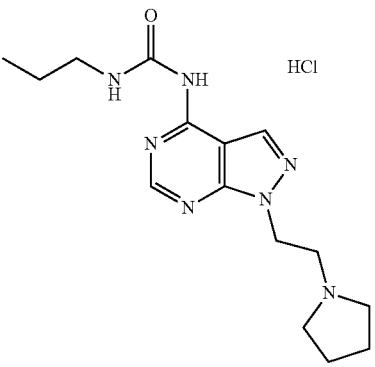 [SMILES: CCCNC(=O)Nc1ncnc2c1cnn2CCN1CCCC1 ; Cl] HCl | 1-propyl-3-(1-(2-(pyrrolidin-1-yl)ethyl)-1H-pyrazolo[3,4-d]pyrimidin-4-yl)urea hydrochloride | $^1$H NMR (CD$_3$OD) δ ppm: 8.67 (s, 1H), 8.60 (s, 1H), 4.92 (t, J = 5.7 Hz, 2H), 3.87 (t, J = 5.7 Hz, 2H), 3.81-3.72 (m, 2H), 3.32 (t, J = 6.9 Hz, 2H), 3.27-3.08 (m, 2H), 2.27-2.09 (m, 2H), 2.09-1.95 (m, 2H), 1.79-1.51 (m, 2H), 1.01 (t, J = 7.4 Hz, 3H). |
| 72 | 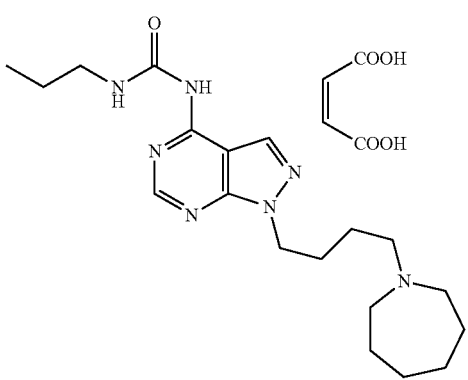 COOH COOH | 1-(1-(4-(azepan-1-yl)butyl)-1H-pyrazolo[3,4-d]pyrimidin-4-yl)-3-propylurea maleate | $^1$H NMR (CD$_3$OD) δ ppm: 8.56 (s, 1H), 8.36 (s, 1H), 6.25 (s, 2H), 4.50 (t, J = 6.7 Hz, 3H), 3.41-3.30 (m, 2H), 3.13-3.00 (m, 4H), 3.00-2.86 (m, 2H), 2.08-1.91 (m, 2H), 1.87-1.73 (m, 4H), 1.73-1.52 (m, 8H), 1.01 (t, J = 7.4 Hz, 3H). |
| 73 | 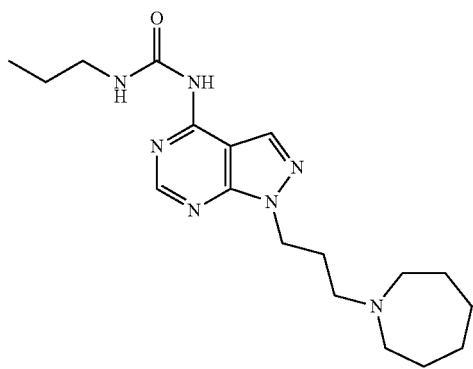 [SMILES: CCCNC(=O)Nc1ncnc2c1cnn2CCCN1CCCCCC1] | 1-(1-(3-(azepan-1-yl)propyl)-1H-pyrazolo[3,4-d]pyrimidin-4-yl)-3-propylurea | $^1$H NMR (CD$_3$OD) δ ppm: 8.55 (s, 1H), 8.34 (s, 1H), 4.48 (t, J = 6.8 Hz, 2H), 3.44-3.28 (m, 2H), 2.69-2.58 (m, 4H), 2.58-2.46 (m, 2H), 2.24-2.01 (m, 2H), 1.78-1.48 (m, 10H), 1.02 (t, J = 7.4 Hz, 3H). |

| Ex. | Structure | Name | NMR |
|---|---|---|---|
| 74 | 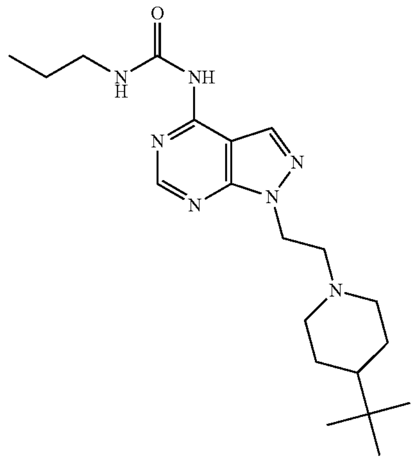 [SMILES: CCCNC(=O)Nc1ncnc2c1cnn2CCN1CCC(C(C)(C)C)CC1] | 1-(1-(2-(4-tert-butylpiperidin-1-yl)ethyl)-1H-pyrazolo[3,4-d]pyrimidin-4-yl)-3-propylurea | $^1$H NMR (CD$_3$OD) δ ppm: 8.55 (s, 1H), 8.34 (s, 1H), 4.59 (t, J = 6.8 Hz, 2H), 3.43-3.29 (m, 2H), 3.19-3.01 (m, 2H), 2.88 (t, J = 6.8 Hz, 2H), 2.15-1.93 (m, 2H), 1.76-1.53 (m, 4H), 1.44-1.16 (m, 2H), 1.01 (t, J = 7.4 Hz, 3H), 0.85 (s, 9H). |

Example 75

Synthesis of 1-(1-(2-(azepan-1-yl)ethyl)-1H-pyrazolo[3,4-d]pyrimidin-4-yl)-3-butylthiourea maleate

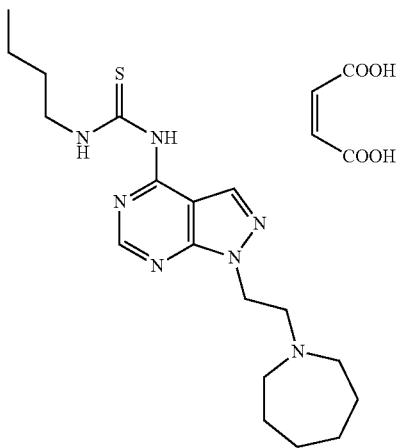 [SMILES: CCCCNC(=S)Nc1ncnc2c1cnn2CCN1CCCCCC1 ; O=C(O)/C=C\C(=O)O]

1-(2-(azepan-1-yl)ethyl)-1H-pyrazolo[3,4-d]pyrimidin-4-amine (0.100 g, 0.384 mmol), propyl thioisocyanate (0.133 g, 1.154 mmol) in 4 mL of toluene were heated in CEM microwave reactor for 60 min. at 150° C. The mixture was concentrated under reduced pressure, purified by flash chromatography (EtOAc) treated with acetonitrile and filtered to afford 23 mg of a white solid. To an ice-cooled stirred solution of 1-(1-(2-(azepan-1-yl)ethyl)-1H-pyrazolo[3,4-d]pyrimidin-4-yl)-3-butylthiourea in 0.5 mL of MeOH, 7.5 mg of maleic acid in 0.5 mL of MeOH was added dropwise. After stirring for 15 minutes at rt, the solid was filtered, and the residue washed with diethyl ether to obtain 26 mg of 1-(1-(2-(azepan-1-yl)ethyl)-1H-pyrazolo[3,4-d]pyrimidin-4-yl)-3-butylthiourea maleate. $^1$H NMR (CD$_3$OD) δ ppm: 8.63 (s, 1H), 8.53 (s, 1H), 6.24 (s, 2H), 4.89 (t, J=5.9 Hz, 2H), 3.79 (t, J=5.9 Hz, 2H), 3.75 (t, J=7.1 Hz, 2H), 3.57-3.39 (m, 4H), 2.01-1.85 (m, 4H), 1.85-1.65 (m, 6H), 1.49 (dq, J=14.3, 7.3 Hz, 2H), 1.01 (t, J=7.3 Hz, 3H).

Examples (76-79) were prepared following the same method as example 75:

| Ex. | Structure | Name | NMR |
|---|---|---|---|
| 76 | 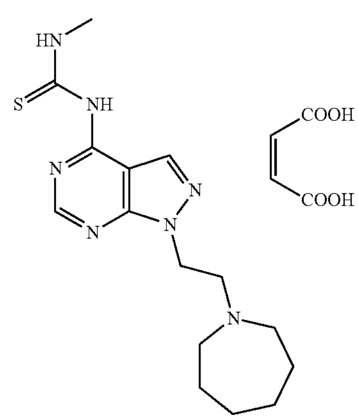 [SMILES: CNC(=S)Nc1ncnc2c1cnn2CCN1CCCCCC1 ; O=C(O)/C=C\C(=O)O] | 1-(1-(2-(azepan-1-yl)ethyl)-1H-pyrazolo[3,4-d]pyrimidin-4-yl)-3-methylthiourea maleate | $^1$H NMR (CD$_3$OD) δ ppm: 8.63 (s, 1H), 8.53 (s, 1H), 6.25 (s, 2H), 4.89 (t, J = 5.9 Hz, 2H), 3.79 (t, J = 5.9 Hz, 2H), 3.66-2.99 (m, 4H), 3.25 (s, 3H), 2.06-1.83 (m, 4H), 1.83-1.66 (m, 4H). |

-continued

| Ex. | Structure | Name | NMR |
|---|---|---|---|
| 77 | 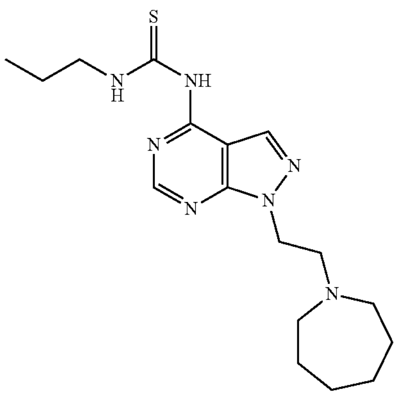 | 1-(1-(2-(azepan-1-yl)ethyl)-1H-pyrazolo[3,4-d]pyrimidin-4-yl)-3-propylthiourea | $^1$H NMR (CDCl$_3$) δ ppm: 12.01-11.72 (m, 1H), 8.54 (s, 1H), 8.35 (s, 1H), 8.05 (s, 1H), 4.63-4.43 (m, 2H), 3.74 (dd, J = 12.4, 6.9 Hz, 2H), 3.23-2.99 (m, 2H), 2.89-2.53 (m, 4H), 1.95-1.72 (m, 2H), 1.62-1.44 (m, 8H), 1.07 (t, J = 7.4 Hz, 3H). |
| 78 | 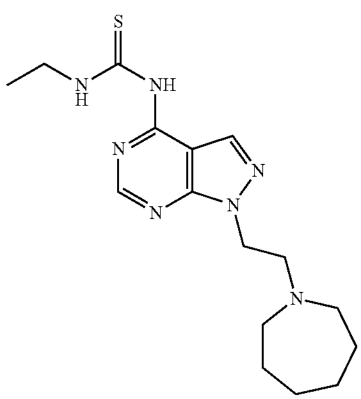 [SMILES: CCNC(=S)Nc1ncnc2c1cnn2CCN1CCCCCC1] | 1-(1-(2-(azepan-1-yl)ethyl)-1H-pyrazolo[3,4-d]pyrimidin-4-yl)-3-ethylthiourea | $^1$H NMR (CD$_3$OD) δ ppm: 8.58 (s, 1H), 8.43 (s, 1H), 4.57 (t, J = 6.6 Hz, 2H), 3.77 (q, J = 7.3 Hz, 2H), 3.10 (t, J = 6.6 Hz, 2H), 2.87-2.62 (m, 4H), 1.73-1.47 (m, 8H), 1.34 (t, J = 7.3 Hz, 3H). |
| 79 | 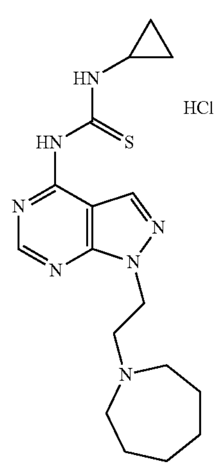 [SMILES: S=C(Nc1ncnc2c1cnn2CCN1CCCCCC1)NC1CC1 ; Cl] | 1-(1-(2-(azepan-1-yl)ethyl)-1H-pyrazolo[3,4-d]pyrimidin-4-yl)-3-cyclopropylthiourea hydrochloride | $^1$H NMR (CD$_3$OD) δ ppm: 8.63 (s, 1H), 8.54 (s, 1H), 4.90 (t, J = 5.9 Hz, 2H), 3.80 (t, J = 5.9 Hz, 2H), 3.72-3.52 (m, 2H), 3.34-3.11 (m, 1H), 3.43-3.08 (m, 2H), 2.21-1.82 (m, 4H), 1.82-1.66 (m, 4H), 1.08-0.85 (m, 2H), 0.85-0.69 (m, 2H). |

Example 80

Synthesis of 2,4-Dichloro-N-(1-(2-(diisopropylamino)ethyl)-1H-pyrazolo[3,4-d]pyrimidin-4-yl)benzenesulfonamide hydrochloride

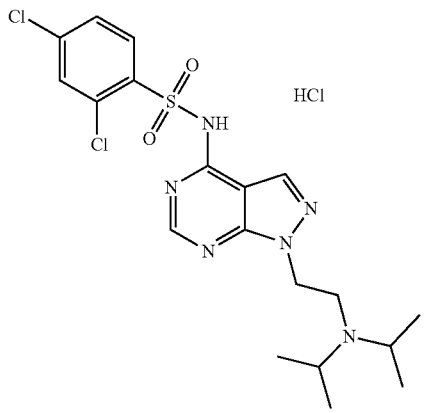 [SMILES: CC(C)N(CCn1ncc2c(NS(=O)(=O)c3ccc(Cl)cc3Cl)ncnc21)C(C)C ; Cl]

To a solution of NaH (9.15 mg, 0.381 mmol) in 3 ml of anhydrous DMF, was added dropwise a solution of 1-(2-(diisopropylamino)ethyl)-1H-pyrazolo[3,4-d]pyrimidin-4-amine (100 mg, 0.381 mmol) in 2 mL of anhydrous DMF at 0° C. The mixture was stirred at 50° C. for 1 h. Then, sulfonyl chloride (98 mg, 0.400 mmol) in 1 ml anhydrous DMF was added and the mixture was heated at 60° C. for 26 h. The reaction mixture was cooled to rt and stirred for two additional days, 1 ml water was added and the solvent evaporated to dryness. The crude was partitioned between EtOAc and water. The organic layer was dried and evaporated under vacuum and purified by flash chromatography (EtOAc/MeOH=10:1). 1 ml of a 4M solution of dioxane-.HCl was added to a solution of 1 in 1.5 ml of anhydrous DCM, at 0° C. After 15 minutes the product was evaporated to dryness, treated with diethyl ether, and filtered to obtain 15 mg of a white solid. $^1$H NMR (CD$_3$OD) δ ppm: 8.54 (s, 1H), 8.31 (s, 1H), 8.18 (d, J=8.5 Hz, 1H), 7.68 (d, J=1.9 Hz, 1H), 7.54 (dd, J=8.5, 2.0 Hz, 1H), 4.81 (t, J=7.2 Hz, 2H), 3.90 (hept, J=6.6 Hz, 2H), 3.73 (t, J=7.2 Hz, 2H), 1.44 (d, J=6.6 Hz, 12H).

Example (81) was prepared following same method as example 80:

| Ex. | Structure | Name | NMR |
|---|---|---|---|
| 81 | 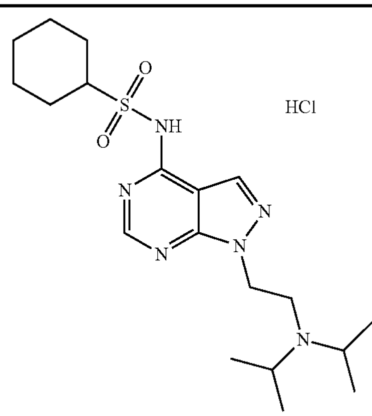 | N-(1-(2-(Diisopropylamino)ethyl)-1H-pyrazolo[3,4-d]pyrimidin-4-yl)cyclohexanesulfonamide hydrochloride | $^1$H NMR (CD$_3$OD) δ ppm: 8.53 (s, 1H), 8.24 (s, 1H), 4.79 (t, J = 7.2 Hz, 2H), 3.89 (hept, J = 6.6 Hz, 2H), 3.78-3.63 (m, 3H), 3.11-2.94 (m, 1H), 2.36-2.22 (m, 2H), 1.98-1.84 (m, 2H), 1.81-1.68 (m, 1H), 1.68-1.49 (m, 2H), 1.44 (d, J = 6.6 Hz, 12H), 1.47-1.16 (m, 2H). |

Examples (82-88) were prepared following the same method as in example 1:

| Ex. | Structure | Name | NMR |
|---|---|---|---|
| 82 | 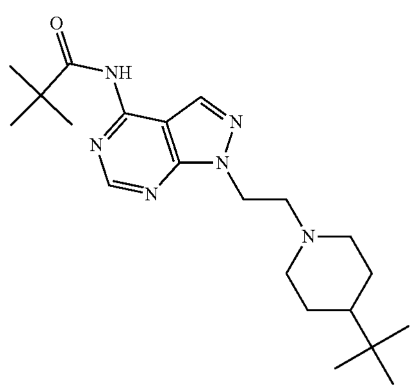 [SMILES: CC(C)(C)C(=O)Nc1ncnc2c1cnn2CCN1CCC(C(C)(C)C)CC1] | N-(1-(2-(4-tert-butylpiperidin-1-yl)ethyl)-1H-pyrazolo[3,4-d]pyrimidin-4-yl)pivalamide | $^1$H NMR (CD$_3$OD) δ ppm: 8.61 (s, 1H), 8.54 (s, 1H), 4.61 (t, J = 6.9 Hz, 2H), 3.09 (dt, J = 11.8, 3.1 Hz, 2H), 2.89 (t, J = 6.9 Hz, 2H), 2.02 (td, J = 12.0, 2.0 Hz, 2H), 1.75-1.59 (m, 2H), 1.38 (s, 9H), 1.26 (qd, J = 12.4, 3.7 Hz, 2H), 1.09-0.93 (m, 1H), 0.85 (s, 9H). |

| Ex. | Structure | Name | NMR |
|---|---|---|---|
| 83 | 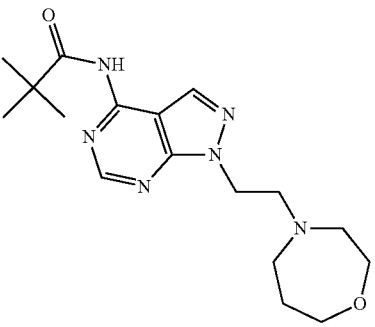 [SMILES: CC(C)(C)C(=O)Nc1ncnc2c1cnn2CCN1CCCOCC1] | N-(1-(2-(1,4-oxazepan-4-yl)ethyl)-1H-pyrazolo[3,4-d]pyrimidin-4-yl)pivalamide | $^1$H NMR (CDCl$_3$) δ ppm: 8.70 (s, 1H), 8.57 (s, 1H), 8.33 (s, 1H), 4.88-4.42 (m, 2H), 3.91-3.55 (m, 4H), 3.31-3.02 (m, 2H), 2.99-2.67 (m, 4H), 2.07-1.74 (m, 2H), 1.39 (s, 9H). |
| 84 | 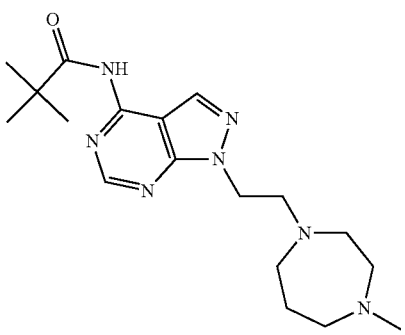 [SMILES: CN1CCCN(CCn2ncc3c(NC(=O)C(C)(C)C)ncnc32)CC1] | N-(1-(2-(4-methyl-1,4-diazepan-1-yl)ethyl)-1H-pyrazolo[3,4-d]pyrimidin-4-yl)pivalamide | $^1$H NMR (CDCl$_3$) δ ppm: 8.69 (s, 1H), 8.57 (s, 1H), 8.33 (s, 1H), 4.55 (t, J = 6.7 Hz, 2H), 3.08 (t, J = 6.7 Hz, 2H), 2.86-2.72 (m, 4H), 2.63-2.49 (m, 4H), 2.32 (s, 3H), 1.84-1.73 (m, 2H), 1.39 (s, 9H). |
| 85 | 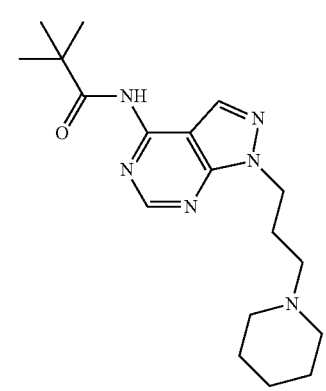 [SMILES: CC(C)(C)C(=O)Nc1ncnc2c1cnn2CCCN1CCCCC1] | N-(1-(3-(piperidin-1-yl)propyl)-1H-pyrazolo[3,4-d]pyrimidin-4-yl)pivalamide | $^1$H NMR (CD$_3$OD) δ ppm: 8.61 (s, 1H), 8.53 (s, 1H), 4.50 (t, J = 6.7 Hz, 2H), 2.53-2.33 (m, 6H), 2.24-2.07 (m, 2H), 1.65-1.50 (m, 4H), 1.50-1.42 (m, 2H), 1.38 (s, 9H). |
| 86 | 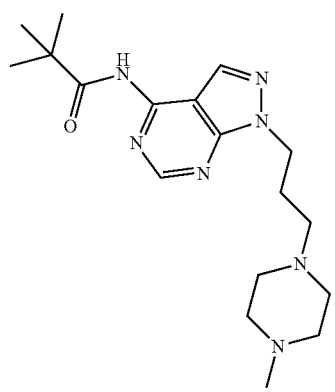 [SMILES: CN1CCN(CCCn2ncc3c(NC(=O)C(C)(C)C)ncnc32)CC1] | N-(1-(3-(4-methylpiperazin-1-yl)propyl)-1H-pyrazolo[3,4-d]pyrimidin-4-yl)pivalamide | $^1$H NMR (CD$_3$OD) δ ppm: 8.61 (s, 1H), 8.53 (s, 1H), 4.52 (t, J = 6.7 Hz, 2H), 2.85-2.30 (m, 10H), 2.25 (s, 3H), 2.17-2.05 (m, 2H), 1.38 (s, 9H). |

-continued

| Ex. | Structure | Name | NMR |
|---|---|---|---|
| 87 | 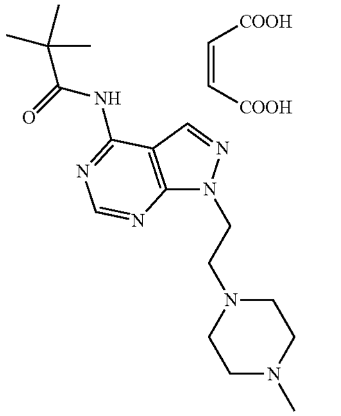 | N-(1-(2-(4-methylpiperazin-1-yl)ethyl)-1H-pyrazolo[3,4-d]pyrimidin-4-yl)pivalamide maleate | $^1$H NMR (CD$_3$OD) δ ppm: 8.60 (s, 1H), 8.53 (s, 1H), 6.28 (s, 4H), 4.61 (t, J = 6.0 Hz, 2H), 3.29-2.38 (m, 4H), 3.01 (t, J = 6.0 Hz, 2H), 2.80 (s, 3H), 1.37 (s, 9H). |
| 88 | 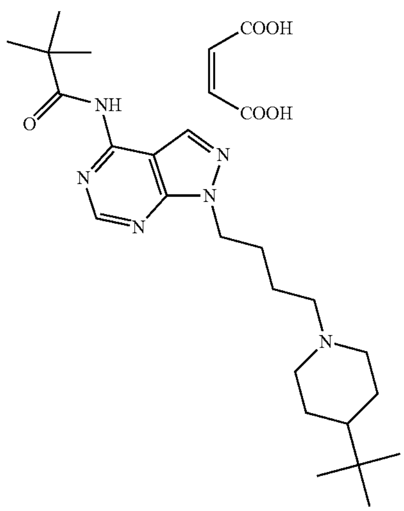 | N-(1-(4-(4-tert-butylpiperidin-1-yl)butyl)-1H-pyrazolo[3,4-d]pyrimidin-4-yl)pivalamide maleate | $^1$H NMR (CD$_3$OD) δ ppm: 8.63 (s, 1H), 8.55 (s, 1H), 6.25 (s, 2H), 4.54 (t, J = 6.6 Hz, 2H), 3.63-3.45 (m, 2H), 3.20-3.03 (m, 2H), 2.87 (t, J= 12.6 Hz, 2H), 2.12-1.88 (m, 4H), 1.79-1.63 (m, 2H), 1.57-1.42 (m, 3H), 1.38 (s, 9H), 0.91 (s, 9H). |

Examples (89-95) were prepared following the same method as in example 44:

| Ex. | Structure | Name | NMR |
|---|---|---|---|
| 89 | 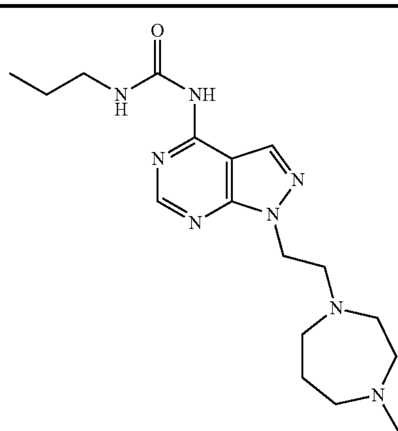 | 1-(1-(2-(4-methyl-1,4-diazepan-1-yl)ethyl)-1H-pyrazolo[3,4-d]pyrimidin-4-yl)-3-propylurea | $^1$H NMR (CD$_3$OD) δ ppm: 8.55 (s, 1H), 8.35 (s, 1H), 4.53 (t, J = 6.3 Hz, 2H), 3.41-3.32 (m, 2H), 3.06 (t, J = 6.4 Hz, 2H), 2.82-2.69 (m, 4H), 2.55-2.44 (m, 4H), 2.23 (s, 3H), 1.79-1.58 (m, 4H), 1.02 (t, J = 7.4 Hz, 3H). |

| Ex. | Structure | Name | NMR |
|---|---|---|---|
| 90 | 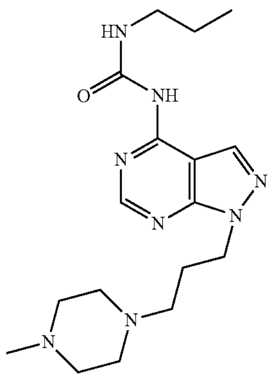 [SMILES: CCCNC(=O)Nc1ncnc2c1cnn2CCCN1CCN(C)CC1] | 1-(1-(3-(4-methylpiperazin-1-yl)propyl)-1H-pyrazolo[3,4-d]pyrimidin-4-yl)-3-propylurea | $^1$H NMR (CD$_3$OD) δ ppm: 8.55 (s, 1H), 8.34 (s, 1H), 4.49 (t, J = 6.7 Hz, 2H), 3.36-3.32 (m, 2H), 2.68-2.19 (m, 8H), 2.42-2.33 (m, 2H), 2.24 (s, 3H), 2.16-2.04 (m, 2H), 1.73-1.58 (m, 2H), 1.02 (t, J = 7.4 Hz, 4H). |
| 91 | 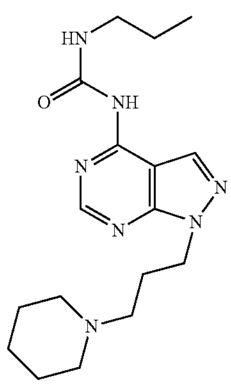 [SMILES: CCCNC(=O)Nc1ncnc2c1cnn2CCCN1CCCCC1] | 1-(1-(3-(piperidin-1-yl)propyl)-1H-pyrazolo[3,4-d]pyrimidin-4-yl)-3-propylurea | $^1$H NMR (CD$_3$OD) δ ppm: 8.55 (s, 1H), 8.34 (s, 1H), 4.48 (t, J = 6.7 Hz, 2H), 3.38-3.30 (m, 2H), 2.51-2.28 (m, 6H), 2.22-2.04 (m, 2H), 1.66 (h, J = 7.3 Hz, 2H), 1.56 (p, J = 5.6 Hz, 4H), 1.52-1.38 (m, 2H), 1.02 (t, J = 7.4 Hz, 3H). |
| 92 | 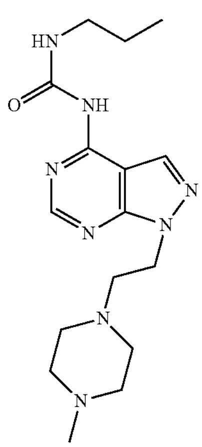 [SMILES: CCCNC(=O)Nc1ncnc2c1cnn2CCN1CCN(C)CC1] | 1-(1-(2-(4-methylpiperazin-1-yl)ethyl)-1H-pyrazolo[3,4-d]pyrimidin-4-yl)-3-propylurea | $^1$H NMR (CD$_3$OD) δ ppm: 8.54 (s, 1H), 8.34 (s, 1H), 4.58 (t, J = 6.5 Hz, 2H), 3.34 (t, J = 7.0 Hz, 2H), 2.91 (t, J = 6.5 Hz, 2H), 2.71-2.49 (m, 4H), 2.46-2.28 (m, 4H), 2.22 (s, 3H), 1.66 (h, J = 7.4 Hz, 2H), 1.02 (t, J = 7.4 Hz, 3H). |

| Ex. | Structure | Name | NMR |
|---|---|---|---|
| 93 | 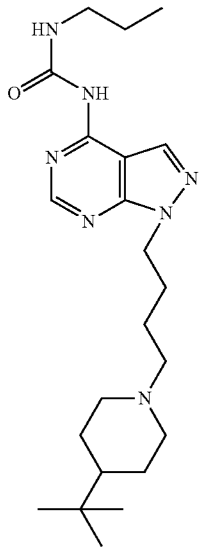 [SMILES: CCCNC(=O)Nc1ncnc2c1cnn2CCCCN1CCC(C(C)(C)C)CC1] | 1-(1-(4-(4-tert-butylpiperidin-1-yl)butyl)-1H-pyrazolo[3,4-d]pyrimidin-4-yl)-3-propylurea | $^1$H NMR (CD$_3$OD) δ ppm: 8.54 (s, 1H), 8.34 (s, 1H), 4.46 (t, J = 6.8 Hz, 2H), 3.36-3.31 (m, 2H), 3.03-2.93 (m, 2H), 2.42-2.34 (m, 2H), 1.93 (dt, J = 14.7, 6.9 Hz, 4H), 1.72-1.60 (m, 4H), 1.54-1.42 (m, 2H), 1.30 (qd, J = 12.7, 3.6 Hz, 2H), 1.09-1.04 (m, 1H), 1.01 (t, J = 7.4 Hz, 3H), 0.85 (s, 9H). |
| 94 | 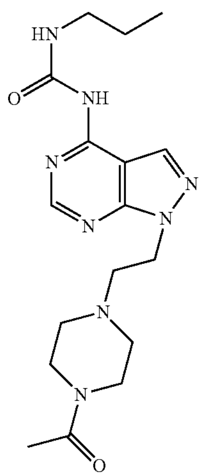 [SMILES: CCCNC(=O)Nc1ncnc2c1cnn2CCN1CCN(C(C)=O)CC1] | 1-(1-(2-(4-acetylpiperazin-1-yl)ethyl)-1H-pyrazolo[3,4-d]pyrimidin-4-yl)-3-propylurea | $^1$H NMR (CD$_3$OD) δ ppm: 8.55 (s, 1H), 8.35 (s, 1H), 4.59 (t, J = 6.3 Hz, 2H), 3.49-3.42 (m, 2H), 3.42-3.37 (m, 2H), 3.37-3.32 (m, 2H), 2.92 (t, J = 6.3 Hz, 2H), 2.58-2.52 (m, 2H), 2.52-2.46 (m, 2H), 2.05 (s, 3H), 1.66 (h, J = 7.4 Hz, 2H), 1.02 (t, J = 7.4 Hz, 3H). |
| 95 | 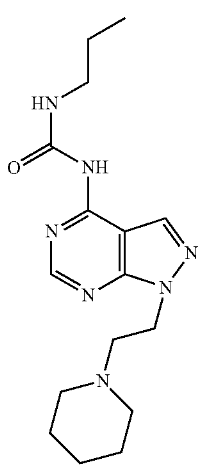 [SMILES: CCCNC(=O)Nc1ncnc2c1cnn2CCN1CCCCC1] | 1-(1-(2-(piperidin-1-yl)ethyl)-1H-pyrazolo[3,4-d]pyrimidin-4-yl)-3-propylurea | $^1$H NMR (CD$_3$OD) δ ppm: 8.54 (s, 1H), 8.34 (s, 1H), 4.58 (t, J = 6.8 Hz, 2H), 3.37-3.31 (m, 2H), 2.87 (t, J = 6.8 Hz, 2H), 2.55-2.46 (m, 4H), 1.65 (h, J = 7.3 Hz, 2H), 1.59-1.49 (m, 4H), 1.48-1.38 (m, 2H), 1.01 (t, J = 7.4 Hz, 3H). |

Examples (96-100) were prepared following same method as in example 80:

| Ex. | Structure | Name | NMR |
|---|---|---|---|
| 96 | 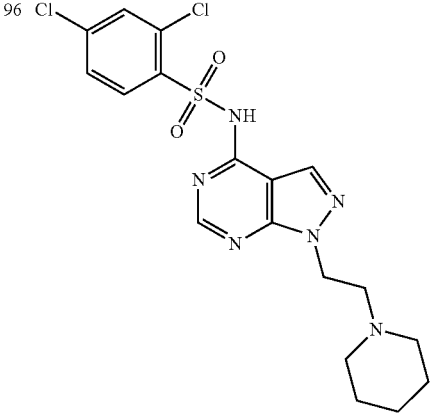 | 2,4-dichloro-N-(1-(2-(piperidin-1-yl)ethyl)-1H-pyrazolo[3,4-d]pyrimidin-4-yl)benzenesulfonamide | ¹H NMR (CDCl₃) δ ppm: 8.19 (d, J = 8.5 Hz, 1H), 8.13 (s, 1H), 8.08 (s, 1H), 7.50 (d, J = 2.1 Hz, 1H), 7.42 (dd, J = 8.6, 2.0 Hz, 1H), 4.92-4.42 (m, 2H), 3.23-2.95 (m, 2H), 2.81-2.32 (m, 4H), 1.92-1.17 (m, 6H). |
| 97 | 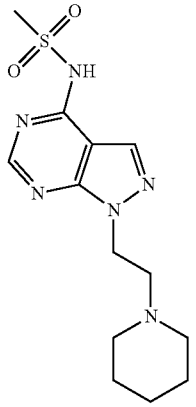 [SMILES: CS(=O)(=O)Nc1ncnc2c1cnn2CCN1CCCCC1] | N-(1-(2-(piperidin-1-yl)ethyl)-1H-pyrazolo[3,4-d]pyrimidin-4-yl)methanesulfonamide | ¹H NMR (CDCl₃) δ ppm: 8.21 (s, 1H), 8.02 (s, 1H), 4.50 (t, J = 6.8 Hz, 2H), 3.15 (s, 3H), 2.83 (t, J = 6.8 Hz, 2H), 2.45 (t, J = 5.2 Hz, 4H), 1.57-1.45 (m, 4H), 1.45-1.32 (m, 2H). |
| 98 | 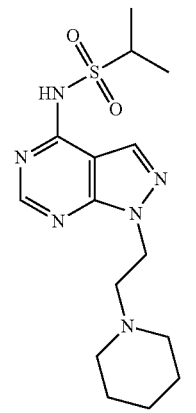 [SMILES: CC(C)S(=O)(=O)Nc1ncnc2c1cnn2CCN1CCCCC1] | N-(1-(2-(piperidin-1-yl)ethyl)-1H-pyrazolo[3,4-d]pyrimidin-4-yl)propane-2-sulfonamide | ¹H NMR (CDCl₃) δ ppm: 8.16 (s, 1H), 7.97 (s, 1H), 4.57 (t, J = 6.9 Hz, 2H), 3.31 (p, J = 6.8 Hz, 1H), 2.99-2.91 (m, 2H), 2.68-2.44 (m, 4H), 1.71-1.53 (m, 4H), 1.47-1.40 (m, 2H), 1.43 (d, J = 6.9 Hz, 6H). |

| Ex. | Structure | Name | NMR |
|---|---|---|---|
| 99 | 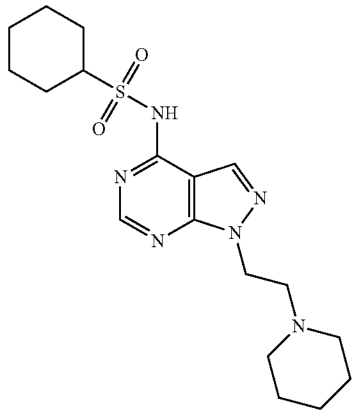 [SMILES: O=S(=O)(Nc1ncnc2c1cnn2CCN1CCCCC1)C1CCCCC1] | N-(1-(2-(piperidin-1-yl)ethyl)-1H-pyrazolo[3,4-d]pyrimidin-4-yl)cyclohexanesulfonamide | $^1$H NMR (CDCl$_3$, ca 1.4:1 rotamer mixture) δ ppm: 8.31/8.15 (2 x s, 1H), 7.93/7.92 (2 x s, 1H), 4.56/4.48 (2 x t, J = 6.5; 5.4 Hz, 2H), 3.12-2.82 (m, 3H), 2.63-2.41 (m, 4H), 2.27 (m, 2H), 1.98-1.08 (m, 14H). |
| 100 | 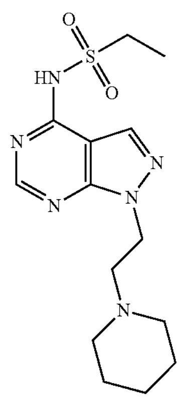 [SMILES: CCS(=O)(=O)Nc1ncnc2c1cnn2CCN1CCCCC1] | N-(1-(2-(piperidin-1-yl)ethyl)-1H-pyrazolo[3,4-d]pyrimidin-4-yl)ethanesulfonamide | $^1$H NMR (CD$_3$OD) δ ppm: 8.33 (s, 1H), 8.21 (s, 1H), 4.59 (t, J = 6.4 Hz, 2H), 3.32-3.22 (m, 2H), 3.09 (t, J = 6.4 Hz, 2H), 2.81-2.70 (m, 4H), 1.72-1.57 (m, 4H), 1.57-1.45 (m, 2H), 1.39 (t, J = 7.4 Hz, 3H). |

Example 101

Synthesis of N-(1-(2-(azepan-1-yl)ethyl)-1H-pyrazolo[3,4-d]pyrimidin-4-yl)-N-methylacetamide Step 1.—1-(2-(azepan-1-yl)ethyl)-4-chloro-1H-pyrazolo[3,4-d]pyrimidine

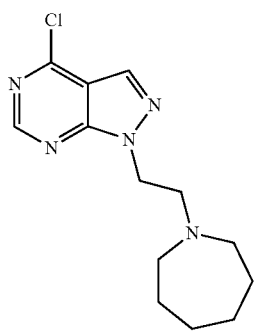 [SMILES: Clc1ncnc2c1cnn2CCN1CCCCCC1]

1-(2-(azepan-1-yl)ethyl)-4-chloro-1H-pyrazolo[3,4-d]pyrimidine (100 mg, 0.65 mmol) in anh. DMF (2 mL) was added to a suspension of NaH (91 mg, 60% dispersión in mineral oil) in anh. DMF (3 mL) at 0° C. The mixture was stirred at room temperature for 45 min. Then, 1-(2-chloroethyl)azepane hydrochloride (192 mg, 0.97 mmol) in portions at −15° C. and was kept at this temperature for 3 h. The solvent was evaporated to dryness and the residue was diluted in ethyl ether, filtered and the solvent was removed under reduced pressure. The crude was purified by flash chromatography to give 1-(2-(azepan-1-yl)ethyl)-4-chloro-1H-pyrazolo[3,4-d]pyrimidine (40 mg, 0.14 mmol, 22%) as an oil.

Step 2.—1-(2-(azepan-1-yl)ethyl)-N-methyl-1H-pyrazolo[3,4-d]pyrimidin-4-amine

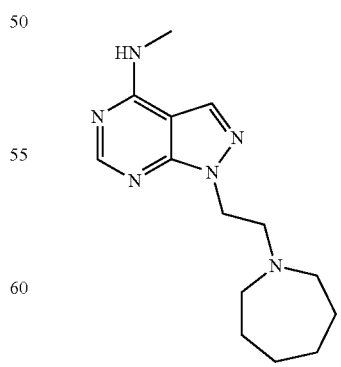

A solution of 1-(2-(azepan-1-yl)ethyl)-4-chloro-1H-pyrazolo[3,4-d]pyrimidine (40 mg, 0.14 mmol) in methylamine 33% in ethanol was stirred at room temperature monitoring the reaction by TLC. The solvent was removed under reduced pressure to give 1-(2-(azepan-1-yl)ethyl)-N-methyl-1H-pyrazolo[3,4-d]pyrimidin-4-amine (39 mg, 0.14 mmol, quantitative) as an oil.

Step 3.—N-(1-(2-(azepan-1-yl)ethyl)-1H-pyrazolo[3,4-d]pyrimidin-4-yl)-N-methylacetamide

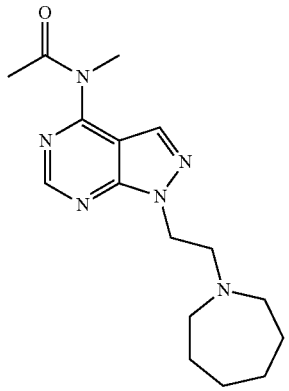 [SMILES: CC(=O)N(C)c1ncnc2c1cnn2CCN1CCCCCC1]

A mixture of 1-(2-(azepan-1-yl)ethyl)-N-methyl-1H-pyrazolo[3,4-d]pyrimidin-4-amine (20 mg, 0.07 mmol) and acetic anhydride (74 mg, 0.72 mmol) in pyridine (2 mL) was stirred at 130° C. for 15 min under microwave irradiation (150 W). Ice was added and the solvent concentrated to dryness. The residue was diluted in EtOAc, washed with water, separated and removed under reduced pressure to give an oil that was purified by flash chromatography yielding N-(1-(2-(azepan-1-yl)ethyl)-1H-pyrazolo[3,4-d]pyrimidin-4-yl)-N-methylacetamide (6 mg, 0.02 mmol, 27%). $^1$H NMR (CDCl$_3$) δ ppm: 8.75 (s, 1H), 8.07 (s, 1H), 4.60 (t, J=6.9 Hz, 2H), 3.62 (s, 3H), 3.12 (t, J=7.0 Hz, 2H), 2.89-2.66 (m, 4H), 2.44 (s, 3H), 1.68-1.56 (m, 4H), 1.56-1.45 (m, 4H).

Example 102

Synthesis of 1-(1-(2-(piperidin-1-yl)ethyl)-1H-pyrazolo[3,4-d]pyrimidin-4-yl)pyrrolidin-2-one

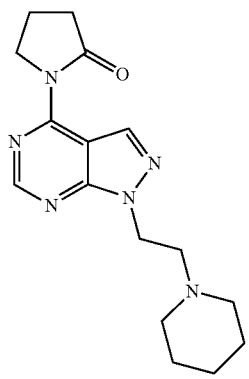 [SMILES: O=C1CCCN1c1ncnc2c1cnn2CCN1CCCCC1]

A mixture of 4-chloro-1-(2-(piperidin-1-yl)ethyl)-1H-pyrazolo[3,4-d]pyrimidine (50 mg, 0.19 mmol), pyrrolidin-2-one (0.07 mL), palladium diacetate (4.22 mg, 1.7 mmol), Xantphos (16 mg, 2.7 mmol) and cesium carbonate (67 mg, 0.20 mmol) in dry toluene (3 mL) in a microwave vial was degassed by argon for 30 minutes. The mixture was stirred at 120° C. for 20 min under microwave irradiation (150 W). The reaction was monitores by TLC. The mixture was filtered on decalite and the solvent was removed under reduced pressure. The crude was purified by flash chromatography to give 1-(1-(2-(piperidin-1-yl)ethyl)-1H-pyrazolo[3,4-d]pyrimidin-4-yl)pyrrolidin-2-one (12 mg, 0.038 mmol, 20% yield). $^1$H NMR (CDCl$_3$) δ ppm: 8.68 (s, 1H), 8.63 (s, 1H), 4.63 (t, J=7.1 Hz, 2H), 4.25-4.15 (m, 2H), 2.93 (t, J=7.1 Hz, 2H), 2.75 (t, J=8.1 Hz, 2H), 2.61-2.41 (m, 4H), 2.24 (p, J=7.7 Hz, 2H), 1.65-1.47 (m, 4H), 1.48-1.36 (m, 2H).

Example 103

Synthesis of 4-(1H-imidazol-1-yl)-1-(2-(piperidin-1-yl)ethyl)-1H-pyrazolo[3,4-d]pyrimidine

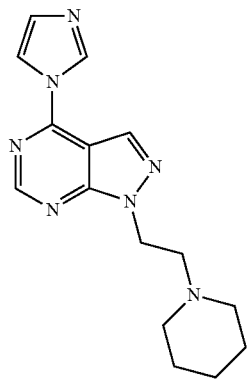 [SMILES: c1cn(-c2ncnc3c2cnn3CCN2CCCCC2)cn1]

Potassium tert-butoxide (51 mg, 0.45 mmol) was added to a solution of 1H-imidazole (31 mg, 0.45 mmol) in acetonitrile (5 mL) at room temperature and the mixture was stirred for 15 min. Then, 4-chloro-1-(2-(piperidin-1-yl)ethyl)-1H-pyrazolo[3,4-d]pyrimidine (100 mg, 0.37 mmol) was added and the mixture was stirred overnight. Water (0.5 mL) was added and the solvent was removed at reduced pressure. The resulting solid was extracted with dichloromethane and the organic phase was washed with brine and removed under reduced pressure to give 4-(1H-imidazol-1-yl)-1-(2-(piperidin-1-yl)ethyl)-1H-pyrazolo[3,4-d]pyrimidine (110 mg, 0.37 mmol, quantitative) as a pale yellow solid. $^1$H NMR (CDCl$_3$) δ ppm: 8.83 (s, 1H), 8.66 (t, J=1.1 Hz, 1H), 8.26 (s, 1H), 7.93 (t, J=1.4 Hz, 1H), 7.42-7.29 (m, 1H), 4.86-4.63 (m, 2H), 3.13-2.87 (m, 2H), 2.70-2.40 (m, 4H), 1.71-1.51 (m, 4H), 1.51-1.31 (m, 2H).

Examples 104 was prepared following the same method as in example 103:

| Ex. | Structure | Name | NMR |
|---|---|---|---|
| 104 | 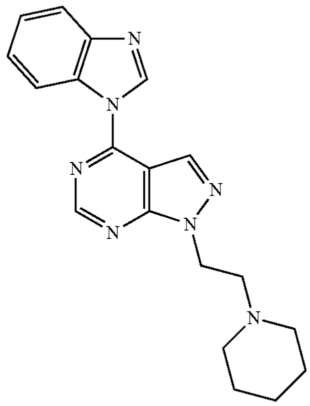 [SMILES: c1ccc2c(c1)ncn2-c1ncnc2c1cnn2CCN1CCCCC1] | 4-(1H-benzo[d]imidazol-1-yl)-1-(2-(piperidin-1-yl)ethyl)-1H-pyrazolo[3,4-d]pyrimidine | $^1$H NMR (CD$_3$OD) δ ppm: 9.18 (s, 1H), 8.99 (s, 1H), 8.72-8.58 (m, 2H), 7.82 (dd, J = 6.9, 2.4 Hz, 1H), 7.56-7.38 (m, 2H), 4.73 (t, J = 6.8 Hz, 2H), 2.96 (t, J = 6.8 Hz, 2H), 2.55 (t, J = 5.0 Hz, 4H), 1.63-1.48 (m, 4H), 1.48-1.35 (m, 2H). |

Example 105

Synthesis of 4-(2,5-dimethyl-1H-pyrrol-1-yl)-1-(2-(piperidin-1-yl)ethyl)-1H-pyrazolo[3,4-d]pyrimidine

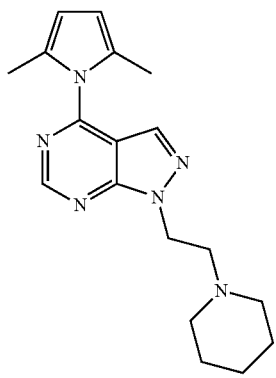 [SMILES: Cc1ccc(C)n1-c1ncnc2c1cnn2CCN1CCCCC1]

A mixture of 1-(2-(piperidin-1-yl)ethyl)-1H-pyrazolo[3,4-d]pyrimidin-4-amine (50 mg, 0.20 mmol) in hexane-2,5-dione (1.5 mL) was stirred at 180° C. for 20 min under microwave irradiation (150 W). The mixture was acidified with diluted HCl 1N and extracted with DCM. The aqueous phase was basified with NaOH 20% and extracted with DCM. The organic phase was removed under reduced pressure and the residue was purified by flash chromatography to give 4-(2,5-dimethyl-1H-pyrrol-1-yl)-1-(2-(piperidin-1-yl)ethyl)-1H-pyrazolo[3,4-d]pyrimidine (21 mg, 0.06 mmol, 32%), as a brown solid. $^1$H NMR (CDCl$_3$) δ ppm: 8.85 (s, 1H), 8.25 (s, 1H), 8.12-7.93 (m, 1H), 6.58-6.35 (m, 1H), 4.84-4.58 (m, 2H), 3.21-2.90 (m, 2H), 2.69 (s, 3H), 2.66-2.49 (m, 4H), 2.32 (s, 3H), 1.81-1.59 (m, 4H), 1.54-1.39 (m, 2H).

Example 106

Synthesis of 4-(4,4-difluoropiperidin-1-yl)-1-(2-(piperidin-1-yl)ethyl)-1H-pyrazolo[3,4-d]pyrimidine Step 1.—Synthesis of 4-chloro-1-(2-(piperidin-1-yl)ethyl)-1H-pyrazolo[3,4-d]pyrimidine To a stirred solution of 4-chloro-1H-pyrazolo[3,4-d]pyrimidine (0.2 g, 1.29 mmol) in anh THF (10 mL) were sequentially added 2-(piperidin-1-yl)ethanol (0.258 mL, 1.94 mmol) and triphenylphosphine (0.51 g, 1.94 mmol). The reaction mixture was cooled to 0° C. and diisopropylazodicarboxylate (0.38 mL, 1.94 mmol) was added dropwise and the mixture was stirred for 30 min. at 0° C. and kept overnight at 4° C. The solvent was removed at reduced pressure and the residue was dissolved in DCM and washed with diluted HCl 1 N. The aqueous phase was separated, basified and extracted with DCM. The organic phase was separated, dried and the solvent was removed under reduced pressure to give a residue that was purified by flash chromatography eluting with (EtOAc/Petroleum ether, 8:2) to yield 4-chloro-1-(2-(piperidin-1-yl)ethyl)-1H-pyrazolo[3,4-d]pyrimidine (146 mg, 55 mmol, 42%) as an oil that solidifies "on standing".

Step 2.—Synthesis of 4-(4,4-difluoropiperidin-1-yl)-1-(2-(piperidin-1-yl)ethyl)-1H-pyrazolo[3,4-d]pyrimidine

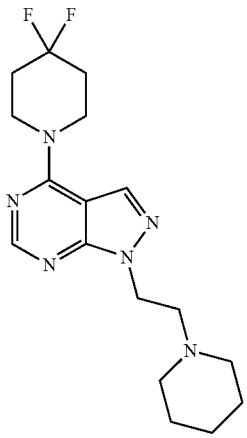 [SMILES: FC1(F)CCN(c2ncnc3c2cnn3CCN2CCCCC2)CC1]

A suspension of 4,4-difluoropiperidine hydrochloride (44 mg, 0.28 mmol) and potassium carbonate (78 mg, 0.56 mmol) in acetonitrile (3 mL) was stirred for 15 min. Then, 4-chloro-1-(2-(piperidin-1-yl)ethyl)-1H-pyrazolo[3,4-d]pyrimidine (50 mg, 0.19 mmol) in acetonitrile (2 mL) was added to the mixture and was stirred at room temperature overnight. The mixture was filtered and the solvent was removed under reduced pressure to give 4-(4,4-difluoropiperidin-1-yl)-1-(2-(piperidin-1-yl)ethyl)-1H-pyrazolo[3,4-d]pyrimidine (65 mg, 0.18 mmol, quantitative) as an oil. $^1$H NMR (CDCl$_3$) δ ppm: 8.39 (s, 1H), 7.95 (s, 1H), 4.62 (t, J=7.1 Hz, 2H), 4.11 (t, J=5.9 Hz, 4H), 3.12-2.88 (m, 2H), 2.73-2.46 (m, 4H), 2.23-2.01 (m, 4H), 1.77-1.52 (m, 4H), 1.52-1.37 (m, 2H).

Examples (107-110) were prepared following the same method as in example 106

| Ex. | Structure | Name | NMR |
|---|---|---|---|
| 107 | 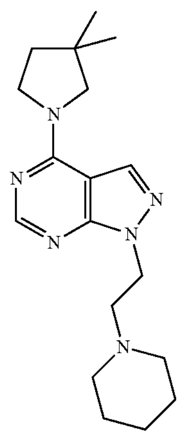 [SMILES: CC1(C)CCN(c2ncnc3c2cnn3CCN2CCCCC2)C1] | 4-(3,3-dimethylpyrrolidin-1-yl)-1-(2-(piperidin-1-yl)ethyl)-1H-pyrazolo[3,4-d]pyrimidine | $^1$H NMR (CDCl$_3$, ca 1.2:1 rotamer mixture ) δ ppm: 8.36/8.34 (2 x s, 1H), 7.93/7.90 (2 x s, 1H), 4.74-4.59 (m, 2H), 3.95-3.79 (m, 2H), 3.55/3.53 (2 x s, 2H), 3.33-3.03 (m, 2H), 2.85-2.42 (m, 4H), 1.95/1.83 (2 x t, J = 7.1 Hz, 4H), 1.79-1.59 (m, 2H), 1.55-1.39 (m, 2H), 1.22 (s, 3H), 1.18 (s, 3H). |
| 108 | 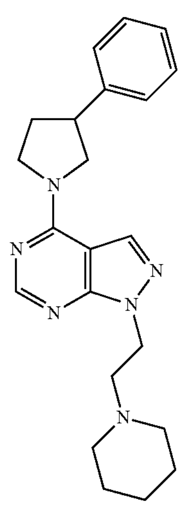 [SMILES: c1ccc(C2CCN(c3ncnc4c3cnn4CCN3CCCCC3)C2)cc1] | 4-(3-phenylpyrrolidin-1-yl)-1-(2-(piperidin-1-yl)ethyl)-1H-pyrazolo[3,4-d]pyrimidine | $^1$H NMR (CDCl$_3$, ca 1.2:1 rotamer mixture ) δ ppm: 8.26/8.24 (2 x s, 1H), 8.17/8.13 (2 x s, 1H), 7.44-7.31 (m, 4H), 7.30-7.22 (m, 1H), 4.57-4.44 (m, 2H), 4.40-4.24 (m, 1H), 4.17-4.03 (m, 1H), 4.04-3.83 (m, 1H), 3.83-3.53 (m, 2H), 2.93-2.79 (m, 2H), 2.66-2.39 (m, 4H), 2.39-2.10 (m, 1H), 1.64-1.50 (m, 4H), 1.50-1.39 (m, 2H). |

-continued

| Ex. | Structure | Name | NMR |
|---|---|---|---|
| 109 | 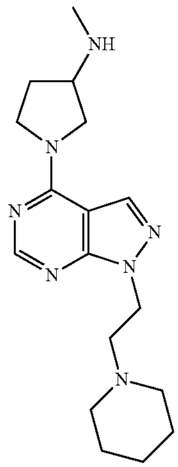 [SMILES: CNC1CCN(c2ncnc3c2cnn3CCN2CCCCC2)C1] | N-methyl-1-(1-(2-(piperidin-1-yl)ethyl)-1H-pyrazolo[3,4-d]pyrimidin-4-yl)pyrrolidin-3-amine | $^1$H NMR (CDCl$_3$) δ ppm: 8.36 (s, 1H), 7.92 (s, 1H), 4.59 (t, J = 7.0 Hz, 2H), 4.16-3.30 (m, 5H), 3.19-2.87 (m, 2H), 2.69-2.55 (m, 4H), 2.52 (s, 3H), 2.37-2.00 (m, 2H), 1.71-1.52 (m, 4H), 1.53-1.34 (m, 2H). |
| 110 | 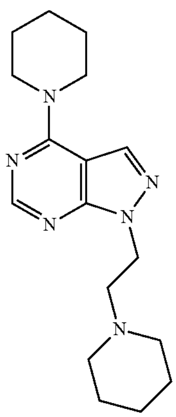 [SMILES: c1nc(N2CCCCC2)c2cnn(CCN3CCCCC3)c2n1] | 4-(piperidin-1-yl)-1-(2-(piperidin-1-yl)ethyl)-1H-pyrazolo[3,4-d]pyrimidine | $^1$H NMR (CDCl$_3$) δ ppm: 8.34 (s, 1H), 7.93 (s, 1H), 4.77-4.52 (m, 2H), 3.93 (t, J = 5.1 Hz, 4H), 3.23-2.97 (m, 2H), 2.79-2.44 (m, 4H), 1.94-1.54 (m, 10H), 1.54-1.37 (m, 2H). |

Pharmacological Data

Brain membrane preparation and binding assays for the σ1-receptor were performed as described (DeHaven-Hudkins, D. L., L. C. Fleissner, and F. Y. Ford-Rice, 1992, Characterization of the binding of [$^3$H]-(+)-pentazocine to 6 recognition sites in guinea pig brain, Eur. J. Pharmacol. 227, 371-378) with some modifications. Guinea pig brains were homogenized in 10 vols. (w/v) of Tris-HCl 50 mM 0.32 M sucrose, pH 7.4, with a Kinematica Polytron PT 3000 at 15000 r.p.m. for 30 s. The homogenate was centrifuged at 1000 g for 10 min at 4° C. and the supernatants collected and centrifuged again at 48000 g for 15 min at 4° C. The pellet was resuspended in 10 volumes of Tris-HCl buffer (50 mM, pH 7.4), incubated at 37° C. for 30 min, and centrifuged at 48000 g for 20 min at 4° C. Following this, the pellet was resuspended in fresh Tris-HCl buffer (50 mM, pH 7.4) and stored on ice until use.

The radioligand used was [$^3$H]-(+)-pentazocine at 5.0 nM and the final volume was 200 μl. The incubation was initiated with the addition of 100 μA of membrane at a final tissue concentration of approximately 5 mg tissue net weight/mL and the incubation time was 150 m. at 37° C. After incubation, the membranes were collected onto pretreated glass fiber filterplate (MultiScreen-FC, Millipore), with polyethylenimine 0.1%. The filters were washed two times with 200 μA of washing buffer (50 mM Tris Cl, pH=7.4) and then 25 μl of Ecoscint H liquid scintillation cocktail were added. Microplates were allowed to set for several hours and then quantified by liquid scintillation spectrophotometry (1450 Microbeta, Wallac). Nonspecific binding was determined with 1 μM haloperidol.

| Example | % Displacement (10$^{-6}$ M) | K$_i$ (nM) |
|---|---|---|
| 1 | 97.2 | 9.2 |
| 4 | 96.4 | 12.7 |
| 5 | 90.3 | 50.6 |
| 6 | 78.6 | 73.1 |
| 7 | 54.7 | 291.5 |
| 9 | 49.50 | 699.7 |
| 11 | 94.10 | 24.4 |
| 13 | 61.4 | 399.2 |
| 15 | 96.4 | 13.1 |
| 16 | 68.2 | 244.4 |
| 17 | 65.0 | 774.3 |
| 18 | 90.2 | 56.7 |
| 19 | 98.3 | 9.4 |
| 21 | 90.8 | 55.0 |
| 22 | 97.2 | 15.0 |
| 24 | 91.7 | 58.0 |
| 26 | 71.6 | 513.7 |
| 28 | 54.0 | 631.0 |
| 29 | 96.5 | 16.4 |
| 31 | 76.8 | 573.0 |
| 32 | 63.3 | 683.2 |
| 34 | 71.7 | 155.9 |
| 35 | 97.5 | 11.1 |

-continued

| Example | % Displacement ($10^{-6}$ M) | $K_i$ (nM) |
|---|---|---|
| 36 | n.a. | 54.6 |
| 38 | n.a. | 74.4 |
| 39 | n.a. | 115.7 |
| 41 | n.a. | 61.9 |
| 42 | n.a. | 32.7 |
| 44 | n.a. | 251.9 |
| 48 | 85.0 | 78.7 |
| 49 | 94.1 | 21.2 |
| 51 | 81.6 | 118.6 |
| 54 | 74.6 | 192.1 |
| 55 | 54.2 | 370.6 |
| 56 | 64.5 | 181.5 |
| 60 | 76.0 | 141.5 |
| 61 | 25.9 | 805.0 |
| 62 | 93.4 | 41.4 |
| 64 | 91.4 | 108.4 |
| 65 | 96.8 | 27.9 |
| 66 | 96.6 | 24.0 |
| 67 | n.a. | 29.0 |
| 68 | n.a. | 100.1 |
| 69 | n.a. | 23.4 |
| 73 | n.a. | 102.4 |
| 74 | n.a. | 212.2 |
| 75 | 97.7 | 12.8 |
| 76 | 96.8 | 14.9 |
| 77 | n.a. | 6.7 |
| 78 | n.a. | 9.2 |
| 79 | n.a. | 21.8 |
| 82 | n.a. | 12.2 |
| 83 | n.a. | 184.5 |
| 84 | n.a. | 813.5 |
| 85 | n.a. | 45.1 |
| 86 | n.a. | 328.9 |
| 88 | n.a. | 946.1 |
| 93 | n.a. | 279.7 |
| 95 | n.a. | 85.2 |
| 101 | n.a. | 221.1 |
| 105 | n.a. | 740.1 |

The invention claimed is:

1. A compound of formula I:

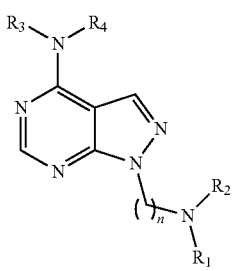

(I)

wherein $R_1$ represents a hydrogen atom; a branched or unbranched, saturated or unsaturated, unsubstituted aliphatic radical $C_{1-10}$;

a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;

a substituted or unsubstituted aryl radical; a substituted or unsubstituted, branched or unbranched arylalkyl radical $C_{1-10}$ or a benzhydryl group optionally monosubstituted;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

$R_2$ represents a branched or unbranched, saturated or unsaturated, unsubstituted aliphatic radical $C_{1-10}$;

a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkylalkyl $C_{1-10}$ group in which the cycloalkyl group is condensed with another substituted or unsubstituted mono- or polycyclic ring system;

a substituted or unsubstituted aryl radical; a substituted or unsubstituted, branched or unbranched arylalkyl radical $C_{1-10}$ or a benzhydryl group optionally monosubstituted;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

or $R_1$ and $R_2$ together with the bridging nitrogen form a substituted or unsubstituted heterocyclyl group $C_{3-9}$ or a substituted or unsubstituted heteroaryl radical $C_{3-9}$;

$R_3$ represents a hydrogen atom; or an —$COR_5$; —$C(O)NR_5R_6$; —$C(S)NR_5R_6$; —$SO_2R_7$; —$C(O)OR_5$; —$OR_5$; —$NR_5R_6$; —$NR_5C(O)R_6$ or —$NCR_5R_6$;

a branched or unbranched, saturated or unsaturated, optionally at least mono-substituted, aliphatic radical $C_{1-10}$;

a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;

an unsubstituted aryl radical; a substituted or unsubstituted, branched or unbranched arylalkyl radical $C_{1-10}$ or a benzhydryl group optionally monosubstituted;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

$R_4$ represents a —$COR_5$; —$C(O)NR_5R_6$; —$C(S)NR_5R_6$; —$SO_2R_7$; —$C(O)OR_5$; —$OR_5$; —$NR_5R_6$; —$NR_5C(O)R_6$ or —$NCR_5R_6$;

a branched or unbranched, saturated or unsaturated, optionally at least mono-substituted, aliphatic radical $C_{1-10}$;

a substituted or unsubstituted cycloalkyl radical $C_{3-9}$ a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;

an unsubstituted aryl radical; a substituted or unsubstituted, branched or unbranched arylalkyl radical $C_{1-10}$ or a benzhydryl group optionally monosubstituted;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

or $R_3$ and $R_4$ together with the bridging nitrogen form a substituted or unsubstituted heterocyclyl group $C_{3-9}$ or a substituted or unsubstituted heteroaryl radical $C_{3-9}$;

$R_5$, $R_6$ and $R_7$ independently represent a hydrogen atom;

a branched or unbranched, saturated or unsaturated, optionally at least mono-substituted, aliphatic radical $C_{1-10}$;

a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;

a substituted or unsubstituted aryl radical; a substituted or unsubstituted, branched or unbranched arylalkyl radical $C_{1-10}$ or a benzhydryl group optionally monosubstituted;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system;

n is selected from 2, 3 or 4;

or a pharmaceutically acceptable salt, stereoisomer or solvate thereof.

2. The compound according to claim 1 where $R_1$ represents a hydrogen atom or a branched or unbranched, saturated or unsaturated, aliphatic radical $C_{1-10}$; $R_2$ represents a branched or unbranched, saturated or unsaturated, aliphatic radical $C_{1-10}$; or $R_1$ and $R_2$ together with the bridging nitrogen form a substituted or unsubstituted heterocyclyl group $C_{3-9}$ or a substituted or unsubstituted heteroaryl radical $C_{3-9}$ or a pharmaceutically acceptable salt, stereoisomer or solvate thereof.

3. The compound according to claim 1 where $R_3$ represents a hydrogen atom; or an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; $R_4$ represents an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; or $R_3$ and $R_4$ together with the bridging nitrogen form a substituted or unsubstituted heterocyclyl group $C_{3-9}$ or a substituted or unsubstituted heteroaryl radical $C_{3-9}$ or a pharmaceutically acceptable salt, stereoisomer or solvate thereof.

4. The compound according to claim 1 where $R_5$, $R_6$ and $R_7$ independently represent a hydrogen atom;

a branched or unbranched, saturated or unsaturated, optionally at least mono-substituted, aliphatic radical $C_{1-10}$;

a substituted or unsubstituted cycloalkyl radical $C_{3-9}$; a branched or unbranched cycloalkyl-alkyl radical $C_{1-10}$ group in which either the alkyl group and/or the cycloalkyl group is optionally at least mono-substituted; a substituted or unsubstituted cycloalkyl $C_{3-9}$ or cycloalkyl-alkyl $C_{1-10}$ group in which the cycloalkyl group is condensed with another substituted or unsubstituted mono- or polycyclic ring system;

a substituted or unsubstituted aryl radical; a substituted or unsubstituted, branched or unbranched arylalkyl radical $C_{1-10}$ or at least mono-substituted benzhydryl group;

a substituted or unsubstituted heteroaryl radical; a substituted or unsubstituted, branched or unbranched heteroarylalkyl radical $C_{1-10}$; a substituted or unsubstituted non-aromatic heterocyclyl radical $C_{3-9}$; a substituted or unsubstituted, branched or unbranched heterocyclyl-alkyl radical $C_{1-10}$;

a substituted or unsubstituted heterocyclyl $C_{3-9}$ or heterocyclyl-alkyl radical $C_{1-10}$ group in which the heterocyclyl group is condensed with another substituted or unsubstituted mono- or polycyclic ring system or a pharmaceutically acceptable salt, stereoisomer or solvate thereof.

5. The compound according to claim 1 where $R_1$ represents hydrogen atom or branched or unbranched, saturated or unsaturated, aliphatic radical $C_{1-10}$; represents a branched or unbranched, saturated or unsaturated, aliphatic radical $C_{1-10}$; or where $R_1$ and $R_2$ together with the bridging nitrogen form an optionally at least monosubstituted group selected from:

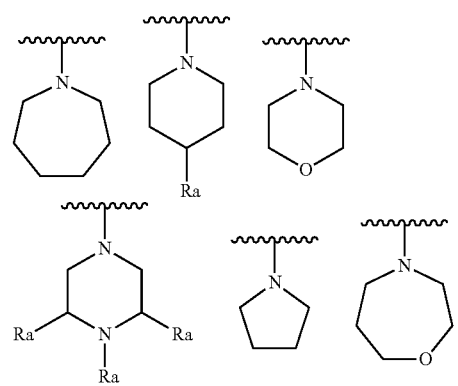

-continued

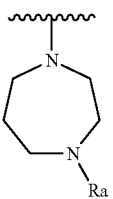

where $R_a$ independently represents a hydrogen, a branched or unbranched, saturated or unsaturated, optionally at least mono-substituted, aliphatic radical $C_{1-10}$ or a (C=O)R' group where R' represents a linear or branched $C_{1-6}$-alkyl group, or a pharmaceutically acceptable salt, stereoisomer or solvate thereof.

6. The compound according to claim 1 where $R_3$ represents a hydrogen atom; or an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; $R_4$ represents an —$COR_5$; —$C(O)NR_5R_6$; —$C(S)NR_5R_6$; —$SO_2R_7$; or a branched or unbranched, saturated or unsaturated, optionally at least mono-substituted, aliphatic radical $C_{1-10}$; or $R_3$ and $R_4$ together with the bridging nitrogen form a group selected from:

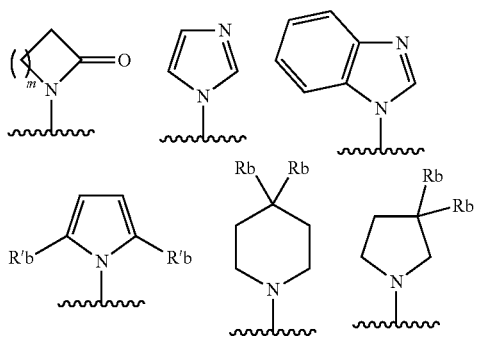

where $R_b$ independently represents a hydrogen, a halogen atom, a phenyl group, a branched or unbranched, saturated or unsaturated, optionally at least mono-substituted, aliphatic radical $C_{1-10}$ or a NHR' group where R' represents a linear or branched $C_{1-6}$-alkyl group; $R'_b$ is a branched or unbranched, saturated or unsaturated, optionally at least mono-substituted, aliphatic radical $C_{1-10}$ and m represents 1, 2, 3 or 4, or a pharmaceutically acceptable salt, stereoisomer or solvate thereof.

7. The compound according to claim 1 where $R_5$, $R_6$ and $R_7$ independently represent a hydrogen atom; a branched or unbranched, saturated or unsaturated, optionally at least mono-substituted, aliphatic radical $C_{1-10}$; or an optionally at least mono-substituted group selected from:

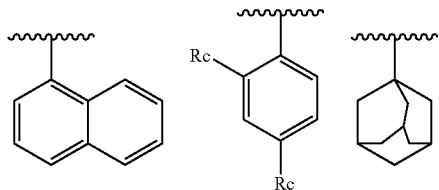

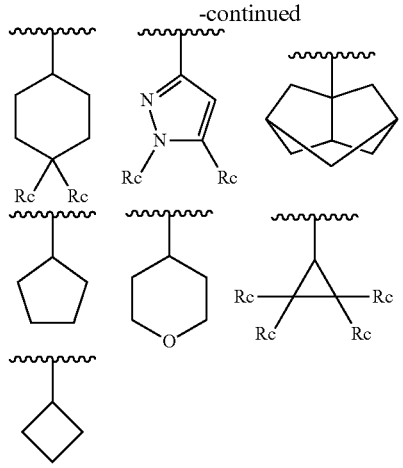

where $R_c$ independently represents a hydrogen, a halogen atom, an —OH or a branched or unbranched, saturated or unsaturated, optionally at least mono-substituted, aliphatic radical $C_{1-10}$;

or a pharmaceutically acceptable salt, stereoisomer or solvate thereof.

8. The compound according to claim 1 where $R_1$ represents hydrogen atom or a branched or unbranched, saturated or unsaturated, aliphatic radical $C_{1-10}$; $R_2$ represents a branched or unbranched, saturated or unsaturated, aliphatic radical $C_{1-10}$; or where $R_1$ and $R_2$ together with the bridging nitrogen form an optionally at least mono-substituted group selected from:

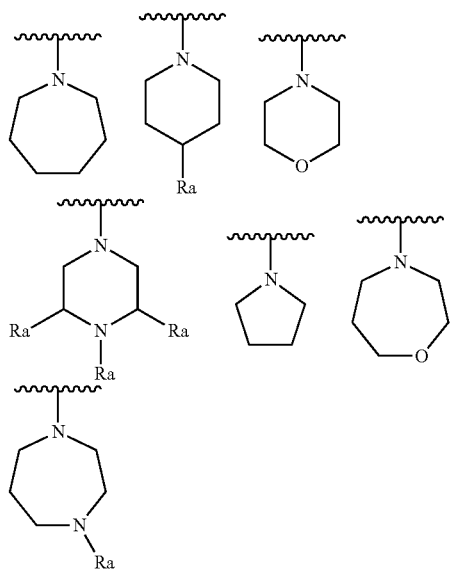

where $R_a$ independently represents a hydrogen, a branched or unbranched, saturated or unsaturated, optionally at least mono-substituted, aliphatic radical $C_{1-10}$ or a (C=O)R' group where R' represents a linear or branched $C_{1-6}$-alkyl group;

$R_3$ represents a hydrogen atom; or an —$COR_5$; —$C(O)NR_5R_6$; —$C(S)NR_5R_6$ or —$SO_2R_7$, $R_4$ represents an —$COR_5$; —$C(O)NR_5R_6$; —$C(S)NR_5R_6$ or —$SO_2R_7$; or $R_3$ and $R_4$ together with the bridging nitrogen form a group selected from:

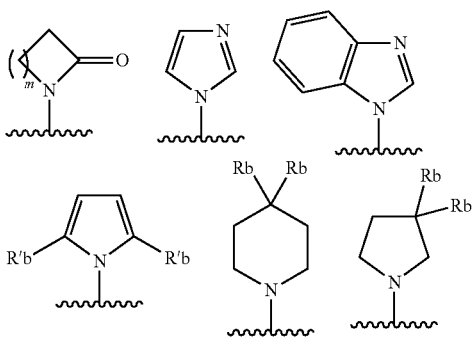

where $R_b$ independently represents a hydrogen, a halogen atom, a phenyl group, a branched or unbranched, saturated or unsaturated, optionally at least mono-substituted, aliphatic radical $C_{1-10}$ or a (C=O)R' group where R' represents a linear or branched $C_{1-6}$-alkyl group; $R'_b$ is a branched or unbranched, saturated or unsaturated, optionally at least mono-substituted, aliphatic radical $C_{1-10}$ and m represents 1, 2, 3 or 4;

$R_5$, $R_6$ and $R_7$ independently represent a hydrogen atom; a branched or unbranched, saturated or unsaturated, optionally at least mono-substituted, aliphatic radical $C_{1-10}$; or an optionally at least mono-substituted group selected from:

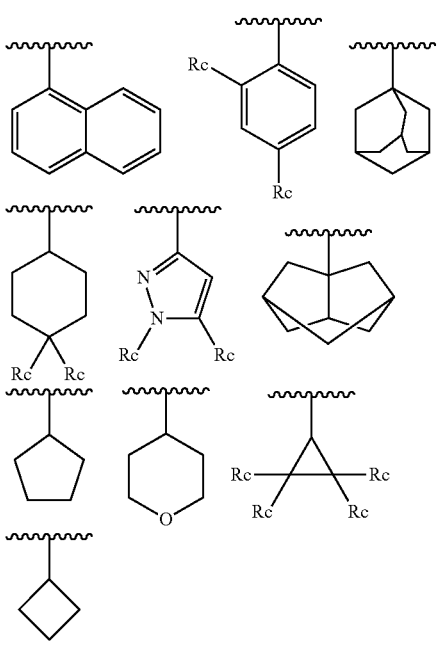

where $R_c$ independently represents a hydrogen, a halogen atom, an —OH or a branched or unbranched, saturated or unsaturated, optionally at least mono-substituted, aliphatic radical $C_{1-10}$;

n is selected from 1, 2, 3 or 4;

or a pharmaceutically acceptable salt, stereoisomer or solvate thereof.

9. The compound according to claim 1 selected from:

[1] N-(1-(2-(azepan-1-yl)ethyl)-1H-pyrazolo[3,4-d]pyrimidin-4-yl)pivalamide maleate

[2] N-(1-(2-(piperidin-1-yl)ethyl)-1H-pyrazolo[3,4-d]pyrimidin-4-yl)-1-naphthamide

[3] 2-fluoro-N-(1-(2-(piperidin-1-yl)ethyl)-1H-pyrazolo[3,4-d]pyrimidin-4-yl)benzamide

[4] N-(1-[2-(Piperidin-1-yl)ethyl]-1H-pyrazolo[3,4-d]pyrimidin-4-yl)-1-adamantylcarboxamide maleate

[5] N-(1-(2-(Piperidin-1-yl)ethyl)-1H-pyrazolo[3,4-d]pyrimidin-4-yl)pivalamide maleate

[6] N-(1-(2-(Piperidin-1-yl)ethyl)-1H-pyrazolo[3,4-d]pyrimidin-4-yl)cyclohexanecarboxamide hydrochloride

[7] 2,4-Dichloro-N-(1-(2-(piperidin-1-yl)ethyl)-1H-pyrazolo[3,4-d]pyrimidin-4-yl)benzamide hydrochloride

[8] 1,5-dimethyl-N-(1-(2-(piperidin-1-yl)ethyl)-1H-pyrazolo[3,4-d]pyrimidin-4-yl)-1H-pyrazole-3-carboxamide hydrochloride

[9] 3,5-di-tert-Butyl-N-(1-(2-(piperidin-1-yl)ethyl)-1H-pyrazolo[3,4-d]pyrimidin-4-yl)benzamide hydrochloride

[10] 2-hydroxy-N-(1-(2-(piperidin-1-yl)ethyl)-1H-pyrazolo[3,4-d]pyrimidin-4-yl)benzamide hydrochloride

[11] N-(1-(2-(piperidin-1-yl)ethyl)-1H-pyrazolo[3,4-d]pyrimidin-4-yl)(1-noradamantylcarboxamide)maleate

[12] N-(1-(2-Morpholinoethyl)-1H-pyrazolo[3,4-d]pyrimidin-4-yl)pivalamide hydrochloride

[13] N-(1-(2-(Diisopropylamino)ethyl)-1H-pyrazolo[3,4-d]pyrimidin-4-yl)pivalamide hydrochloride

[14] N-(1-(2-Morpholinoethyl)-1H-pyrazolo[3,4-d]pyrimidin-4-yl)cyclohexanecarboxamide hydrochloride

[15] N-(1-(2-(Azepan-1-yl)ethyl)-1H-pyrazolo[3,4-d]pyrimidin-4 yl)cyclohexanecarboxamide maleate

[16] N-(1-(2-(Diisopropylamino)ethyl)-1H-pyrazolo[3,4-d]pyrimidin-4-yl)cyclohexanecarboxamide maleate

[17] N-(1-[2-(Morpholinoethyl]-1H-pyrazolo[3,4-d]pyrimidin-4-yl)-1-adamantylcarboxamide hydrochloride

[18] N-(1-(2-(Diisopropylamino)ethyl)-1H-pyrazolo[3,4-d]pyrimidin-4-yl)-1-adamantylcarboxamide maleate

[19] N-(1-(2-(Azepan-1-yl)ethyl)-1H-pyrazolo[3,4-d]pyrimidin-4-yl) 1-adamantylcarboxamide hydrochloride

[20] N-(1-[2-(Morpholinoethyl]-1H-pyrazolo[3,4-d]pyrimidin-4-yl)-1-noradamantylcarboxamide hydrochloride

[21] N-(1-(2-(Diisopropylamino)ethyl)-1H-pyrazolo[3,4-d]pyrimidin-4-yl)-1-noradamantylcarboxamide hydrochloride

[22] N-(1-(2-(Azepan-1-yl)ethyl)-1H-pyrazolo[3,4-d]pyrimidin-4-yl) 1-noradamantylcarboxamide hydrochloride

[23] 2,4-Dichloro-N-(1-(2-(diisopropylamino)ethyl)-1H-pyrazolo[3,4-d]pyrimidin-4-yl)benzamide hydrochloride

[24] N-(1-(2-(Azepan-1-yl)ethyl)-1H-pyrazolo[3,4-d]pyrimidin-4-yl)-2,4-dichlorobenzamide hydrochloride

[25] 2,4-Dichloro-N-(1-(2-morpholinoethyl)-1H-pyrazolo[3,4-d]pyrimidin-4-yl)benzamide hydrochloride

[26] N-(1-(2-(Azepan-1-yl)ethyl)-1H-pyrazolo[3,4-d]pyrimidin-4-yl)tetrahydro-2H-pyran-4-carboxamide hydrochloride

[27] N-(1-(2-(Diisopropylamino)ethyl)-1H-pyrazolo[3,4-d]pyrimidin-4-yl)tetrahydro-2H-pyran-4-carboxamide hydrochloride

[28] N-(1-(2-(Diisopropylamino)ethyl)-1H-pyrazolo[3,4-d]pyrimidin-4-yl)cyclopentanecarboxamide maleate

[29] N-(1-(2-(azepan-1-yl)ethyl)-1H-pyrazolo[3,4-d]pyrimidin-4-yl)cyclopentanecarboxamide maleate

[30] N-(1-(2-(4-isopropylpiperazin-1-yl)ethyl)-1H-pyrazolo[3,4-d]pyrimidin-4-yl)pivalamide maleate

[31] N-(1-(2-(4-isopropylpiperazin-1-yl)ethyl)-1H-pyrazolo[3,4-d]pyrimidin-4-yl) 1-adamantylcarboxamide maleate

[32] N-(1-(2-(4-isopropylpiperazin-1-yl)ethyl)-1H-pyrazolo[3,4-d]pyrimidin-4-yl)cyclopentanecarboxamide maleate
[33] 4-fluoro-N-(1-(2-(4-isopropylpiperazin-1-yl)ethyl)-1H-pyrazolo[3,4-d]pyrimidin-4-yl)benzamide maleate
[34] N-(1-(2-(azepan-1-yl)ethyl)-1H-pyrazolo[3,4-d]pyrimidin-4-yl)-4-fluorobenzamide citrate
[35] N-(1-(2-(azepan-1-yl)ethyl)-1H-pyrazolo[3,4-d]pyrimidin-4-yl)-2,2,3,3-tetramethylcyclopropanecarboxamide citrate
[36] N-(1-(2-(azepan-1-yl)ethyl)-1H-pyrazolo[3,4-d]pyrimidin-4-yl)-4,4-difluorocyclohexanecarboxamide maleate
[37] N-(1-(2-(pyrrolidin-1-yl)ethyl)-1H-pyrazolo[3,4-d]pyrimidin-4-yl)cyclobutanecarboxamide maleate
[38] N-(1-(2-(pyrrolidin-1-yl)ethyl)-1H-pyrazolo[3,4-d]pyrimidin-4-yl)cyclohexanecarboxamide maleate
[39] N-(1-(2-(pyrrolidin-1-yl)ethyl)-1H-pyrazolo[3,4-d]pyrimidin-4-yl)cyclopentanecarboxamide maleate
[40] N-(1-(2-(pyrrolidin-1-yl)ethyl)-1H-pyrazolo[3,4-d]pyrimidin-4-yl)cyclopropanecarboxamide maleate
[41] N-(1-(4-(azepan-1-yl)butyl)-1H-pyrazolo[3,4-d]pyrimidin-4-yl)pivalamide maleate
[42] N-(1-(3-(azepan-1-yl)propyl)-1H-pyrazolo[3,4-d]pyrimidin-4-yl)pivalamide maleate
[43] N-(1-(2-((3S,5R)-3,5-dimethylpiperazin-1-yl)ethyl)-1H-pyrazolo[3,4-d]pyrimidin-4-yl)pivalamide
[44] 1-(1-(2-(1,4-oxazepan-4-yl)ethyl)-1H-pyrazolo[3,4-d]pyrimidin-4-yl)-3-propylurea
[45] 1-tert-Butyl-3-(1-(2-morpholinoethyl)-1H-pyrazolo[3,4-d]pyrimidin-4-yl)urea hydrochloride
[46] 1-Cyclohexyl-3-(1-(2-morpholinoethyl)-1H-pyrazolo[3,4-d]pyrimidin-4-yl)urea hydrochloride
[47] 1-Adamanthyl-3-(1-(2-morpholinoethyl)-1H-pyrazolo[3,4-d]pyrimidin-4-yl)urea hydrochloride
[48] 1-(1-(2-(Azepan-1-yl)ethyl)-1H-pyrazolo[3,4-d]pyrimidin-4-yl)-3-ethylurea hydrochloride
[49] 1-(1-(2-(Azepan-1-yl)ethyl)-1H-pyrazolo[3,4-d]pyrimidin-4-yl)-3-cyclopentylurea hydrochloride
[50] 1-(2,4-Dichlorophenyl)-3-(1-(2-morpholinoethyl)-1H-pyrazolo[3,4-d]pyrimidin-4-yl)urea hydrochloride
[51] 1-(1-(2-(Azepan-1-yl)ethyl)-1H-pyrazolo[3,4-d]pyrimidin-4-yl)-3-cyclohexylurea hydrochloride
[52] 1-(1-(2-(Diisopropylamino)ethyl)-1H-pyrazolo[3,4-d]pyrimidin-4-yl)-3-ethylurea hydrochloride
[53] 1-Cyclopentyl-3-(1-(2-(diisopropylamino)ethyl)-1H-pyrazolo[3,4-d]pyrimidin-4-yl)urea hydrochloride
[54] 1-Cyclopentyl-3-(1-(2-(piperidin-1-yl)ethyl)-1H-pyrazolo[3,4-d]pyrimidin-4-yl)urea hydrochloride
[55] 1-Ethyl-3-(1-(2-(piperidin-1-yl)ethyl)-1H-pyrazolo[3,4-d]pyrimidin-4-yl)urea hydrochloride
[56] 1-Adamanthyl-3-(1-(2-(piperidin-1-yl)ethyl)-1H-pyrazolo[3,4-d]pyrimidin-4-yl)urea hydrochloride
[57] 1-Cyclohexyl-3-(1-(2-(diisopropylamino)ethyl)-1H-pyrazolo[3,4-d]pyrimidin-4-yl)urea hydrochloride
[58] 1-(2,4-Dichlorophenyl)-3-(1-(2-(diisopropylamino)ethyl)-1H-pyrazolo[3,4-d]pyrimidin-4-yl)urea hydrochloride
[59] 1-Cyclohexyl-3-(1-(2-(piperidin-1-yl)ethyl)-1H-pyrazolo[3,4-d]pyrimidin-4-yl)urea hydrochloride
[60] 1-(2,4-Dichlorophenyl)-3-(1-(2-(piperidin-1-yl)ethyl)-1H-pyrazolo[3,4-d]pyrimidin-4-yl)urea hydrochloride
[61] 1-tert-Butyl-3-(1-(2-(diisopropylamino)ethyl)-1H-pyrazolo[3,4-d]pyrimidin-4-yl)urea hydrochloride
[62] 1-(1-(2-(azepan-1-yl)ethyl)-1H-pyrazolo[3,4-d]pyrimidin-4-yl)-3-tert-butylurea hydrochloride
[63] 1-Adamanthyl-3-(1-(2-(azepan-1-yl)ethyl)-1H-pyrazolo[3,4-d]pyrimidin-4-yl)urea maleate
[64] 1-(1-(2-(azepan-1-yl)ethyl)-1H-pyrazolo[3,4-d]pyrimidin-4-yl)-3-(2,4-dichlorophenyl)urea citrate
[65] 1-(1-(2-(azepan-1-yl)ethyl)-1H-pyrazolo[3,4-d]pyrimidin-4-yl)-3-(2,4,4-trimethylpentan-2-yl)urea maleate
[66] 1-(1-(2-(azepan-1-yl)ethyl)-1H-pyrazolo[3,4-d]pyrimidin-4-yl)-3-propylurea maleate
[67] 1-(1-(2-(azepan-1-yl)ethyl)-1H-pyrazolo[3,4-d]pyrimidin-4-yl)-3-butylurea hydrochloride
[68] 1-(1-(2-(azepan-1-yl)ethyl)-1H-pyrazolo[3,4-d]pyrimidin-4-yl)-3-cyclopropylurea hydrochloride
[69] 1-(1-(2-(azepan-1-yl)ethyl)-1H-pyrazolo[3,4-d]pyrimidin-4-yl)-3-isopropylurea hydrochloride
[70] 1-isopropyl-3-(1-(2-(pyrrolidin-1-yl)ethyl)-1H-pyrazolo[3,4-d]pyrimidin-4-yl)urea hydrochloride
[71] 1-propyl-3-(1-(2-(pyrrolidin-1-yl)ethyl)-1H-pyrazolo[3,4-d]pyrimidin-4-yl)urea hydrochloride
[72] 1-(1-(4-(azepan-1-yl)butyl)-1H-pyrazolo[3,4-d]pyrimidin-4-yl)-3-propylurea maleate
[73] 1-(1-(3-(azepan-1-yl)propyl)-1H-pyrazolo[3,4-d]pyrimidin-4-yl)-3-propyl urea
[74] 1-(1-(2-(4-tert-butylpiperidin-1-yl)ethyl)-1H-pyrazolo[3,4-d]pyrimidin-4-yl)-3-propylurea
[75] 1-(1-(2-(azepan-1-yl)ethyl)-1H-pyrazolo[3,4-d]pyrimidin-4-yl)-3-butylthiourea maleate
[76] 1-(1-(2-(azepan-1-yl)ethyl)-1H-pyrazolo[3,4-d]pyrimidin-4-yl)-3-methylthiourea maleate
[77] 1-(1-(2-(azepan-1-yl)ethyl)-1H-pyrazolo[3,4-d]pyrimidin-4-yl)-3-propylthiourea
[78] 1-(1-(2-(azepan-1-yl)ethyl)-1H-pyrazolo[3,4-d]pyrimidin-4-yl)-3-ethylthiourea
[79] 1-(1-(2-(azepan-1-yl)ethyl)-1H-pyrazolo[3,4-d]pyrimidin-4-yl)-3-cyclopropylthiourea hydrochloride
[80] 2,4-Dichloro-N-(1-(2-(d isopropylamino)ethyl)-1H-pyrazolo[3,4-d]pyrimidin-4-yl)benzenesulfonamide hydrochloride
[81] N-(1-(2-(Diisopropylamino)ethyl)-1H-pyrazolo[3,4-d]pyrimidin-4-yl)cyclohexanesulfonamide hydrochloride
[82] N-(1-(2-(4-tert-butylpiperidin-1-yl)ethyl)-1H-pyrazolo[3,4-d]pyrimidin-4-yl)pivalamide
[83] N-(1-(2-(1,4-oxazepan-4-yl)ethyl)-1H-pyrazolo[3,4-d]pyrimidin-4-yl)pivalamide
[84] N-(1-(2-(4-methyl-1,4-diazepan-1-yl)ethyl)-1H-pyrazolo[3,4-d]pyrimidin-4-yl)pivalamide
[85] N-(1-(3-(piperidin-1-yl)propyl)-1H-pyrazolo[3,4-d]pyrimidin-4-yl)pivalamide
[86] N-(1-(3-(4-methylpiperazin-1-yl)propyl)-1H-pyrazolo[3,4-d]pyrimidin-4-yl)pivalamide
[87] N-(1-(2-(4-methylpiperazin-1-yl)ethyl)-1H-pyrazolo[3,4-d]pyrimidin-4-yl)pivalamide
[88] N-(1-(4-(4-tert-butylpiperidin-1-yl)butyl)-1H-pyrazolo[3,4-d]pyrimidin-4-yl)pivalamide
[89] 1-(1-(2-(4-methyl-1,4-diazepan-1-yl)ethyl)-1H-pyrazolo[3,4-d]pyrimidin-4-yl)-3-propylurea
[90] 1-(1-(3-(4-methylpiperazin-1-yl)propyl)-1H-pyrazolo[3,4-d]pyrimidin-4-yl)-3-propylurea
[91] 1-(1-(3-(piperidin-1-yl)propyl)-1H-pyrazolo[3,4-d]pyrimidin-4-yl)-3-propylurea
[92] 1-(1-(2-(4-methylpiperazin-1-yl)ethyl)-1H-pyrazolo[3,4-d]pyrimidin-4-yl)-3-propylurea
[93] 1-(1-(4-(4-tert-butylpiperidin-1-yl)butyl)-1H-pyrazolo[3,4-d]pyrimidin-4-yl)-3-propylurea
[94] 1-(1-(2-(4-acetylpiperazin-1-yl)ethyl)-1H-pyrazolo[3,4-d]pyrimidin-4-yl)-3-propylurea

[95] 1-(1-(2-(piperidin-1-yl)ethyl)-1H-pyrazolo[3,4-d]pyrimidin-4-yl)-3-propylurea
[96] 2,4-dichloro-N-(1-(2-(piperidin-1-yl)ethyl)-1H-pyrazolo[3,4-d]pyrimidin-4-yl)benzenesulfonamide
[97] N-(1-(2-(piperidin-1-yl)ethyl)-1H-pyrazolo[3,4-d]pyrimidin-4-yl)methanesulfonamide
[98] N-(1-(2-(piperidin-1-yl)ethyl)-1H-pyrazolo[3,4-d]pyrimidin-4-yl)propane-2-sulfonamide
[99]] N-(1-(2-(piperidin-1-yl)ethyl)-1H-pyrazolo[3,4-d]pyrimidin-4-yl)cyclohexanesulfonamide
[100] N-(1-(2-(piperidin-1-yl)ethyl)-1H-pyrazolo[3,4-d]pyrimidin-4-yl)ethanesulfonamide
[101] N-(1-(2-(azepan-1-yl)ethyl)-1H-pyrazolo[3,4-d]pyrimidin-4-yl)-N-methylacetamide
[102] 1-(1-(2-(piperidin-1-yl)ethyl)-1H-pyrazolo[3,4-d]pyrimidin-4-yl)pyrrolidin-2-one
[103] 4-(1H-imidazol-1-yl)-1-(2-(piperidin-1-yl)ethyl)-1H-pyrazolo[3,4-d]pyrimidine
[104] 4-(1H-benzo[d]imidazol-1-yl)-1-(2-(piperidin-1-yl)ethyl)-1H-pyrazolo[3,4-d]pyrimidine
[105] 4-(2,5-dimethyl-1H-pyrrol-1-yl)-1-(2-(piperidin-1-yl)ethyl)-1H-pyrazolo[3,4-d]pyrimidine
[106] 4-(4,4-difluoropiperidin-1-yl)-1-(2-(piperidin-1-yl)ethyl)-1H-pyrazolo[3,4-d]pyrimidine
[107] 4-(3,3-dimethylpyrrolidin-1-yl)-1-(2-(piperidin-1-yl)ethyl)-1H-pyrazolo[3,4-d]pyrimidine
[108] 4-(3-phenylpyrrolidin-1-yl)-1-(2-(piperidin-1-yl)ethyl)-1H-pyrazolo[3,4-d]pyrimidine
[109] N-methyl-1-(1-(2-(piperidin-1-yl)ethyl)-1H-pyrazolo[3,4-d]pyrimidin-4-yl)pyrrolidin-3-amine
[110] 4-(piperidin-1-yl)-1-(2-(piperidin-1-yl)ethyl)-1H-pyrazolo[3,4-d]pyrimidine.

10. A pharmaceutical composition comprising a compound of formula (I) according to claim 1 or a pharmaceutically acceptable salt, stereoisomer or solvate thereof, and at least a pharmaceutically acceptable carrier, additive, adjuvant or vehicle.

* * * * *